United States Patent
Nastri et al.

(10) Patent No.: US 12,018,089 B2
(45) Date of Patent: *Jun. 25, 2024

(54) ANTI-CD73 ANTIBODIES AND USES THEREOF

(71) Applicant: Incyte Corporation, Wilmington, DE (US)

(72) Inventors: Horacio G. Nastri, West Chester, PA (US); Shaun M. Stewart, Chadds Ford, PA (US); Juan Carlos Almagro, Cambridge, MA (US); Jing Zhou, Boxborough, MA (US); Rebecca A. Buonpane, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 330 days.

This patent is subject to a terminal disclaimer.

(21) Appl. No.: 17/138,279

(22) Filed: Dec. 30, 2020

(65) Prior Publication Data

US 2021/0230293 A1 Jul. 29, 2021

Related U.S. Application Data

(60) Provisional application No. 62/956,847, filed on Jan. 3, 2020.

(51) Int. Cl.
| C07K 16/28 | (2006.01) |
| A61P 35/00 | (2006.01) |
| A61K 39/00 | (2006.01) |

(52) U.S. Cl.
CPC .......... C07K 16/2896 (2013.01); A61P 35/00 (2018.01); A61K 2039/505 (2013.01); C07K 2317/24 (2013.01); C07K 2317/33 (2013.01); C07K 2317/34 (2013.01); C07K 2317/76 (2013.01); C07K 2317/92 (2013.01)

(58) Field of Classification Search
CPC ................ C07K 16/28; C07K 16/2896; C07K 2317/24; C07K 2317/33; C07K 2317/34; C07K 2317/76; C07K 2317/92; C07K 2317/21; C07K 2317/73; A61P 35/00; A61K 2039/505; A61K 39/39558
See application file for complete search history.

(56) References Cited

U.S. PATENT DOCUMENTS

| 4,399,216 A | 8/1983 | Axel et al. |
| 4,634,665 A | 1/1987 | Axel et al. |
| 5,057,313 A | 10/1991 | Shih et al. |
| 5,156,840 A | 10/1992 | Goers et al. |
| 5,179,017 A | 1/1993 | Axel et al. |
| 5,714,350 A | 2/1998 | Co et al. |
| 5,731,168 A | 3/1998 | Carter et al. |
| 5,849,992 A | 12/1998 | Meade et al. |
| 5,869,046 A | 2/1999 | Presta et al. |
| 6,350,861 B1 | 2/2002 | Co et al. |
| 9,090,697 B2 | 7/2015 | Sim et al. |
| 9,388,249 B2 | 7/2016 | Sugioka et al. |
| 9,605,080 B2 | 3/2017 | Lonberg et al. |
| 9,938,356 B2 | 4/2018 | Hay et al. |
| 10,100,129 B2 | 10/2018 | Lonberg et al. |
| 10,287,362 B2 | 5/2019 | Hay et al. |
| 2004/0142342 A1 | 7/2004 | Barden et al. |
| 2007/0009518 A1 | 1/2007 | Novobrantseva et al. |
| 2011/0300136 A1 | 12/2011 | Benyunes |
| 2016/0129108 A1 | 5/2016 | Sachsenmeier et al. |
| 2018/0009899 A1 | 1/2018 | Griffin et al. |
| 2018/0030144 A1 | 2/2018 | Chanteux et al. |
| 2018/0237536 A1 | 8/2018 | Perrot et al. |
| 2018/0264107 A1 | 9/2018 | Curd et al. |
| 2019/0031766 A1 | 1/2019 | Prinz et al. |
| 2019/0077873 A1 | 3/2019 | Griffin et al. |
| 2019/0225703 A1 | 7/2019 | Caux et al. |
| 2019/0256598 A1 | 8/2019 | Wang et al. |
| 2019/0292188 A1 | 9/2019 | Wang et al. |
| 2019/0337957 A1 | 11/2019 | Wang et al. |
| 2020/0270244 A1 | 8/2020 | Huang et al. |
| 2021/0061809 A1 | 3/2021 | Han et al. |
| 2021/0230294 A1 | 7/2021 | Nastri et al. |
| 2022/0233529 A1 | 7/2022 | Wang et al. |

FOREIGN PATENT DOCUMENTS

| CL | 202200515 | 3/2022 |
| EP | 0404097 | 12/1990 |
| WO | WO 199311161 | 6/1993 |
| WO | WO 2001080884 | 11/2001 |
| WO | WO 2004079013 | 9/2004 |
| WO | WO 2005003175 | 1/2005 |
| WO | WO 2005018572 | 3/2005 |
| WO | WO 2011089004 | 7/2011 |
| WO | WO 2014153424 | 9/2014 |
| WO | WO 2016055609 | 4/2016 |
| WO | WO 2016075099 | 5/2016 |

(Continued)

OTHER PUBLICATIONS

McCarthy et al. (J. Immunol. Methods, 251(1-2): 137-149, 2001).*
Lin et al. (African Journal of Biotechnology, 10(79):18294-18302, 2011).*
Allard et al., "Immunosuppressive activities of adenosine in cancer," Current Opinion in Pharmacology, 2016, 29:7-16.
Antonioli et al., "Immunity, inflammation and cancer: a leading role for adenosine," Nature Reviews Cancer, 2013, 13(12):842-857.
Atzrodt et al., "The Renaissance of H/D Exchange," Angew Chem Int Ed., 2007, 46(41):7744-7765.

(Continued)

Primary Examiner — Nelson B Moseley, II
(74) Attorney, Agent, or Firm — Fish & Richardson P.C.

(57) ABSTRACT

Anti-CD73 antibodies are disclosed. Also disclosed are related nucleic acids, vectors, cells, and pharmaceutical compositions. Methods of treating cancer with the anti-CD73 antibodies are also disclosed.

27 Claims, 51 Drawing Sheets
Specification includes a Sequence Listing.

(56) References Cited

FOREIGN PATENT DOCUMENTS

| WO | WO 2016075176 | 5/2016 |
|----|---------------|--------|
| WO | WO 2016081748 | 5/2016 |
| WO | WO 2016131950 | 8/2016 |
| WO | WO 2017064043 | 4/2017 |
| WO | WO 2017100670 | 6/2017 |
| WO | WO 2017152085 | 9/2017 |
| WO | WO 2018013611 | 1/2018 |
| WO | WO 2018110555 | 6/2018 |
| WO | WO 2018137598 | 8/2018 |
| WO | WO 2018187512 | 10/2018 |
| WO | WO 2018215535 | 11/2018 |
| WO | WO 2018237157 | 12/2018 |
| WO | WO 2018237173 | 12/2018 |
| WO | WO 2019168847 | 9/2019 |
| WO | WO 2019170131 | 9/2019 |
| WO | WO 2019173291 | 9/2019 |
| WO | WO 2019173692 | 9/2019 |
| WO | WO 2019200256 | 10/2019 |
| WO | WO 2019222677 | 11/2019 |
| WO | WO 2019224025 | 11/2019 |
| WO | WO 2019232244 | 12/2019 |
| WO | WO 2020010197 | 1/2020 |
| WO | WO 2020097127 | 5/2020 |
| WO | WO 2020098599 | 5/2020 |
| WO | WO 2020143710 | 7/2020 |
| WO | WO 2020143836 | 7/2020 |
| WO | WO 2020216697 | 10/2020 |
| WO | WO 2020244606 | 12/2020 |
| WO | WO 2020253568 | 12/2020 |
| WO | WO 2021017892 | 2/2021 |
| WO | WO 2021032173 | 2/2021 |
| WO | WO 2021044005 | 3/2021 |
| WO | WO 2021087463 | 5/2021 |
| WO | WO 2021097223 | 5/2021 |
| WO | WO 2021127254 | 6/2021 |
| WO | WO 2021138467 | 7/2021 |
| WO | WO 2021138498 | 7/2021 |
| WO | WO 2021205383 | 10/2021 |
| WO | WO 2021213466 | 10/2021 |
| WO | WO 2021227306 | 11/2021 |
| WO | WO 2021227307 | 11/2021 |
| WO | WO 2021241729 | 12/2021 |
| WO | WO 2021259199 | 12/2021 |

OTHER PUBLICATIONS

Berge et al., "Pharmaceutical salts," Journal of Pharmaceutical Science, 1977, 66(2):1-19.
Better et al., "*Escherichia coli* secretion of an active chimeric antibody fragment," Science, 1988, 240:1041-1043.
Better et al., "Expression of engineered antibodies and antibody fragments in microorganisms," Methods in Enzymology, 1989, 178:476-496.
Bird et al., "Single chain antibody variable regions," TIBTECH, 1991, 9:132-137.
Blom et al., "Preparative LC-MS Purification: Improved Compound Specific Method Optimization," J Combi Chem., 2004, 6(6):874-883.
Borrmann, T. et al., "1-alkyl-8-(piperazine-1-sulfonyl)phenylxanthines: development and characterization of adenosine A2B receptor antagonists and a new radioligand with subnanomolar affinity and subtype specificity," J Med Chem., 2009, 52(13):3994-4006.
Bowman et al., "An Exceptionally Potent Inhibitor of Human CD73," Biochem., Aug. 6, 2019, 58(31):3331-3334.
Boyd, "Some practical considerations and applications of the National Cancer Institute in vitro anticancer drug discovery screen," Drug Development Research, 1995, 34:91-109.
Braganhol et al., "Ecto-5'-nucleotidase/CD73 inhibition by quercetin in the human U138MG glioma cell line," Biochim Biophys Acta., 2007, 1770:1352-1359.
Carlsson et al., "Structure-based discovery of A2A adenosine receptor ligands," J Med Chem., 2010, 53:3748-3755.
Carter et al., "High level *Escherichia coli* expression and production of a bivalent humanized antibody fragment," Bio/Technology, 1992, 10:163-167.
Carter et al., "Humanization of an anti-p185HER2 antibody for human cancer therapy," PNAS, 1992, 89:4285-4289.
Co et al., "A humanized antibody specific for the platelet integrin gpIIb/IIIa," J Immunol., 1994, 152:2968-2976.
Dorai, "Aglycosylated chimeric mouse/human IgG1 antibody retains some effector function," Hybridoma, 1991, 10(2):211-217.
Friend, "Phase I study of an engineered aglycosylated humanized CD3 antibody in renal transplant rejection," Transplantation, 1999, 68:1632-1637.
GenBank Accession No. NP_002517, "5'-nucleotidase isoform 1 preproprotein [*Homo sapiens*]," Apr. 26, 2021, 3 pages.
GenBank Accession No. NP_035981, "5'-nucleotidase preproprotein [Mus musculus]," May 24, 2021, 3 pages.
Graddis et al., "Designing proteins that work using recombinant technologies," Curr Pharm Biotechnol., 2002, 3:285-297.
Hand et al., "Comparative biological properties of a recombinant chimeric anti-carcinoma mAb and a recombinant aglycosylated variant," Cancer Immunol Immunother., 1992, 35:165-174.
Hasko et al., "Shaping of monocyte and macrophage function by adenosine receptors," Pharmacol. Ther., 2007, 113(2):264-275.
Hay et al., "Targeting CD73 in the tumor microenvironment with MEDI9447," Oncoimmunol., Jul. 11, 2016, 5(8):e1208875.
Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29:949-956.
Holliger et al., ""Diabodies": small bivalent and bispecific antibody fragments," Proc Natl Acad Sci USA., 1993, 90:6444-6448.
Hudson et al., "High avidity scFv multimers; diabodies and triabodies," J Immunol Methods, 1999, 231:177-189.
Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.
International Search Report and Written Opinion in International Application No. PCT/US2020/067533, dated Apr. 21, 2021, 20 pages.
International Search Report and Written Opinion in International Application No. PCT/US2020/067576, dated Apr. 28, 2021, 17 pages.
International Preliminary Report on Patentability in International Application No. PCT/US2020/067576, dated Jul. 14, 2022, 10 pages.
International Preliminary Report on Patentability in International Application No. PCT/US2020/067533, dated Jul. 14, 2022, 10 pages.
Isaacs et al., "Therapy with monoclonal antibodies. An in vivo model for the assessment of therapeutic potential," J Immunol., 1992, 148:3062-3071.
Kaufman and Sharp, "Amplification and expression of sequences cotransfected with a modular dihydrofolate reductase complementary dna gene," Mol Biol., 1982, 159(4):601-621.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Knapp et al., "Crystal structure of the human ecto-5'-nucleotidase (CD73): insights into the regulation of purinergic signaling," Structure, 2012, 20(12):2161-2173.
Lamoyi, "Preparation of F(ab')2 fragments from mouse IgG of various subclasses," Methods in Enzymology, 1986, 121:652-663.
Leatherbarrow and Dwek, "The effect of aglycosylation on the binding of mouse IgG to staphylococcal protein A," Febs Lett., Dec. 12, 1983, 164(2):227-230.
Leatherbarrow et al., "Effector functions of a monoclonal aglycosylated mouse IgG2a: binding and activation of complement component C1 and interaction with human monocyte Fc receptor," Mol Immunol., 1985, 22(4):407-415.
Lei et al., "Characterization of the Erwinia carotovora pelB gene and its product pectate lyase," J Bacteriol., 1987, 169:4379-4383.

(56) References Cited

OTHER PUBLICATIONS

Livingston et al., "Adenosine, inflammation and asthma—a review," Inflamm Res., 2004, 53(5):171-178.
Matsumoto et al., "Alterations in vasoconstrictor responses to the endothelium-derived contracting factor uridine adenosine tetraphosphate are region specific in DOCA-salt hypertensive rats," Pharmacol Res., 2012, 65:81-90.
Millstein et al., "Hybrid Hybridomas and their use in immunohistochemistry," Nature, 1983, 305:537-539.
Mizushima et al., "pEF-BOS, a powerful mammalian expression vector," Nucleic Acids Res., 1990, 18:5322.
Mulligan et al., "Synthesis of rabbit beta-globin in cultured monkey kidney cells following infection with a SV40 beta-globin recombinant genome," Nature, 1979, 277:108-114.
Niemelä et al., "IFN-alpha induced adenosine production on the endothelium: a mechanism mediated by CD73 (ecto-5'-nucleotidase) up-regulation," J Immunol., 2004, 172:1646-1653.
Nose and Wigzell, "Biological significance of carbohydrate chains on monoclonal antibodies," Immunology, 1983, 80:6632-6636.
Perez de la Lastra et al., "Epitope mapping of 10 monoclonal antibodies against the pig analogue of human membrane cofactor protein (MCP)," Immunol., Apr. 1, 1999, 96(4):663-670.
Pluckthun, "Antibodies from *Escherichia coli*," The Pharmacology of Monoclonal Antibodies, 1994, 113:269-315.
Pluckthun et al., "Expression of functional antibody Fv and Fab fragments in *Escherichia coli*," Methods in Enzymology, 1989, 178:476-496.
Powers et al., "Expression of single-chain Fv-Fc fusions in Pichia pastoris," J Immunol Methods., 2001, 251:123-135.
Raju, "Glycosylation Variations with Expression Systems and Their Impact on Biological Activity of Therapeutic Immunoglobulins," BioProcess International, Apr. 2003, 44-53.
Remington's Pharmaceutical Sciences, "Preformulation," 17th ed., Mack Publishing Company, Easton, Pa., 1985, p. 1418.
Rousseaux et al., "Optimal conditions for the preparation of proteolytic fragments from monoclonal IgG of different rat IgG subclasses," Methods in Enzymology, 1989, 121:663-669.
Ryzhov et al., "Host A2B Adenosine Receptors Promote Carcinoma Growth," Neoplasia, 2008, 10:987-995.
Sachdeva et al., "Adenosine and its receptors as therapeutic targets: An overview," Saudi Pharmaceutical Journal, 2013, 21:245-253.
Sadej et al., "Ecto-5'-Nucleotidase (eN, CD73) is Coexpressed with Metastasis Promoting Antigens in Human Melanoma Cells," Nucleosides Nucleotides Nucleic Acids, 2006, 25:1119-1123.
Salmi and Jalkanen, "Host CD73 impairs anti-tumor immunity," OncoImmunology, 2012, 1:247-248.
Sattin and Rall, "The effect of adenosine and adenine nucleotides on the cyclic adenosine 3', 5'-phosphate content of guinea pig cerebral cortex slices," Mol Pharmacol., 1970, 6:13-23.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Stagg and Smyth, "Extracellular adenosine triphosphate and adenosine in cancer," Oncogene, 2010, 29(39):5346-5358.
Stagg, "The double-edge sword effect of anti-CD73 cancer therapy," OncoImmunology, 2012, 1:217-218.
Tao, "Studies of aglycosylated chimeric mouse-human IgG. Role of carbohydrate in the structure and effector functions mediated by the human IgG constant region.," J Immunol., 1989, 143(8):2595-2601.
Tautenhahn et al., "Purinergic modulation of the excitatory synaptic input onto rat striatal neurons," Neuropharmacology, 2012, 62:1756-1766.
Umana et al., "Engineered glycoforms of an antineuroblastoma IgG1 with optimized antibody-dependent cellular cytotoxic activity," Nat Biotechnol., 1999, 17(2):176-180.
Urlaub and Chasin "Isolation of Chinese hamster cell mutants deficient in dihydrofolate reductase activity," Proc Natl Acad Sci USA., 1980, 77(7):4216-4220.
Walker et al., "Aglycosylation of human IgG1 and IgG3 monoclonal antibodies can eliminate recognition by human cells expressing FcγRI and/or FcγRII receptors," Biochem J., 1989, 259:347-353.
Ward and Ghetie, "The effector functions of immunoglobulins: implications for therapy," Therapeutic Immunology, 1995, 2(2):77-94.
Ward et al., "Binding activities of a repertoire of single immunoglobulin variable domains secreted from *Escherichia coli*," Nature, 1989, 341(6242):544-546.
Wright and Morrison, "Effect of glycosylation on antibody function: implications for genetic engineering," TIBTECH, 1997, 15(1):26-32.
Xu et. al., "Design, synthesis and biological evaluation of deuterated nintedanib for improving pharmacokinetic properties," J Label Compd Radiopharm., 2015, 58(7):308-312.
Zhang, "CD73: a novel target for cancer immunotherapy," 2010, Cancer Res., 2010, 70:6407-6411.
Zhang, "CD73 promotes tumor growth and metastasis," OncoImmunology, 2012, 1:67-17.
Beavis et al., "Targeting the adenosine 2A receptor enhances chimeric antigen receptor T cell efficacy," J. Clin. Investigation, Mar. 2017, 127(3):929-941.
ClinicalTrials.gov [online], "CPI-006 Alone and in Combination With Ciforadenant and With Pembrolizumab for Patients With Advanced Cancers," NCT03454451, last updated Aug. 3, 2022, retrieved on May 31, 2023, retrieved from URL<https://clinicaltrials.gov/ct2/show/NCT03454451>, 19 pages.
DiRenzo et al., "AB928, a Dual Antagonist of the A2aR and A2bR Adenosine Receptors, Relieves Adenosine Mediated Immune Suppression," Poster, Presented at Proceedings of the Fourth CRI-CIMT-EATI-AACR International Cancer Immunotherapy Conference: Translating Science into Survival, New York, NY, Sep. 30-Oct. 3, 2018, 1 page.
GlobeNewswire.com [online], "Corvus Pharmaceuticals Announces Initiation of Phase 1/1b Clinical Trial of Investigational Anti-CD73 Antibody, CPI-006, in Patients with Advanced Cancer," Apr. 26, 2018, retrieved on May 31, 2023, retrieved from URL<https://www.globenewswire.com/news-release/2018/04/26/1488146/0/en/Corvus-Pharmaceuticals-Announces-Initiation-of-Phase-1-1b-Clinical-Trial-of-Investigational-Anti-CD73-Antibody-CPI-006-in-Patients-with-Advanced-Cancer.html>, 6 pages.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, Dec. 2013, 15(12):1400-1409.
Leone et al., "Inhibition of the adenosine A2a receptor modulates expression of T cell coinhibitory receptors and improves effector function for enhanced checkpoint blockade and ACT in murine cancer models," Cancer Immunol. Immunotherapy, Jun. 19, 2018, 67(8):1271-1284.
Mariuzza et al., "The structural basis of antigen-antibody recognition," Annu. Rev. Biophys. Biophys. Chem., 1987, 16:139-159.
Vigano et al., "Targeting Adenosine in Cancer Immunotherapy to Enhance T-Cell Function," Front. Immunology, Jun. 6, 2019, 10:925, 30 pages.
Willingham et al., "A2AR Antagonism with CPI-444 Induces Antitumor Responses and Augments Efficacy to Anti-PD-(L)1 and Anti-CTLA-4 in Preclinical Models," Cancer Immunol. Research, Oct. 2018, 6(10):1136-1149.
Lee et al., "Abstract #: P484: CB-708, an orally bioavailable small molecule inhibitor of CD73 with immunostimulatory and anti-tumor activity," Poster, Presented at the Proceedings of 34th Annual Meeting & Pre-Conference Programs of the Society for Immunotherapy

(56) References Cited

OTHER PUBLICATIONS of Cancer (SITC): Part 1, National Harbor, MD, Nov. 6-10, 2019; Journal for Immunotherapy of Cancer, Nov. 6, 2019, 7(Suppl. 1):263-264.

* cited by examiner

FIG. 1A

CL25_hu_10-4 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)

CL25_hu_10-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

HzCL25 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)

HzCL25 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_10-6 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)

CL25_hu_10-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_11-4 VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)

CL25_hu_11-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

FIG. 1B

CL25_hu_11-5_VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)

CL25_hu_11-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_11-6 VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)

CL25_hu_11-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_8-4 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

CL25_hu_8-5 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

FIG. 1C

CL25_hu_8-6 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_9-4 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

CL25_hu_9-5 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_9-6 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

FIG. 1D

```
CL25        QVQLQQSGAELARPGASVKLSCRASGYTFTSYGLSWVKQRTGQGLEWIGEIYPGSGNTYY  60
CL_hu_10-4  EVQLVQSGAEVKKPGESLKISCKGSGYTFTSYGLSWVRQMPGKGLEWMGEIYPGSGNTYY  60
HzCL25      EVQLVQSGAEVKKPGESLKISCKGSGYTFTSYGLSWVRQMPGKGLEWMGEIYPGSGNTYY  60
CL25_hu_10-6 EVQLVQSGAEVKKPGESLKISCKGSGYTFTSYGLSWVRQMPGKGLEWMGEIYPGSGNTYY  60
CL25_hu_9-4  QVQLVQSGAEVKKPGSSVKVSCKASGYTFTSYGLSWVRQAPGQGLEWMGEIYPGSGNTYY  60
CL25_hu_9-5  QVQLVQSGAEVKKPGSSVKVSCKASGYTFTSYGLSWVRQAPGQGLEWMGEIYPGSGNTYY  60
CL25_hu_9-6  QVQLVQSGAEVKKPGSSVKVSCKASGYTFTSYGLSWVRQAPGQGLEWMGEIYPGSGNTYY  60
CL25_hu_11-4 QVQLVQSGAEVKKPGASVKVSCKASGYTFTSYGLSWVRQATGQGLEWMGEIYPGSGNTYY  60
CL25_hu_11-5 QVQLVQSGAEVKKPGASVKVSCKASGYTFTSYGLSWVRQATGQGLEWMGEIYPGSGNTYY  60
CL25_hu_11-6 QVQLVQSGAEVKKPGASVKVSCKASGYTFTSYGLSWVRQATGQGLEWMGEIYPGSGNTYY  60
CL25_hu_8-4  QVQLVQSGAEVKKPGASVKVSCKASGYTFTSYGLSWVRQATGQGLEWMGEIYPGSGNTYY  60
CL25_hu_8-5  QVQLVQSGAEVKKPGASVKVSCKASGYTFTSYGLSWVRQATGQGLEWMGEIYPGSGNTYY  60
CL25_hu_8-6  QVQLVQSGAEVKKPGASVKVSCKASGYTFTSYGLSWVRQATGQGLEWMGEIYPGSGNTYY  60
             :***  *****: :** *:*:**:.************:*   *:****:**********

CL25        NEKFKGKATLTADKSSSTAYMELRSLTSEDSAVYFCARYDYLGSSYGFDYWGQGTTLTVS  120
CL_hu_10-4  NEKFKGQVTISADKSISTAYLQWSSLKASDTAMYYCARYDYLGSSYGFDYWGAGTTVTVS  120
HzCL25      NEKFKGQVTISADKSISTAYLQWSSLKASDTAMYYCARYDYLGSSYGFDYWGAGTTVTVS  120
CL25_hu_10-6 NEKFKGQVTISADKSISTAYLQWSSLKASDTAMYYCARYDYLGSSYGFDYWGAGTTVTVS  120
CL25_hu_9-4  NEKFKGRVTITADESTSTAYMELSSLRSEDTAVYYCARYDYLGSSYGFDYWGAGTTVTVS  120
CL25_hu_9-5  NEKFKGRVTITADESTSTAYMELSSLRSEDTAVYYCARYDYLGSSYGFDYWGAGTTVTVS  120
CL25_hu_9-6  NEKFKGRVTITADESTSTAYMELSSLRSEDTAVYYCARYDYLGSSYGFDYWGAGTTVTVS  120
CL25_hu_11-4 NEKFKGRVTMTANTSISTAYMELSSLRSEDTAVYYCARYDYLGSSYGFDYWGAGTTVTVS  120
CL25_hu_11-5 NEKFKGRVTMTANTSISTAYMELSSLRSEDTAVYYCARYDYLGSSYGFDYWGAGTTVTVS  120
CL25_hu_11-6 NEKFKGRVTMTANTSISTAYMELSSLRSEDTAVYYCARYDYLGSSYGFDYWGAGTTVTVS  120
CL25_hu_8-4  NEKFKGRVTMTRNTSISTAYMELSSLRSEDTAVYYCARYDYLGSSYGFDYWGAGTTVTVS  120
CL25_hu_8-5  NEKFKGRVTMTRNTSISTAYMELSSLRSEDTAVYYCARYDYLGSSYGFDYWGAGTTVTVS  120
CL25_hu_8-6  NEKFKGRVTMTRNTSISTAYMELSSLRSEDTAVYYCARYDYLGSSYGFDYWGAGTTVTVS  120
             ******:.*::  : * ****:: ** :.*:*:*:********************:***

CL25        S 120 (SEQ ID NO:26)
CL_hu_10-4  S 121 (SEQ ID NO:22)
HzCL25      S 121 (SEQ ID NO:22)
CL25_hu_10-6 S 121 (SEQ ID NO:22)
CL25_hu_9-4  S 121 (SEQ ID NO:84)
CL25_hu_9-5  S 121 (SEQ ID NO:84)
CL25_hu_9-6  S 121 (SEQ ID NO:84)
CL25_hu_11-4 S 121 (SEQ ID NO:82)
CL25_hu_11-5 S 121 (SEQ ID NO:82)
CL25_hu_11-6 S 121 (SEQ ID NO:82)
CL25_hu_8-4  S 121 (SEQ ID NO:83)
CL25_hu_8-5  S 121 (SEQ ID NO:83)
CL25_hu_8-6  S 121 (SEQ ID NO:83)
```

FIG. 1E

```
CL25         DIVMTQSHKFMSTSVGDRVSITCKASQDVSTAVAWYQQKPGQSPKLLIYSASYRYNGVPD 60
HzCL25       DIVMTQSPDSLAVSLGERATINCKASQDVSTAVAWYQQKPGQPPKLLIYSASYRYSGVPD 60
CL25_hu_11-5 DIVMTQSPDSLAVSLGERATINCKASQDVSTAVAWYQQKPGQPPKLLIYSASYRYSGVPD 60
CL25_hu_8-5  DIVMTQSPDSLAVSLGERATINCKASQDVSTAVAWYQQKPGQPPKLLIYSASYRYSGVPD 60
CL25_hu_9-5  DIVMTQSPDSLAVSLGERATINCKASQDVSTAVAWYQQKPGQPPKLLIYSASYRYSGVPD 60
CL25_hu_10-4 DIQMTQSPSSLSASVGDRVTITCKASQDVSTAVAWYQQKPGKAPKLLLYSASYRYSGVPS 60
CL25_hu_11-4 DIQMTQSPSSLSASVGDRVTITCKASQDVSTAVAWYQQKPGKAPKLLLYSASYRYSGVPS 60
CL25_hu_8-4  DIQMTQSPSSLSASVGDRVTITCKASQDVSTAVAWYQQKPGKAPKLLLYSASYRYSGVPS 60
CL25_hu_9-4  DIQMTQSPSSLSASVGDRVTITCKASQDVSTAVAWYQQKPGKAPKLLLYSASYRYSGVPS 60
CL25_hu_10-6 AIRMTQSPSSFSASTGDRVTITCKASQDVSTAVAWYQQKPGKAPKLLIYSASYRYSGVPS 60
CL25_hu_11-6 AIRMTQSPSSFSASTGDRVTITCKASQDVSTAVAWYQQKPGKAPKLLIYSASYRYSGVPS 60
CL25_hu_8-6  AIRMTQSPSSFSASTGDRVTITCKASQDVSTAVAWYQQKPGKAPKLLIYSASYRYSGVPS 60
CL25_hu_9-6  AIRMTQSPSSFSASTGDRVTITCKASQDVSTAVAWYQQKPGKAPKLLIYSASYRYSGVPS 60
              * **** . ::.* *:*.:*.***********:****:*******.***.

CL25         RFTGSGSGTDFTFTISSVQAEDLAVYYCQQHYNTPYTFGGGTKLEIK 107 (SEQ ID NO:27)
HzCL25       RFSGSGSGTDFTLTISSLQAEDVAVYYCQQHYNTPYTFGGGTKLEIK 107 (SEQ ID NO:23)
CL25_hu_11-5 RFSGSGSGTDFTLTISSLQAEDVAVYYCQQHYNTPYTFGGGTKLEIK 107 (SEQ ID NO:23)
CL25_hu_8-5  RFSGSGSGTDFTLTISSLQAEDVAVYYCQQHYNTPYTFGGGTKLEIK 107 (SEQ ID NO:23)
CL25_hu_9-5  RFSGSGSGTDFTLTISSLQAEDVAVYYCQQHYNTPYTFGGGTKLEIK 107 (SEQ ID NO:23)
CL25_hu_10-4 RFSGSGSGTDYTLTISSLQPEDFATYYCQQHYNTPYTFGGGTKLEIK 107 (SEQ ID NO:80)
CL25_hu_11-4 RFSGSGSGTDYTLTISSLQPEDFATYYCQQHYNTPYTFGGGTKLEIK 107 (SEQ ID NO:80)
CL25_hu_8-4  RFSGSGSGTDYTLTISSLQPEDFATYYCQQHYNTPYTFGGGTKLEIK 107 (SEQ ID NO:80)
CL25_hu_9-4  RFSGSGSGTDYTLTISSLQPEDFATYYCQQHYNTPYTFGGGTKLEIK 107 (SEQ ID NO:80)
CL25_hu_10-6 RFSGSGSGTDFTLTISCLQSEDFATYYCQQHYNTPYTFGGGTKLEIK 107 (SEQ ID NO:81)
CL25_hu_11-6 RFSGSGSGTDFTLTISCLQSEDFATYYCQQHYNTPYTFGGGTKLEIK 107 (SEQ ID NO:81)
CL25_hu_8-6  RFSGSGSGTDFTLTISCLQSEDFATYYCQQHYNTPYTFGGGTKLEIK 107 (SEQ ID NO:81)
CL25_hu_9-6  RFSGSGSGTDFTLTISCLQSEDFATYYCQQHYNTPYTFGGGTKLEIK 107 (SEQ ID NO:81)
              **;*******;*;***.;* **.*.*********************
```

Cellular CD73 inhibition - A375 cells

Cellular CD73 inhibition - MDA-MB-231 cells

FIG. 12
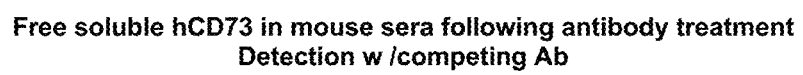
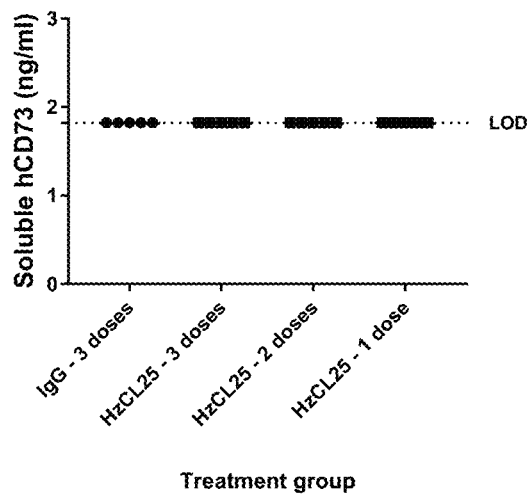
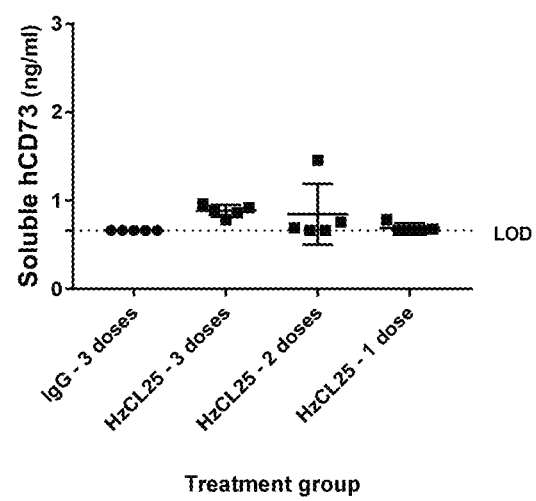

Cell binding-MDA-MB-231cells

Cell binding-A375 cells

Cellular CD73 inhibition - A375 cells

Cellular CD73 Inhibition- MDA-MB-231 cells

FIG. 20
Total soluble hCD73 in mouse sera following antibody treatment
Detection with non-competing Ab
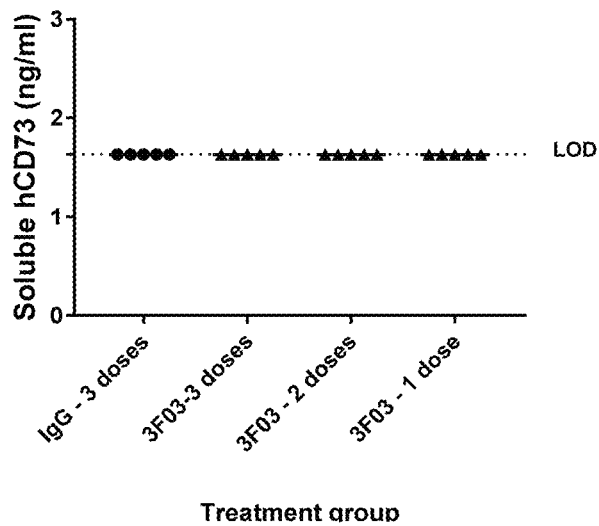
Free soluble hCD73 in mouse sera following antibody treatment
Detection with competing Ab
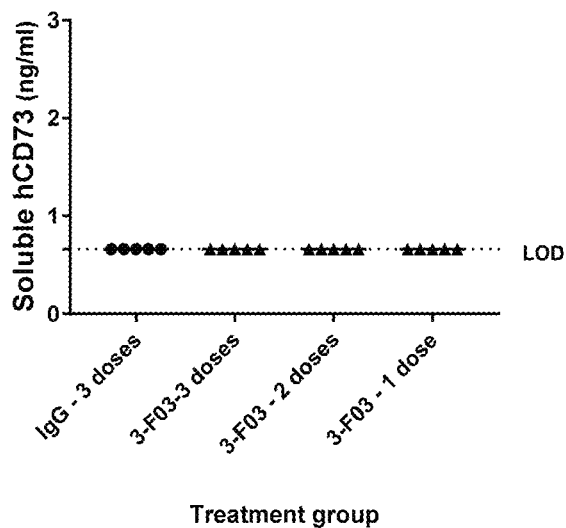

FIG. 21A

3-F03_VH_yeast
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_VL_yeast
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3-F03_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_411_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_411_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_413_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_413_LC
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 21B

3-F03_396_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_396_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_408_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_408_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_402_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_402_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_384_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_384_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

FIG. 21C

3-F03_399_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_399_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_414_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_414_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_390_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_390_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_398_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_398_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 21D

3-F03_387_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_387_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_386_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_386_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_401_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_401_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_410_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_410_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 21E

3-F03_389_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_389_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_392_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_392_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_404_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_404_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_419_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_419_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 21F

3-F03_416_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_416_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_407_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_407_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_395_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_395_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_388_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_388_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

FIG. 21G

3-F03_397_VH
EVQLVESGGGLVQPGGSLRLSCAASGFTFSSYDMHWVRQAPGKGLEWVAVMSYSGS
NKYYADSVKGRFTISRDNSKNTLYLQMNSLRAEDTAVYYCATEIAAKGDYWGQGTL
VTVSS (SEQ ID NO:68)

3-F03_397_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_385_VH
EVQLVESGGGLVQPGGSLRLSCAASGFTFSSYDMHWVRQAPGKGLEWVAVMSYSGS
NKYYADSVKGRFTISRDNSKNTLYLQMNSLRAEDTAVYYCATEIAAKGDYWGQGTL
VTVSS (SEQ ID NO:68)

3-F03_385_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_400_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_400_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_409_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_409_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 21H

3-F03_403_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)

3-F03_403_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_415_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)

3-F03_415_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_391_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)

3-F03_391_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_406_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)

3-F03_406_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 21I

3-F03_412_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_412_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_394_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)

3-F03_394_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_418_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)

3-F03_418_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3_F03_417_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_417_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 21J

3_F03_393_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_393_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3_F03_405_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_405_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 24

Human IgG1 heavy chain CH1-hinge-CH2-CH3, with N297A mutation
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVH
NAKTKPREEQYASTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPG (SEQ
ID NO:73)

Human IgG1 heavy chain CH1-hinge-CH2-CH3, with N297A mutation with C-terminal lysine
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVH
NAKTKPREEQYASTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ
ID NO:75)

Human kappa light chain constant region
RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ
ID NO:74)

FIG. 25A

HzCL25 heavy chain DNA sequence
GAAGTGCAGCTCGTGCAGTCCGGAGCCGAAGTGAAAAAGCCTGGAGAGTCCCTGAAGATC
AGCTGCAAGGGTTCCGGCTATACATTCACCTCCTACGGGCTCAGCTGGGTCAGACAGATG
CCGGGAAAGGGTCTTGAGTGGATGGGAGAGATCTACCCGGGCTCCGGCAACACCTACTAC
AACGAAAAGTTCAAGGGCCAGGTCACCATTTCCGCCGACAAGTCAATCTCCACCGCTTAC
CTCCAATGGTCGAGCCTGAAGGCATCGGATACCGCGATGTACTACTGCGCCCGCTACGAC
TACCTGGGCTCGTCATACGGCTTCGATTACTGGGGGGCGGGAACTACCGTGACTGTGTCC
TCCGCCTCCACTAAGGGACCCTCAGTGTTCCCCCTTGCCCCGAGCTCCAAGAGCACTTCG
GGCGGAACCGCTGCCCTGGGTTGCCTCGTGAAGGATTACTTCCCCGAGCCTGTGACCGTG
TCCTGGAACTCCGGGGCCTTGACCAGCGGAGTCCACACCTTCCCGGCCGTGCTGCAATCA
TCCGGTCTGTACAGTCTGTCCTCCGTGGTCACGGTGCCCTCGTCCTCACTGGGGACTCAG
ACTTACATCTGTAACGTGAACCATAAGCCATCGAACACCAAAGTCGACAAACGGGTGGAA
CCTAAGTCATGCGACAAGACCCACACGTGCCCACCTTGCCCCGCCCCGAGCTCCTGGGG
GGGCCGAGCGTGTTCCTCTTCCCGCCGAAACCGAAGGACACCCTGATGATCTCGAGGACT
CCTGAAGTCACTTGCGTGGTCGTGGACGTGTCGCACGAGGACCCCGAAGTCAAGTTCAAT
TGGTACGTGGACGGAGTCGAAGTGCACAACGCTAAGACCAAACCCCGCGAGGAGCAGTAC
GCAAGCACCTACCGCGTTGTCAGCGTGCTCACCGTGCTGCATCAGGATTGGCTGAATGGA
AAGGAGTACAAGTGCAAAGTGTCCAACAAGGCCCTGCCTGCACCAATTGAAAAGACCATC
TCCAAGGCCAAGGGCCAGCCCCGGGAGCCCCAAGTCTACACTCTGCCGCCGTCGAGAGAA
GAAATGACCAAGAACCAAGTGTCCCTGACTTGTCTGGTCAAGGGCTTCTATCCTTCGGAC
ATCGCGGTGGAATGGGAGAGCAACGGCCAGCCGGAGAACAATTACAAGACTACGCCACCC
GTGCTGGACTCTGACGGCTCCTTTTTCCTGTATTCCAAGCTCACCGTGGACAAGAGCCGC
TGGCAACAGGGAAACGTGTTCAGCTGCTCCGTGATGCACGAAGCCCTGCACAACCACTAC
ACCCAGAAGTCCCTGAGCTTGTCCCTGGT (SEQ ID NO:89)

HzCL25 light chain DNA sequence
GACATCGTGATGACCCAGTCCCCGGATTCACTCGCGGTGTCTTTGGGGGAGAGGGCAACC
ATTAACTGCAAGGCCTCACAGGATGTGTCCACTGCTGTCGCCTGGTACCAGCAGAAGCCT
GGGCAGCCGCCCAAGCTGCTGATCTACTCGGCCTCCTACCGCTATTCCGGAGTCCCCGAC
CGGTTCTCCGGCTCGGGTTCCGGAACTGATTTCACCCTGACAATTTCGTCGCTGCAAGCC
GAGGACGTGGCCGTGTACTACTGCCAACAGCATTACAACACTCCTTACACTTTTGGTGGC
GGAACTAAGCTCGAGATCAAGCGGACGGTGGCAGCTCCGTCAGTGTTCATCTTCCCTCCA
TCGGACGAACAGCTGAAGTCCGGCACCGCGTCCGTCGTGTGTCTGTTGAACAACTTCTAC
CCGCGGGAAGCCAAGGTCCAGTGGAAAGTCGACAACGCGCTGCAGTCCGGAAATAGCCAG
GAAAGCGTGACCGAACAGGACTCCAAGGACAGCACCTACTCCCTGAGCTCAACCCTGACC
CTGAGCAAGGCCGACTATGAGAAGCACAAAGTGTACGCCTGCGAAGTGACCCACCAAGGC
CTGAGCAGCCCAGTGACCAAGTCCTTCAACCGCGGGGAGTGT (SEQ ID NO:90)

FIG. 25B

3-F03_411 heavy chain DNA sequence
GAAGTGCAGTTGGTGGAGAGCGGGGGCGGACTGGTGCAGCCGGGGGGCTCGCTGCG
GCTGTCCTGCGCCGCGTCCGGTTTCACTTTTTCGAGCTACGACATGCACTGGGTCC
GCCAAGCACCGGGGAAGGGTCTGGAATGGGTGGCCGTGATGTCGTACGACGGCTCC
AACAAGTACTACGCCGACTCCGTGAAGGGACGGTTCACCATCTCCCGCGACAACAG
CAAGAACGCCCTTTACCTCCAAATGAACAGCCTGAGGGCCGAGGACACAGCCGTAT
ACTACTGCGCGACCGAGATCGCCGCCAAGGGGACTACTGGGGTCAAGGCACTCTG
GTCACCGTGTCCTCCGCCTCCACTAAGGGACCCTCAGTGTTCCCCCTTGCCCCGAG
CTCCAAGAGCACTTCGGGCGGAACCGCTGCCCTGGGTTGCCTCGTGAAGGATTACT
TCCCCGAGCCTGTGACCGTGTCCTGGAACTCCGGGGCCTTGACCAGCGGAGTCCAC
ACCTTCCCGGCCGTGCTGCAATCATCCGGTCTGTACAGTCTGTCCTCCGTGGTCAC
GGTGCCCTCGTCCTCACTGGGGACTCAGACTTACATCTGTAACGTGAACCATAAGC
CATCGAACACCAAAGTCGACAAACGGGTGGAACCTAAGTCATGCGACAAGACCCAC
ACGTGCCCACCTTGCCCCGCCCCGAGCTCCTGGGGGGCCGAGCGTGTTCCTCTT
CCCGCCGAAACCGAAGGACACCCTGATGATCTCGAGGACTCCTGAAGTCACTTGCG
TGGTCGTGGACGTGTCGCACGAGGACCCCGAAGTCAAGTTCAATTGGTACGTGGAC
GGAGTCGAAGTGCACAACGCTAAGACCAAACCCCGCGAGGAGCAGTACGCAAGCAC
CTACCGCGTTGTCAGCGTGCTCACCGTGCTGCATCAGGATTGGCTGAATGGAAAGG
AGTACAAGTGCAAAGTGTCCAACAAGGCCCTGCCTGCACCAATTGAAAAGACCATC
TCCAAGGCCAAGGGCCAGCCCCGGGAGCCCCAAGTCTACACTCTGCCGCCGTCGAG
AGAAGAAATGACCAAGAACCAAGTGTCCCTGACTTGTCTGGTCAAGGGCTTCTATC
CTTCGGACATCGCGGTGGAATGGGAGAGCAACGGCCAGCCGGAGAACAATTACAAG
ACTACGCCACCCGTGCTGGACTCTGACGGCTCCTTTTTCCTGTATTCCAAGCTCAC
CGTGGACAAGAGCCGCTGGCAACAGGGAAACGTGTTCAGCTGCTCCGTGATGCACG
AAGCCCTGCACAACCACTACACCCAGAAGTCCCTGAGCTTGTCCCTGGT (SEQ
ID NO:91)

FIG. 25C

3-F03_411 and 3-F03_413 light chain DNA sequence
ATCCAGATGACTCAGTCCCCTTCCTCGTTGTCCGCTTCCGTGGGTGATCGGGTCAC
AATCACTTGCCGGGCCAGCCAGGGAATTTCCAACTACCTCGCCTGGTACCAGCAGA
AGCCCGGAAAGGCACCGAAGCTGCTGATCTACGCCGCGTCCACTCTGCAATCCGGA
GTGCCTTCTCGGTTCTCGGGCTCGGGAAGCGGCACCGACTTTACCCTGACCATTAG
CAGCCTGCAGCCCGAGGACTTCGCAACCTACTACTGTCAGCAGTCCTACTCAACCC
CTCACTTCGGACAGGGTACTAGACTCGAGATCAAGAGGACTGTGGCCGCGCCGTCG
GTGTTCATCTTCCACCCTCGGACGAGCAGCTGAAGTCCGGCACCGCCAGCGTGGT
CTGCCTGCTGAACAACTTCTATCCGCGCGAAGCCAAGGTCCAGTGGAAAGTGGATA
ATGCGCTGCAGAGCGGGAACTCCCAAGAGTCCGTGACGGAACAGGACTCCAAAGAC
TCCACCTACTCACTGTCATCCACCCTGACCCTGTCAAAGGCCGACTACGAGAAGCA
TAAGGTCTACGCCTGCGAAGTGACCCACCAAGGGCTGAGCTCGCCCGTGACCAAGT
CCTTCAACCGGGGCGAATGC (SEQ ID NO:92)

3-F03_413 heavy chain DNA sequence
GAAGTGCAGTTGGTGGAGAGCGGGGGCGGACTGGTGCAGCCGGGGGGCTCGCTGCG
GCTGTCCTGCGCCGCGTCCGGTTTCACTTTTTCGAGCTACGACATGCACTGGGTCC
GCCAAGCACCGGGGAAGGGTCTGGAATGGGTGGCCGTGATGTCGTACGAAGGCTCC
AACAAGTACTACGCCGACTCCGTGAAGGGACGGTTCACCATCTCCCGCGACAACAG
CAAGAACGCCCTTTACCTCCAAATGAACAGCCTGAGGGCCGAGGACACAGCCGTAT
ACTACTGCGCGACCGAGATCGCCGCCAAGGGGGACTACTGGGGTCAAGGCACTCTG
GTCACCGTGTCCTCCGCCTCCACTAAGGGACCCTCAGTGTTCCCCCTTGCCCCGAG
CTCCAAGAGCACTTCGGGCGGAACCGCTGCCCTGGGTTGCCTCGTGAAGGATTACT
TCCCCGAGCCTGTGACCGTGTCCTGGAACTCCGGGGCCTTGACCAGCGGAGTCCAC
ACCTTCCCGGCCGTGCTGCAATCATCCGGTCTGTACAGTCTGTCCTCCGTGGTCAC
GGTGCCCTCGTCCTCACTGGGGACTCAGACTTACATCTGTAACGTGAACCATAAGC
CATCGAACACCAAAGTCGACAAACGGGTGGAACCTAAGTCATGCGACAAGACCCAC
ACGTGCCCACCTTGCCCCGCCCCGAGCTCCTGGGGGGCCGAGCGTGTTCCTCTT
CCCGCCGAAACCGAAGGACACCCTGATGATCTCGAGGACTCCTGAAGTCACTTGCG
TGGTCGTGGACGTGTCGCACGAGGACCCCGAAGTCAAGTTCAATTGGTACGTGGAC
GGAGTCGAAGTGCACAACGCTAAGACCAAACCCCGCGAGGAGCAGTACGCAAGCAC
CTACCGCGTTGTCAGCGTGCTCACCGTGCTGCATCAGGATTGGCTGAATGGAAAGG
AGTACAAGTGCAAAGTGTCCAACAAGGCCCTGCCTGCACCAATTGAAAAGACCATC
TCCAAGGCCAAGGGCCAGCCCCGGGAGCCCAAGTCTACACTCTGCCGCCGTCGAG
AGAAGAAATGACCAAGAACCAAGTGTCCCTGACTTGTCTGGTCAAGGCTTCTATC
CTTCGGACATCGCGGTGGAATGGGAGAGCAACGGCCAGCCGGAGAACAATTACAAG
ACTACGCCACCCGTGCTGGACTCTGACGGCTCCTTTTTCCTGTATTCCAAGCTCAC
CGTGGACAAGAGCCGCTGGCAACAGGGAAACGTGTTCAGCTGCTCCGTGATGCACG
AAGCCCTGCACAACCACTACACCCAGAAGTCCCTGAGCTTGTCCCTGGT (SEQ ID NO:93)

ial applications, filed Jan. 3, 2020, which is
ANTI-CD73 ANTIBODIES AND USES THEREOF

RELATED APPLICATIONS

This application claims the benefit of U.S. Provisional Application No. 62/956,847, filed Jan. 3, 2020, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 23, 2020, is named 20443-0644001_SL.txt and is 89,020 bytes in size.

BACKGROUND

Cluster of differentiation 73 (CD73) is a glycosyl phosphatidyl inositol- (GPI-) linked membrane protein that catalyzes the conversion of extracellular adenosine monophosphate (AMP) to adenosine. It functions as a homodimer, and can be shed and is active as a soluble protein in circulation. In addition to its enzymatic function, CD73 also is a cellular adhesion molecule and plays a role in regulation of leukocyte trafficking. CD73 levels are known to be upregulated due to tissue injury or hypoxic conditions, and a number of solid tumors have elevated CD73 levels. Upregulation of CD73 within the tumor contributes to the adenosine-rich tumor microenvironment, which has numerous pro-tumor and immuno-suppressive effects. Thus, there is a need for therapeutics targeting CD73 in cancer.

SUMMARY

In one aspect, the disclosure provides an antibody that binds to human CD73, wherein the antibody comprises a variable heavy (VH) domain comprising VH complementarity determining region (CDR)1, VH CDR2, and VH CDR3, wherein:
   the VH CDR1 comprises the amino acid sequence GYTFTSYG (SEQ ID NO:1);
   the VH CDR2 comprises the amino acid sequence IYPGSGNT (SEQ ID NO:2); and
   the VH CDR3 comprises the amino acid sequence ARYDYLGSSYGFDY (SEQ ID NO:3); and
wherein the antibody comprises a variable light (VL) domain comprising VL CDR1, VL CDR2, and VL CDR3, wherein:
   the VL CDR1 comprises the amino acid sequence QDVSTA (SEQ ID NO:4);
   the VL CDR2 comprises the amino acid sequence SAS (SEQ ID NO:5); and
   the VL CDR3 comprises the amino acid sequence QQHYNTPYT (SEQ ID NO:6).

In some embodiments of the first aspect, the VH domain comprises the amino acid sequence set forth in SEQ ID NO:22.

In some embodiments of the first aspect, the antibody comprises a heavy chain and wherein the heavy chain comprises the amino acid sequence set forth in SEQ ID NO:24.

In some embodiments of the first aspect, the VL domain comprises the amino acid sequence set forth in SEQ ID NO:23.

In some embodiments of the first aspect, the antibody comprises a light chain and wherein the light chain comprises the amino acid sequence set forth in SEQ ID NO:25.

In some embodiments of the first aspect, the VH domain is at least 80% identical to the amino acid sequence set forth in SEQ ID NO:22 and the VL domain is at least 80% identical to the amino acid sequence set forth in SEQ ID NO:23.

In some embodiments of the first aspect, the VH domain comprises the amino acid sequence set forth in SEQ ID NO:22 and the VL domain comprises the amino acid sequence set forth in SEQ ID NO:23.

In some embodiments of the first aspect, the antibody comprises a heavy chain and a light chain, and wherein the heavy chain comprises the amino acid sequence set forth in SEQ ID NO:24 and the light chain comprises the amino acid sequence set forth in SEQ ID NO:25.

In a second aspect, the disclosure provides an antibody that binds to human CD73, wherein the antibody binds to human CD73 at an epitope within amino acids 40-53 of SEQ ID NO:70.

In a third aspect, the disclosure provides an antibody that binds to human CD73 and competes for binding to human CD73 with an antibody that has a heavy chain comprising the amino acid sequence of SEQ ID NO:24 and a light chain comprising the amino acid sequence of SEQ ID NO:25.

In some embodiments of the first, second, and third aspects, the antibody is a humanized antibody.

In some embodiments of the first, second, and third aspects, the antibody is a bispecific antibody, single chain antibody, an Fab fragment, an F(ab')2 fragment, an Fab' fragment, an Fsc fragment, an Fv fragment, an scFv, an sc(Fv)2, or a diabody.

In a fourth aspect, the disclosure provides a nucleic acid or nucleic acids encoding the antibody of any one of the first through third aspects.

In a fifth aspect, the disclosure provides an expression vector or expression vectors comprising the foregoing nucleic acid or nucleic acids of the fourth aspect.

In a sixth aspect, the disclosure provides an isolated cell comprising the nucleic acid or nucleic acids of the fourth aspect or the expression vector or expression vectors of the fifth aspect.

In a seventh aspect, the disclosure provides an isolated cell comprising a first expression vector comprising a first nucleic acid encoding a first polypeptide comprising the VH domain of the antibody of any one of the first through third aspects operably linked to a promoter, and a second expression vector comprising a second nucleic acid encoding a second polypeptide comprising the VL domain of the antibody of any one of the first through third aspects operably linked to a promoter.

In an eighth aspect, the disclosure provides an isolated cell that produces the antibody of any one of the first through third aspects.

In a ninth aspect, the disclosure provides a method of making the antibody of any one of the first through third aspects, comprising culturing the cell of the sixth or seventh aspect and isolating the antibody.

In a tenth aspect, the disclosure provides a pharmaceutical composition comprising the antibody of any one of the first through third aspects and a pharmaceutically acceptable carrier.

In an eleventh aspect, the disclosure provides a method for treating a cancer in a human subject in need thereof, comprising administering to the human subject an effective amount of the antibody of any one of the first through third aspects.

In some embodiments of the eleventh aspect, the cancer has a high adenosine signature.

In some embodiments of the eleventh aspect, the cancer is head and neck cancer, colorectal cancer, lung cancer, melanoma, ovarian, bladder, liver cancer, or renal cell carcinoma.

In a twelfth aspect, the disclosure provides an antibody that binds to human CD73, wherein the antibody comprises a variable heavy (VH) domain comprising VH complementarity determining region (CDR)1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATE-IAAKGDY (SEQ ID NO:36); and
wherein the antibody comprises a variable light (VL) domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and the VL CDR3 comprises the amino acid sequence QQSYSTPH (SEQ ID NO:39).

In some embodiments of the twelfth aspect,
the VH CDR1 comprises the amino acid sequence GFTFSSYD (SEQ ID NO:34);
the VH CDR2 comprises the amino acid sequence MSYDGSNK (SEQ ID NO:35);
the VH CDR3 comprises the amino acid sequence ATE-IAAKGDY (SEQ ID NO:36);
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39). In some embodiments, the VH domain comprises the amino acid sequence set forth in SEQ ID NO:62. In some embodiments, the antibody comprises a heavy chain and wherein the heavy chain comprises the amino acid sequence set forth in SEQ ID NO:30. In some embodiments, the VL domain comprises the amino acid sequence set forth in SEQ ID NO:61. In some embodiments, the antibody comprises a light chain and wherein the light chain comprises the amino acid sequence set forth in SEQ ID NO:31. In some embodiments, the VH domain is at least 80% identical to the amino acid sequence set forth in SEQ ID NO:62 and the VL domain is at least 80% identical to the amino acid sequence set forth in SEQ ID NO:61. In some embodiments, the VH domain comprises the amino acid sequence set forth in SEQ ID NO:62 and the VL domain comprises the amino acid sequence set forth in SEQ ID NO:61. In some embodiments, the antibody comprises a heavy chain and a light chain, and wherein the heavy chain comprises the amino acid sequence set forth in SEQ ID NO:30 and the light chain comprises the amino acid sequence set forth in SEQ ID NO:31.

In some embodiments of the twelfth aspect,
the VH CDR1 comprises the amino acid sequence GFTFSSYD (SEQ ID NO:34);
the VH CDR2 comprises the amino acid sequence MSYEGSNK (SEQ ID NO:40);
the VH CDR3 comprises the amino acid sequence ATE-IAAKGDY (SEQ ID NO:36);
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39). In some embodiments, the VH domain comprises the amino acid sequence set forth in SEQ ID NO:63. In some embodiments, the antibody comprises a heavy chain and wherein the heavy chain comprises the amino acid sequence set forth in SEQ ID NO:33. In some embodiments, the VL domain comprises the amino acid sequence set forth in SEQ ID NO:61. In some embodiments, the antibody comprises a light chain and wherein the light chain comprises the amino acid sequence set forth in SEQ ID NO:31. In some embodiments, the VH domain is at least 80% identical to the amino acid sequence set forth in SEQ ID NO:63 and the VL domain is at least 80% identical to the amino acid sequence set forth in SEQ ID NO:61. In some embodiments, the VH domain comprises the amino acid sequence set forth in SEQ ID NO:63 and the VL domain comprises the amino acid sequence set forth in SEQ ID NO:61. In some embodiments, the antibody comprises a heavy chain and a light chain, and wherein the heavy chain comprises the amino acid sequence set forth in SEQ ID NO:33 and the light chain comprises the amino acid sequence set forth in SEQ ID NO:31.

In a thirteenth aspect, the disclosure provides an antibody that binds to human CD73, wherein the antibody binds to human CD73 at an epitope within amino acids 386-399 and 470-489 of SEQ ID NO:70.

In a fourteenth aspect, the disclosure provides an antibody that binds to human CD73 and competes for binding to human CD73 with an antibody that has a heavy chain comprising the amino acid sequence of SEQ ID NO:30 and a light chain comprising the amino acid sequence of SEQ ID NO:31.

In a fifteenth aspect, the disclosure provides an antibody that binds to human CD73 and competes for binding to human CD73 with an antibody that has a heavy chain comprising the amino acid sequence of SEQ ID NO:33 and a light chain comprising the amino acid sequence of SEQ ID NO:31.

In some embodiments of the twelfth through fifteenth aspects, the antibody is a humanized antibody.

In some embodiments of the twelfth through fifteenth aspects, the antibody is a bispecific antibody, single chain antibody, an Fab fragment, an F(ab')2 fragment, an Fab' fragment, an Fsc fragment, an Fv fragment, an scFv, an sc(Fv)2, or a diabody.

In a sixteenth aspect, the disclosure provides a nucleic acid or nucleic acids encoding the antibody thereof of any one of the twelfth through fifteenth aspects.

In a seventeenth aspect, the disclosure provides an expression vector or expression vectors comprising the nucleic acid or nucleic acids of the sixteenth aspect operably linked to a promoter.

In an eighteenth aspect, the disclosure provides an isolated cell comprising the nucleic acid or nucleic acids of the sixteenth aspect or the expression vector or expression vectors of the seventeenth aspect.

In a nineteenth aspect, the disclosure provides an isolated cell comprising a first expression vector comprising a first nucleic acid encoding a first polypeptide comprising the VH domain of the antibody of any one of the twelfth through fifteenth aspects operably linked to a promoter, and a second expression vector comprising a second nucleic acid encoding a second polypeptide comprising the VL domain of the antibody of any one of the twelfth through fifteenth aspects operably linked to a promoter.

In a twentieth aspect, the disclosure provides an isolated cell that produces the antibody of any one of the twelfth through fifteenth aspects.

In a twenty-first aspect, the disclosure provides a method of making the antibody of any one of the twelfth through fifteenth aspects, comprising culturing the cell of the eighteenth or nineteenth aspect and isolating the antibody.

In a twenty-second aspect, the disclosure provides a pharmaceutical composition comprising the antibody of any one of the twelfth through fifteenth aspects and a pharmaceutically acceptable carrier.

In a twenty-third aspect, the disclosure provides a method for treating a cancer in a human subject in need thereof, comprising administering to the human subject an effective amount of the antibody of any one of the twelfth through fifteenth aspects.

In some embodiments of the twenty-third aspect, the cancer has a high adenosine signature. In some embodiments of the twenty-third aspect, the cancer is head and neck cancer, colorectal cancer, lung cancer, melanoma, ovarian, bladder, liver cancer, or renal cell carcinoma.

BRIEF DESCRIPTION OF THE DRAWINGS

FIG. 1A shows the heavy chain variable domain (VH) and light chain variable domain (VL) amino acid sequences for humanized CL25 antibodies CL_hu10-4, HzCL25, CL25_hu_10-6, and CL25_hu_11-4.

FIG. 1B shows the VH and VL amino acid sequences for humanized CL25 antibodies CL25_hu_11-5, CL25_hu_11-6, CL25_hu_8-4, and CL25_hu_8-5.

FIG. 1C shows the VH and VL amino acid sequences for humanized CL25 antibodies CL25_hu_8-6, CL25_hu_9-4, CL25_hu_9-5, and CL25_hu_9-6.

FIG. 1D shows an alignment of the VH for CL25 and humanized CL25 antibodies. CDRs according to the IMGT definition are underlined.

FIG. 1E shows an alignment of the VL for CL25 and humanized CL25 antibodies. CDRs according to the IMGT definition are underlined.

FIG. 12 are graphs depicting the concentration of total and free soluble hCD73 in sera of mice treated with the indicated antibody or IgG isotype control. Total soluble hCD73 was detected with non-competing antibody (Antibody X, bottom) and free soluble hCD73 was detected with competing antibody (HzCL25, top).

FIG. 20 are graphs depicting the concentration of total and free soluble hCD73 in sera of mice treated with 3-F03 or IgG isotype control. Total soluble hCD73 was detected with non-competing antibody (Antibody X, top) and free soluble hCD73 was detected with competing antibody (3-F03, bottom).

FIG. 21A-FIG. 21J show the VH and VL amino acid sequences of 3-F03 and exemplary 3-F03 variants.

FIG. 24 shows exemplary amino acid sequences of a human IgG1 heavy chain CH1-hinge-CH2-CH3 with an N297A mutation (SEQ ID NO:73), a human IgG1 heavy chain CH1-hinge-CH2-CH3 with an N297A mutation with C-terminal lysine (SEQ ID NO:75), and a human kappa light chain constant region (SEQ ID NO:74).

FIG. 25A shows the DNA sequences encoding the HzCL25 heavy chain and light chain.

FIG. 25B shows the DNA sequence encoding the 3-F03_411 heavy chain.

FIG. 25C shows the DNA sequences encoding the 3-F03_411 and 3-F03_413 light chain and 3-F03_413 heavy chain.

DETAILED DESCRIPTION

Figure 2A:
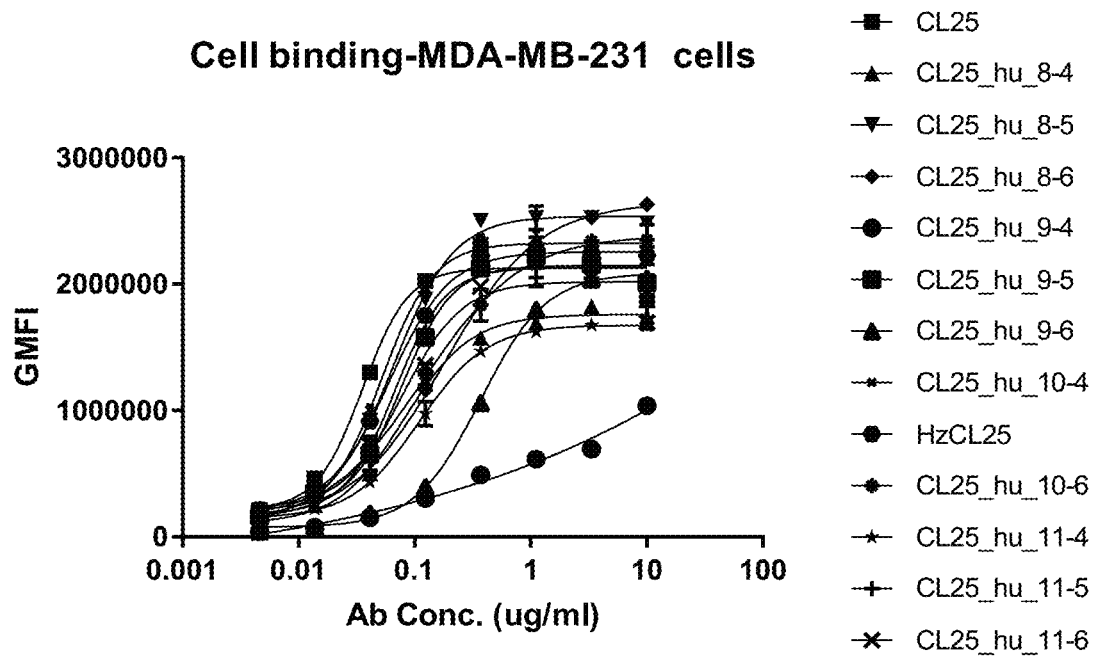
FIG. 2A is a graph depicting the cell binding (measured by geometric mean fluorescence intensity [GMFI]) for the indicated antibodies at the indicated concentrations on MDA-MB-231 cells.

Provided herein are anti-CD73 antibodies and related nucleic acids, expression vectors, cells, and pharmaceutical compositions. The anti-CD73 antibodies described herein are useful in the treatment or prevention of disorders such as cancer (e.g., head and neck cancer, colorectal cancer, lung cancer, melanoma, ovarian, bladder, liver cancer, or renal cell carcinoma).

CD73

CD73 (also known as "5'-nucleotidase" and "ecto-5'-nucleotidase") is a dimeric enzyme (EC:3.1.3.5) that functions as a homodimer bound by a GPI linkage to the external face of the plasma membrane. CD73 can be shed and is active as a soluble protein in circulation. CD73 catalyzes the conversion of extracellular AMP to adenosine. CD73 enzymatic activity requires substrate binding in the open CD73 conformation. After the substrate binding, CD73 goes through a large conformational change from open to closed conformation to convert AMP to adenosine (see, e.g., Knapp et al., 2012, Structure, 20(12):2161-73). CD73 also functions as a cellular adhesion molecule and plays a role in regulation of leukocyte trafficking.

CD73 enzymatic activity plays a role in the promotion and metastasis of cancer (see, e.g., Stagg and Smyth, 2010, Oncogene, 29:5346-5358; Salmi and Jalkanen, 2012, OncoImmunology, 1:247-248, 2012; Stagg, 2012, OncoImmunology, 1:217-218; Zhang, 2012, OncoImmunology, 167-70). Overexpression of CD73 in cancer cells impairs adaptive antitumor immune responses, enhancing tumor growth and metastasis (see, e.g., Niemela et al., 2004, J. Immunol., 172:1646-1653; Sadej et al., 2006, Nucleosides Nucleotides Nucleic Acids, 25:1119-1123; Braganhol et al., 2007, Biochim. Biophys. Acta., 1770:1352-1359; Zhang, 2010, Cancer Res., 70:6407-6411; Zhang, 2012, OncoImmunology, 1:67-70).

An exemplary amino acid sequence of the mature human CD73 protein (amino acids 27-549 of GenBank Accession No. NP_002517) is:

```
                                            (SEQ ID NO: 70)
WELTILHTNDVHSRLEQTSEDSSKCVNASRCMGGVARLFTKVQQIRRAEP

NVLLLDAGDQYQGTIWFTVYKGAEVAHFMNALRYDAMALGNHEFDNGVEG

LIEPLLKEAKFPILSANIKAKGPLASQISGLYLPYKVLPVGDEVVGIVGY

TSKETPFLSNPGTNLVFEDEITALQPEVDKLKTLNVNKIIALGHSGFEMD

KLIAQKVRGVDVVVGGHSNTFLYTGNPPSKEVPAGKYPFIVTSDDGRKVP

VVQAYAFGKYLGYLKIEFDERGNVISSHGNPILLNSSIPEDPSIKADINK

WRIKLDNYSTQELGKTIVYLDGSSQSCRFRECNMGNLICDAMINNNLRHT

DEMFWNHVSMCILNGGGIRSPIDERNNGTITWENLAAVLPFGGTFDLVQL

KGSTLKKAFEHSVHRYGQSTGEFLQVGGIHVVYDLSRKPGDRVVKLDVLC

TKCRVPSYDPLKMDEVYKVILPNFLANGGDGFQMIKDELLRHDSGDQDIN

VVSTYISKMKVIYPAVEGRIKFS.
```

An exemplary amino acid sequence of the mature murine CD73 protein (amino acids 29-551 of GenBank Accession No. NP 035981) is:

```
                                            (SEQ ID NO: 71)
WELTILHTNDVHSRLEQTSDDSTKCLNASLCVGGVARLFTKVQQIRKEEP

NVLFLDAGDQYQGTIWFTVYKGLEVAHFMNILGYDAMALGNHEFDNGVEG

LIDPLLRNVKFPILSANIKARGPLAHQISGLFLPSKVLSVGGEVVGIVGY

TSKETPFLSNPGTNLVFEDEISALQPEVDKLKTLNVNKIIALGHSGFEMD

KLIAQKVRGVDIVVGGHSNTFLYTGNPPSKEVPAGKYPFIVTADDGRQVP

VVQAYAFGKYLGYLKVEFDDKGNVITSYGNPILLNSSIPEDATIKADINQ

WRIKLDNYSTQELGRTIVYLDGSTQTCRFRECNMGNLICDAMINNNLRHP

DEMFWNHVSMCIVNGGGIRSPIDEKNNGTITWENLAAVLPFGGTFDLVQL

KGSTLKKAFEHSVHRYGQSTGEFLQVGGIHVVYDINRKPWNRVVQLEVLC

TKCRVPIYEPLEMDKVYKVTLPSYLANGGDGFQMIKDELLKHDSGDQDIS

VVSEYISKMKVVYPAVEGRIKFS.
```

An exemplary amino acid sequence of the mature cynomolgus CD73 protein is:

(SEQ ID NO: 72)
WELTILHTNDVHSRLEQTSEDSSKCVNASRCMGGVARLFTKVQQIRRAEP

NVLLLDAGDQYQGTIWFTVYKGAEVAHFMNALRYDAMALGNHEFDNGVEG

LIEPLLKEAKFPILSANIKAKGPLASQISGLYLPYKVLPVGDEVVGIVGY

TSKETPFLSNPGTNLVFEDEITALQPEVDKLKTLNVNKIIALGHSGFETD

KLIAQKVRGVDVVVGGHSNTFLYTGNPPSKEVPAGKYPFIVTSDDGRKVP

VVQAYAFGKYLGYLKIEFDERGNVISSHGNPILLNSSIPEDPSIKADINK

WRIKLDNYSTQELGKTIVYLDGSSQSCRFRECNMGNLICDAMINNNLRHA

DEMFWNHVSMCILNGGGIRSPIDERNNGTITWENLAAVLPFGGTFDLVQL

KGSTLKKAFEHSVHRYGQSTGEFLQVGGIHVVYDLSRKPGDRVVKLDVLC

TKCRVPSYDPLKMDEIYKVILPNFLANGGDGFQMIKDELLRHDSGDQDIN

VVSTYISKMKVIYPAVEGRIKFS.

Anti-CD73 Antibodies

This disclosure provides anti-CD73 antibodies that are useful in treating cancer. These antibodies can bind human CD73.

In some instances, these antibodies bind human CD73 and cynomolgus CD73. In some instances, these antibodies bind human CD73 and cynomolgus CD73 and do not bind murine CD73. Such anti-CD73 antibodies include the sequences of an anti-CD73 monoclonal antibody, CL25, and a humanized version thereof, HzCL25, which humanized version thereof binds with high affinity to both human and cynomolgus CD73 (e.g., less than approximately 0.5 nM in the open conformations for both human and cynomolgus CD73), and has undetectable binding to mouse CD73.

In some instances, these antibodies bind human CD73, cynomolgus CD73, and murine CD73. Such anti-CD73 antibodies includes the sequences of a human anti-CD73 monoclonal antibody, 3-F03, which binds with high affinity to the open conformation of each of human, cynomolgus, and murine CD73 (e.g., approximately 0.37 nM for human CD73, approximately 0.734 nM for cynomolgus CD73, and approximately 1.66 nM for murine CD73). Such anti-CD73 antibodies have undetectable binding to the closed conformation of each of human, cynomolgus, and murine CD73, in the presence of an excess of a non-cleavable CD73 ligand, APCP.

Antibody HzCL25

Antibody HzCL25 is a humanized IgG1/kappa monoclonal antibody with alanine at position Asparagine-297 (N297, according to EU numbering) of the heavy chain constant region to reduce effector function. It specifically binds human and cynomolgus CD73 with high affinity ($K_D \leq 0.5$ nM) and has low effector functionality.

HzCL25 was constructed from a chimeric version of the CL25 antibody. The CL25 murine heavy chain variable domain (VH) and light chain variable domain (VL) were obtained from a mouse immunized with recombinant human CD73 (SEQ ID NO:70) comprising a HIS-tag. Antibody sequences of the B cells were determined and the murine heavy chain variable domain (VH) (SEQ ID NO:26) and light chain variable domain (VL) (SEQ ID NO:27) were expressed as chimeras with human IgG1 Fc (heavy chain constant region comprising the amino acid sequence of SEQ ID NO:73 and kappa light chain constant region comprising the amino acid sequence of SEQ ID NO:74). Table 1, below, shows the amino acid sequences of the CL25 complementarity determining regions (CDRs) according to IMGT, Chothia, AbM, Kabat, and Contact numbering. Table 1, below, also shows the amino acid sequences of the CL25 mature VH and VL.

TABLE 1

CL25 CDRs, VH, and VL

| | IMGT | Chothia | AbM | Kabat | Contact |
|---|---|---|---|---|---|
| VH CDR1 | GYTFTSYG (SEQ ID NO: 1) | GYTFTSY (SEQ ID NO: 7) | GYTFTSYGLS (SEQ ID NO: 12) | SYGLS (SEQ ID NO: 14) | TSYGLS (SEQ ID NO: 16) |
| VH CDR2 | IYPGSGNT (SEQ ID NO: 2) | YPGSGN (SEQ ID NO: 8) | EIYPGSGNTY (SEQ ID NO: 13) | EIYPGSGNTYY NEKFKG (SEQ ID NO: 15) | WIGEIYPGSGNTY (SEQ ID NO: 28) |
| VH CDR3 | ARYDYLGSSYGFDY (SEQ ID NO: 3) | YDYLGSSYGFDY (SEQ ID NO: 9) | YDYLGSSYGFDY (SEQ ID NO: 9) | YDYLGSSYGFDY (SEQ ID NO: 9) | ARYDYLGSSYGFD (SEQ ID NO: 18) |
| VL CDR1 | QDVSTA (SEQ ID NO: 4) | KASQDVSTAVA (SEQ ID NO: 10) | KASQDVSTAVA (SEQ ID NO: 10) | KASQDVSTAVA (SEQ ID NO: 10) | STAVAWY (SEQ ID NO: 19) |
| VL CDR2 | SAS (SEQ ID NO: 5) | SASYRYN (SEQ ID NO: 29) | SASYRYN (SEQ ID NO: 29) | SASYRYN (SEQ ID NO: 29) | LLIYSASYRY (SEQ ID NO: 20) |
| VL CDR3 | QQHYNTPYT (SEQ ID NO: 6) | QQHYNTPYT (SEQ ID NO: 6) | QQHYNTPYT (SEQ ID NO: 6) | QQHYNTPYT (SEQ ID NO: 6) | QQHYNTPY (SEQ ID NO: 21) |
| VH | QVQLQQSGAELARPGASVKLSCRASGYTFTSYGLSWVKQRTGQGLEWIGEIYPGSGNTYYNEKFKGKATLTAD KSSSTAYMELRSLTSEDSAVYFCARYDYLGSSYGFDYWGQGTTLTVSS (SEQ ID NO: 26) | | | | |
| VL | DIVMTQSHKFMSTSVGDRVSITCKASQDVSTAVAWYQQKPGQSPKLLIYSASYRYNGVPDRFTGSGSGTDFTF TISSVQAEDLAVYYCQQHYNTPYTFGGGTKLEIK (SEQ ID NO: 27) | | | | |

To construct HzCL25, the CL25 VH and VL sequences were aligned to a database of human VH and VK genes. The CDRs (Table 1) from the murine CL25 antibody were grafted into human VH and VK genes.

Table 2, below, shows the amino acid sequences of the HzCL25 CDRs according to IMGT, Chothia, AbM, Kabat, and Contact numbering. Table 2, below, also shows the amino acid sequences of the HzCL25 mature VH, VL, heavy chain, and light chain.

TABLE 2

Amino acid sequences of HzCL25 CDRs, VH, VL, heavy chain, and light chain

|  | IMGT | Chothia | AbM | Kabat | Contact |
|---|---|---|---|---|---|
| VH CDR1 | GYTFTSYG (SEQ ID NO: 1) | GYTFTSY (SEQ ID NO: 7) | GYTFTSYGLS (SEQ ID NO: 12) | SYGLS (SEQ ID NO: 14) | TSYGLS (SEQ ID NO: 16) |
| VH CDR2 | IYPGSGNT (SEQ ID NO: 2) | YPGSGN (SEQ ID NO: 8) | EIYPGSGNTY (SEQ ID NO: 13) | EIYPGSGNTYY NEKFKG (SEQ ID NO: 15) | WMGEIYPGSGNTY (SEQ ID NO: 17) |
| VH CDR3 | ARYDYLGSSYGFDY (SEQ ID NO: 3) | YDYLGSSYGFDY (SEQ ID NO: 9) | YDYLGSSYGFDY (SEQ ID NO: 9) | YDYLGSSYGFDY (SEQ ID NO: 9) | ARYDYLGSSYGFD (SEQ ID NO: 18) |
| VL CDR1 | QDVSTA (SEQ ID NO: 4) | KASQDVSTAVA (SEQ ID NO: 10) | KASQDVSTAVA (SEQ ID NO: 10) | KASQDVSTAVA (SEQ ID NO: 10) | STAVAWY (SEQ ID NO: 19) |
| VL CDR2 | SAS (SEQ ID NO: 5) | SASYRYS (SEQ ID NO: 11) | SASYRYS (SEQ ID NO: 11) | SASYRYS (SEQ ID NO: 11) | LLIYSASYRY (SEQ ID NO: 20) |
| VL CDR3 | QQHYNTPYT (SEQ ID NO: 6) | QQHYNTPYT (SEQ ID NO: 6) | QQHYNTPYT (SEQ ID NO: 6) | QQHYNTPYT (SEQ ID NO: 6) | QQHYNTPY (SEQ ID NO: 21) |
| VH | EVQLVQSGAEVKKPGESLKISCKGSGYTFTSYGLSWVRQMPGKGLEWMGEIYPGSGNTYYN EKFKGQVTISADKSISTAYLQWSSLKASDTAMYYCARYDYLGSSYGFDYWGAGTTVTVSS (SEQ ID NO: 22) | | | | |
| VL | DIVMTQSPDSLAVSLGERATINCKASQDVSTAVAWYQQKPGQPPKLLIYSASYRYSGVPDRFS GSGSGTDFTLTISSLQAEDVAVYYCQQHYNTPYTFGGGTKLEIK (SEQ ID NO: 23) | | | | |
| Heavy Chain | EVQLVQSGAEVKKPGESLKISCKGSGYTFTSYGLSWVRQMPGKGLEWMGEIYPGSGNTYYN EKFKGQVTISADKSISTAYLQWSSLKASDTAMYYCARYDYLGSSYGFDYWGAGTTVTVSSA STKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKRVEPKSCDKTHTCPPCPAPELLGGPSVFLFPP KPKDTLMISRTPEVTCVVVDVSHEDPEVKFNWYVDGVEVHNAKTKPREEQYASTYRVVSVL TVLHQDWLNGKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQGNVFSCSVMHE ALHNHYTQKSLSLSPG (SEQ ID NO: 24) | | | | |
| Light Chain | DIVMTQSPDSLAVSLGERATINCKASQDVSTAVAWYQQKPGQPPKLLIYSASYRYSGVPDRFS GSGSGTDFTLTISSLQAEDVAVYYCQQHYNTPYTFGGGTKLEIKRTVAAPSVFIFPPSDEQLKS GTASVVCLLNNFYPREAKVQWKVDNALQSGNSQESVTEQDSKDSTYSLSSTLTLSKADYEK HKVYACEVTHQGLSSPVTKSFNRGEC (SEQ ID NO: 25) | | | | |

The anti-CD73 antibodies can encompass the VH CDR1, VH CDR2, and VH CDR3 and the VL CDR1, VL CDR2, and VL CDR3 of HzCL25 or CL25. In some instances, the anti-CD73 antibody comprises a VH comprising VH CDR1, VH CDR2, and VH CDR3 of HzCL25 (see Table 2). In some instances, the anti-CD73 antibody comprises a VL comprising VL CDR1, VL CDR2, and VL CDR3 of HzCL25 (see Table 2). In some instances, the anti-CD73 antibody comprises a VH comprising VH CDR1, VH CDR2, and VH CDR3 of HzCL25 (see Table 2) and a VL comprising VL CDR1, VL CDR2, and VL CDR3 of HzCL25 (see Table 2). In some instances, the anti-CD73 antibody comprises a VH comprising VH CDR1, VH CDR2, and VH CDR3 of CL25 (see Table 1). In some instances, the anti-CD73 antibody comprises a VL comprising VL CDR1, VL CDR2, and VL CDR3 of CL25 (see Table 1). In some instances, the anti-CD73 antibody comprises a VH comprising VH CDR1, VH CDR2, and VH CDR3 of CL25 (see Table 1) and a VL comprising VL CDR1, VL CDR2, and VL CDR3 of CL25 (see Table 1). In some instances, the anti-CD73 antibodies can have, e.g., 1, 2, or 3 substitutions within one or more (i.e., 1, 2, 3, 4, 5, or 6) of the six CDRs of HzCL25 or CL25. In some instances, the antibodies (i) inhibit cellular CD73 (e.g., at least 10%; at least 20%; at least 30%; at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 3); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 4); and/or (iii) bind human or cynomolgus monkey CD73 in the open conformation with high affinity (e.g., $K_D \leq 0.5$ nM) but do not significantly bind CD73 in the open conformation from mice (e.g., as determined by the binding assay described in Example 6); and/or (iv) bind human or cynomolgus monkey CD73 in the closed conformation with high affinity (e.g., $K_D \leq 0.5$ nM) but do not significantly bind CD73 in the closed conformation from mice; and/or (v) bind to an epitope within amino acids 40-53 of SEQ ID NO:70 (i.e., within TKVQQIRRAEPNVL (SEQ ID NO:76)) (e.g., as determined by the binding assay described in Example 6); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 5); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 8); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 9); and/or (ix) reduce free surface CD73 on cells (e.g., cancer cells, e.g., melanoma cancer cancers, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 11).

The anti-CD73 antibodies can comprise the VH CDR1, VH CDR2, and VH CDR3 of HzCL25 or CL25 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VH CDR1 and/or VH CDR2 and/or VH CDR3 of HzCL25 or CL25. In some embodiments, the anti-CD73 antibodies further comprise the VL CDR1, VL CDR2, and VL CDR3 of HzCL25 or CL25 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VL CDR1 and/or VL CDR2 and/or VL CDR3 of HzCL25 or CL25. In some instances, the anti-CD73 antibody comprises a VH comprising the VH CDR1, VH CDR2, and VH CDR3 set forth in SEQ ID NOs: 1, 2, and 3, respectively, and a VL comprising the VL CDR1, VL CDR2, and VL CDR3 set forth in SEQ ID NOs: 4, 5, and 6, respectively. In some instances, the anti-CD73 antibody comprises a VH comprising the VH CDR1, VH CDR2, and VH CDR3 set forth in SEQ ID NOs: 7, 8, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 12, 13, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 14, 15, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 16, 17, and 18, respectively, and a VL comprising the VL CDR1, VL CDR2, and VL CDR3 set forth in SEQ ID NOs: 19, 20, and 21, respectively. In some instances, the anti-CD73 antibody comprises a VH comprising the VH CDR1, VH CDR2, and VH CDR3 set forth in SEQ ID NOs: 7, 8, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 12, 13, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 14, 15, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 16, 28, and 18, respectively, and a VL comprising the VL CDR1, VL CDR2, and VL CDR3 set forth in SEQ ID NOs: 19, 20, and 21, respectively. In some instances these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 3); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 4); and/or (iii) bind human or cynomolgus monkey CD73 in the open conformation with high affinity (e.g., $K_D \leq 0.5$ nM) but do not significantly bind CD73 in the open conformation from mice (e.g., as determined by the binding assay described in Example 6); and/or (iv) bind human or cynomolgus monkey CD73 in the closed conformation with high affinity (e.g., $K_D \leq 0.5$ nM) but do not significantly bind CD73 in the closed conformation from mice; and/or (v) bind to an epitope within amino acids 40-53 of SEQ ID NO:70 (i.e., within TKVQQIRRAEPNVL (SEQ ID NO:76)) (e.g., as determined by the binding assay described in Example 6); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 5); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 8); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 9); and/or (ix) reduce free surface CD73 on cells (e.g., cancer cells, e.g., melanoma cancer cancers, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 11).

In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In some embodiments, the anti-CD73 antibodies comprise a heavy chain comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some embodiments, the anti-CD73 antibodies comprise a light chain comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In certain embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs:24; and (ii) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs:25. In some embodiments, the anti-CD73 antibodies comprise: (i) a heavy chain comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24; and (ii) a light chain comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84. In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81. In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84 and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in SEQ ID NO: 23, 27, 80, and 81. In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84, and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22). In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22). In certain embodiments, the anti-CD73 antibodies comprise a VH comprising the amino acid sequence set forth in SEQ ID NO:22. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24). In some embodiments, the anti-CD73 antibodies comprise a heavy chain comprising a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24). In certain embodiments, the anti-CD73 antibodies comprise a heavy chain comprising the amino acid sequence set forth in SEQ ID NO:24. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise a VL comprising the amino acid sequence set forth in SEQ ID NO:23. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise a light chain comprising a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In certain embodiments, the anti-CD73 antibodies comprise a light chain comprising the amino acid sequence set forth in SEQ ID NO:25. In certain embodiments, the anti-CD73 antibodies comprise: (i) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22); and (ii) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22), and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise: a VH comprising the amino acid sequence set forth in SEQ ID NO:22, and (ii) a VL comprising the amino acid sequence set forth in SEQ ID NO:23. In some embodiments, the anti-CD73 antibodies comprise: (i) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24); and (ii) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise: (i) a heavy chain comprising a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24), and (ii) a light chain comprising a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise: (i) a heavy chain comprising the amino acid sequence set forth in SEQ ID NO:24, and (ii) a light chain comprising the amino acid sequence set forth in SEQ ID NO:25.

The CD73-binding epitope of HzCL25 is within the amino acid sequence TKVQQIRRAEPNVL (SEQ ID NO:76) (i.e., amino acids 40-53 of the amino acid sequence set forth in SEQ ID NO:70). This disclosure features antibodies that bind to CD73 within the sequence TKVQQIRRAEPNVL (SEQ ID NO:76). This disclosure features antibodies that bind to the same epitope as HzCL25. This disclosure also features antibodies that competitively inhibit binding of HzCL25 to human CD73.

In some embodiments, the VH of HzCL25 is linked to a heavy chain constant region comprising a CH1 domain and a hinge region. In some embodiments, the VH of HzCL25 is linked to a heavy chain constant region comprising a CH3 domain. In some embodiments, the CH3 domain lacks the C-terminal lysine (K) amino acid residue. In some embodiments, the CH3 domain contains the C-terminal lysine (K) amino acid residue. In certain embodiments, the VH of HzCL25 is linked to a heavy chain constant region comprising a CH1 domain, hinge region, CH2 domain, and CH3 domain from human IgG1. In some embodiments, the CH3 domain from human IgG1 lacks the C-terminal lysine (K) amino acid residue. In some embodiments, the CH3 domain from human IgG1 contains the C-terminal lysine (K) amino acid residue. In certain embodiments such an antibody contains one or more additional mutations in the heavy chain constant region that increase the stability of the antibody. In certain embodiments, the heavy chain constant region includes substitutions that modify the properties of the antibody (e.g., decrease Fc receptor binding, increase or decrease antibody glycosylation, decrease binding to C1q). In certain embodiments, the heavy chain constant region includes an alanine at position Asparagine-297 (N297, according to EU numbering) of the heavy chain constant region to reduce effector function.

In certain embodiments, the anti-CD73 antibody is an IgG antibody. In one embodiment, the antibody is an IgG1 antibody. In one embodiment, the antibody is an IgG4 antibody. In another embodiment, the antibody is an IgG2 antibody. In certain embodiments, the anti-CD73 antibody comprises a heavy chain constant region lacking one or more lysine (K) amino acid residues relative to a wild type heavy chain constant region. For example, in certain embodiments, the antibody comprises heavy chain constant region lacking the C-terminal lysine (K) amino acid residue of the CH3 domain of the heavy chain constant region. In certain embodiments, the anti-CD73 antibody comprises a heavy chain constant region having the amino acid sequence set forth in SEQ ID NO:73. In certain embodiments, the anti-CD73 antibody comprises a heavy chain constant region having the amino acid sequence set forth in SEQ ID NO:75. In certain embodiments, the anti-CD73 antibody comprises a light chain constant region having the amino acid sequence set forth in SEQ ID NO:74. In certain embodiments, the anti-CD73 antibody comprises a heavy chain constant region having the amino acid sequence set forth in SEQ ID NO:73 and a light chain constant region having the amino acid sequence set forth in SEQ ID NO:74. In certain embodiments, the anti-CD73 antibody comprises a heavy chain constant region having the amino acid sequence set forth in SEQ ID NO:75 and a light chain constant region having the amino acid sequence set forth in SEQ ID NO:74.

Antibody 3-F03

Antibody 3-F03 is a human IgG1/kappa monoclonal antibody with alanine at position Asparagine-297 (N297, according to EU numbering) of the heavy chain constant region to reduce effector function. 3-F03 specifically binds human, cynomolgus, and murine CD73 with high affinity ($K_D \leq 2$ nM) and has low effector functionality.

3-F03 was engineered from sequences obtained by multiple selection rounds of single donor library. scFv cassettes from this pool were then recombined into a yeast display vector library, which was subjected to FACs selection with murine CD73 (SEQ ID NO:71). The amino acid sequences of the yeast 3-F03 scFv cassette are set forth in SEQ ID NOs:77 and 65, respectively:
EVQLVESGGGLVQPGGSLRLSCAASGFTFSSYDMH-WVRQAPGKGLEWVAVMSYDG SNKYYADSVKG-RFTISRDNSKNTLYLQMNSLRAEDTAVYYCATE-IAAKGDYWGQG TLVTVSS (SEQ ID NO:77); and AIQMTQSPSSLSASVGDRVTITCRASQGIS-NYLAWYQQKPGKAPKLLIYAASTLQSGV PSRFSGSGSGTDFTLTISSLQPEDFATYYCQQSYS-TPHFGQGTRLEIK (SEQ ID NO:65).

To construct the 3-F03 antibody, the yeast 3-F03 VH and VL were modified as follows and cloned into a human IgG1/kappa scaffold. For the VH, the N-terminal glutamate (E) of yeast 3-F03 VH (SEQ ID NO:77) was removed and the threonine (T) at Kabat position H77 of SEQ ID NO:77 (i.e., position 78 of SEQ ID NO:77) was substituted with an alanine (A). For the VL, the N-terminal alanine (A) of SEQ ID NO:65 was removed. The resulting full-length human 3-F03 antibody contains the VH and VL set forth in the amino acid sequences of SEQ ID NOs:60 and 61, respectively. The resulting full-length human 3-F03 antibody is referred to herein as "3-F03". Table 3, below, shows the amino acid sequences of the 3-F03 CDRs according to IMGT, Chothia, AbM, Kabat, and Contact numbering. Table 3, below, also shows the amino acid sequences of the 3-F03 mature VH, VL, heavy chain, and light chain.

Variants of 3-F03 are also described herein. 3-F03_411 is identical to 3-F03, except that the 3-F03_411 heavy chain (i) contains an N-terminal glutamate (E) that is lacking in 3-F03 and (ii) does not include the C-terminal lysine present in 3-F03. Table 4, below, shows the amino acid sequences of the 3-F03_411 mature VH, VL, heavy chain and light chain. 3-F03_413 is identical to 3-F03_411, except that it contains a glutamate (E) at VH Kabat position H53 (position 54 of SEQ ID NO:60) instead of an aspartic acid (D). Table 5, below, shows the amino acid sequences of the 3-F03_413 CDRs according to IMGT, Chothia, AbM, Kabat, and Contact numbering. Table 5, below, also shows the amino acid sequences of the 3-F03_413 mature VH, VL, heavy chain, and light chain. Additional variants are described in the Examples below (see FIG. 21A-FIG. 21J).

TABLE 4

Amino acid sequences of 3-F03_411 HC and LC

| | SEQUENCE |
|---|---|
| VH | EVQLVESGGGLVQPGGSLRLSCAASGFTFSSYDMHWVRQAPGKG LEWVAVMSYDGSNKYYADSVKGRFTISRDNSKNALYLQMNSLRA EDTAVYYCATEIAAKGDYWGQGTLVTVSS (SEQ ID NO: 62) |
| VL | IQMTQSPSSLSASVGDRVTITCRASQGISNYLAWYQQKPGKAPK LLIYAASTLQSGVPSRFSGSGSGTDFTLTISSLQPEDFATYYCQ QSYSTPHFGQGTRLEIK (SEQ ID NO: 61) |

TABLE 3

Amino acid sequences of 3-F03 CDRs, VH, and VL

| | IMGT | Chothia | AbM | Kabat | Contact |
|---|---|---|---|---|---|
| VH CDR1 | GFTFSSYD (SEQ ID NO: 34) | GFTFSSY (SEQ ID NO: 41) | GFTFSSYDMH (SEQ ID NO: 46) | SYDMH (SEQ ID NO: 49) | SSYDMH (SEQ ID NO: 53) |
| VH CDR2 | MSYDGSNK (SEQ ID NO: 35) | SYDGSN (SEQ ID NO: 42) | VMSYDGSNKY (SEQ ID NO: 47) | VMSYDGSNKY YADSVKG (SEQ ID NO: 50) | WVAVMSYDGS NKY (SEQ ID NO: 54) |
| VH CDR3 | ATEIAAKGDY (SEQ ID NO: 36) | EIAAKGDY (SEQ ID NO: 52) | EIAAKGDY (SEQ ID NO: 52) | EIAAKGDY (SEQ ID NO: 52) | ATEIAAKGD (SEQ ID NO: 56) |
| VL CDR1 | QGISNY (SEQ ID NO: 37) | RASQGISNYLA (SEQ ID NO: 44) | RASQGISNYLA (SEQ ID NO: 44) | RASQGISNYLA (SEQ ID NO: 44) | SNYLAWY (SEQ ID NO: 57) |
| VL CDR2 | AAS (SEQ ID NO: 38) | AASTLQS (SEQ ID NO: 45) | AASTLQS (SEQ ID NO: 45) | AASTLQS (SEQ ID NO: 45) | LLIYAASTLQ (SEQ ID NO: 58) |
| VL CDR3 | QQSYSTPH (SEQ ID NO: 39) | QQSYSTPH (SEQ ID NO: 39) | QQSYSTPH (SEQ ID NO: 39) | QQSYSTPH (SEQ ID NO: 39) | QQSYSTP (SEQ ID NO: 59) |

| VH | VQLVESGGGLVQPGGSLRLSCAASGFTFSSYDMHWVRQAPGKGLEWVAVMSYDGSNKYYA DSVKGRFTISRDNSKNALYLQMNSLRAEDTAVYYCATEIAAKGDYWGQGTLVTVSS (SEQ ID NO: 60) |
|---|---|
| VL | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIK (SEQ ID NO: 61) |
| HC | VQLVESGGGLVQPGGSLRLSCAASGFTFSSYDMHWVRQAPGKGLEWVAVMSYDGSNKYYA DSVKGRFTISRDNSKNALYLQMNSLRAEDTAVYYCATEIAAKGDYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKRVEPKSCDKTHTCPPCPAPELLGGPSVFLFPPKPKD TLMISRTPEVTCVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSCSVMHEALHN HYTQKSLSLSPGK (SEQ ID NO: 66) |
| LC | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIKRTVAAPSVFIFPPSDEQLKSGTAS VVCLLNNFYPREAKVQWKVDNALQSGNSQESVTEQDSKDSTYSLSSTLTLSKADYEKHKVY ACEVTHQGLSSPVTKSFNRGEC (SEQ ID NO: 31) |

TABLE 4-continued

Amino acid sequences of 3-F03_411 HC and LC

| | SEQUENCE |
|---|---|
| Heavy Chain | EVQLVESGGGLVQPGGSLRLSCAASGFTFSSYDMHWVRQAPGKG LEWVAVMSYDGSNKYYADSVKGRFTISRDNSKNALYLQMNSLRA EDTAVYYCATEIAAKGDYWGQGTLVTVSSASTKGPSVFPLAPSS KSTSGGTAALGCLVKDYFPEPVTVSWNSGALTSGVHTFPAVLQS SGLYSLSSVVTVPSSSLGTQTYICNVNHKPSNTKVDKRVEPKSC DKTHTCPPCPAPELLGGPSVFLFPPKPKDTLMISRTPEVTCVVV DVSHEDPEVKFNWYVDGVEVHNAKTKPREEQYASTYRVVSVLTV LHQDWLNGKEYKCKVSNKALPAPIEKTISKAKGQPREPQVYTLP PSREEMTKNQVSLTCLVKGFYPSDIAVEWESNGQPENNYKTTPP VLDSDGSFFLYSKLTVDKSRWQQGNVFSCSVMHEALHNHYTQKS LSLSPG (SEQ ID NO: 30) |
| Light Chain | IQMTQSPSSLSASVGDRVTITCRASQGISNYLAWYQQKPGKAPK LLIYAASTLQSGVPSRFSGSGSGTDFTLTISSLQPEDFATYYCQ QSYSTPHFGQGTRLEIKRTVAAPSVFIFPPSDEQLKSGTASVVC LLNNFYPREAKVQWKVDNALQSGNSQESVTEQDSKDSTYSLSST LTLSKADYEKHKVYACEVTHQGLSSPVTKSFNRGEC (SEQ ID NO: 31) | comprising VL CDR1, VL CDR2, and VL CDR3 of 3-F03 (see Table 3). In some instances, the anti-CD73 antibody comprises a VH comprising VH CDR1, VH CDR2, and VH CDR3 of 3-F03 (see Table 3) and a VL comprising VL CDR1, VL CDR2, and VL CDR3 of 3-F03 (see Table 3). In some instances, the anti-CD73 antibody comprises a VH comprising VH CDR1, VH CDR2, and VH CDR3 of 3-F03_413 (see Table 5). In some instances, the anti-CD73 antibody comprises a VL comprising VL CDR1, VL CDR2, and VL CDR3 of 3-F03_413 (see Table 5). In some instances, the anti-CD73 antibody comprises a VH comprising VH CDR1, VH CDR2, and VH CDR3 of 3-F03_413 (see Table 5) and a VL comprising VL CDR1, VL CDR2, and VL CDR3 of 3-F03_413 (see Table 5). In some instances, the anti-CD73 antibodies can have, e.g., 1, 2, or 3 substitutions within one or more (i.e., 1, 2, 3, 4, 5, or 6) of the six CDRs of 3-F03 or 3-F03_413. In some instances, these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as

TABLE 5

Amino acid sequences of 3-F03_413 CDRs, VH, VL, HC, LC

| | IMGT | Chothia | AbM | Kabat | Contact |
|---|---|---|---|---|---|
| VH CDR1 | GFTFSSYD (SEQ ID NO: 34) | GFTFSSY (SEQ ID NO: 41) | GFTFSSYDMH (SEQ ID NO: 46) | SYDMH (SEQ ID NO: 49) | SSYDMH (SEQ ID NO: 53) |
| VH CDR2 | MSYEGSNK (SEQ ID NO: 40) | SYEGSN (SEQ ID NO: 43) | VMSYEGSNKY (SEQ ID NO: 48) | VMSYEGSNKY YADSVKG (SEQ ID NO: 51) | WVAVMSYEGSNKY (SEQ ID NO: 55) |
| VH CDR3 | ATEIAAKGDY (SEQ ID NO: 36) | EIAAKGDY (SEQ ID NO: 52) | EIAAKGDY (SEQ ID NO: 52) | EIAAKGDY (SEQ ID NO: 52) | ATEIAAKGD (SEQ ID NO: 56) |
| VL CDR1 | QGISNY (SEQ ID NO: 37) | RASQGISNYLA (SEQ ID NO: 44) | RASQGISNYLA (SEQ ID NO: 44) | RASQGISNYLA (SEQ ID NO: 44) | SNYLAWY (SEQ ID NO: 57) |
| VL CDR2 | AAS (SEQ ID NO: 38) | AASTLQS (SEQ ID NO: 45) | AASTLQS (SEQ ID NO: 45) | AASTLQS (SEQ ID NO: 45) | LLIYAASTLQ (SEQ ID NO: 58) |
| VL CDR3 | QQSYSTPH (SEQ ID NO: 39) | QQSYSTPH (SEQ ID NO: 39) | QQSYSTPH (SEQ ID NO: 39) | QQSYSTPH (SEQ ID NO: 39) | QQSYSTP (SEQ ID NO: 59) |
| VH | EVQLVESGGGLVQPGGSLRLSCAASGFTFSSYDMHWVRQAPGKGLEWVAVMSYEGSNKYY ADSVKGRFTISRDNSKNALYLQMNSLRAEDTAVYYCATEIAAKGDYWGQGTLVTVSS (SEQ ID NO: 63) | | | | |
| VL | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIK (SEQ ID NO: 61) | | | | |
| HC | EVQLVESGGGLVQPGGSLRLSCAASGFTFSSYDMHWVRQAPGKGLEWVAVMSYEGSNKYY ADSVKGRFTISRDNSKNALYLQMNSLRAEDTAVYYCATEIAAKGDYWGQGTLVTVSSASTK GPSVFPLAPSSKSTSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPELLGGPSVFLFPPKPK DTLMISRTPEVTCVVVDVSHEDPEVKFNWYVDGVEVHNAKTKPREEQYASTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPG (SEQ ID NO: 33) | | | | |
| LC | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIKRTVAAPSVFIFPPSDEQLKSGTAS VVCLLNNFYPREAKVQWKVDNALQSGNSQESVTEQDSKDSTYSLSSTLTLSKADYEKHKVY ACEVTHQGLSSPVTKSFNRGEC (SEQ ID NO: 31) | | | | |

The anti-CD73 antibodies can encompass the VH CDR1, VH CDR2, and VH CDR3 and the VL CDR1, VL CDR2, and VL CDR3 of 3-F03 or 3-F03_413. In some instances, the anti-CD73 antibody comprises a VH comprising VH CDR1, VH CDR2, and VH CDR3 of 3-F03 (see Table 3). In some instances, the anti-CD73 antibody comprises a VL compared to an isotype control as determined by, e.g., the assay described in Example 15); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 16); and/or (iii) bind human, cynomolgus monkey, or murine CD73 in the open conformation with high affinity (e.g., $K_D \leq 2$ nM) (e.g., as determined by the binding assay described in Example 18); and/or (iv) do not bind human, cynomolgus monkey, or murine CD73 in the closed conformation; and/or (v) bind to an epitope within amino acids 386-399 of SEQ ID NO:70 (i.e., within AAVLPFGGTFDLVQ (SEQ ID NO:78) amino acids 470-489 of SEQ ID NO:70 (i.e., within ILPNFLANGGDGFQMIKDEL (SEQ ID NO:79)) (e.g., as determined by the binding assay described in Example 6); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 17); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 20); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 21).

The anti-CD73 antibodies can comprise the VH CDR1, VH CDR2, and VH CDR3 of 3-F03 or 3-F03_413 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VH CDR1 and/or VH CDR2 and/or VH CDR3 of 3-F03 or 3-F03_413. In some embodiments, the anti-CD73 antibodies further comprise the VL CDR1, VL CDR2, and VL CDR3 of 3-F03 or 3-F03_413 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VL CDR1 and/or VL CDR2 and/or VL CDR3 of 3-F03 or 3-F03_413. In some instances, the anti-CD73 antibody comprises a VH comprising the VH CDR1, VH CDR2, and VH CDR3 set forth in SEQ ID NOs: 34, 35, and 36, respectively, and a VL comprising the VL CDR1, VL CDR2, and VL CDR3 set forth in SEQ ID NOs: 37, 38, and 39, respectively. In some instances, the anti-CD73 antibody comprises a VH comprising the VH CDR1, VH CDR2, and VH CDR3 set forth in SEQ ID NOs: 41, 42, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 46, 47, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 49, 50, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 53, 54, and 56, respectively, and a VL comprising the VL CDR1, VL CDR2, and VL CDR3 set forth in SEQ ID NOs: 57, 58, and 59, respectively. In some instances, the anti-CD73 antibody comprises a VH comprising the VH CDR1, VH CDR2, and VH CDR3 set forth in SEQ ID NOs: 34, 40, and 36, respectively, and a VL comprising the VL CDR1, VL CDR2, and VL CDR3 set forth in SEQ ID NOs: 37, 38, and 39, respectively. In some instances, the anti-CD73 antibody comprises a VH comprising the VH CDR1, VH CDR2, and VH CDR3 set forth in SEQ ID NOs: 41, 43, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 46, 48, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 49, 51, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 53, 55, and 56, respectively, and a VL comprising the VL CDR1, VL CDR2, and VL CDR3 set forth in SEQ ID NOs: 57, 58, and 59, respectively. In some instances, these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 15); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 16); and/or (iii) bind human, cynomolgus monkey, or murine CD73 in the open conformation with high affinity (e.g., $K_D \leq 2$ nM) (e.g., as determined by the binding assay described in Example 18); and/or (iv) do not bind human, cynomolgus monkey, or murine CD73 in the closed conformation; and/or (v) bind to an epitope within amino acids 386-399 of SEQ ID NO:70 (i.e., within AAVLPFGGTFDLVQ (SEQ ID NO:78) amino acids 470-489 of SEQ ID NO:70 (i.e., within ILPNFLANGGDGFQMIKDEL (SEQ ID NO:79)) (e.g., as determined by the binding assay described in Example 6); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 17); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 20); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 21).

In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In certain embodiments, the anti-CD73 antibodies comprise a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 34-36, respectively, or SEQ ID NOs:34, 40 and 36, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66. In some embodiments, the anti-CD73 antibodies comprise a heavy chain comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs:34, 40, and 36, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66. In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In certain embodiments, the anti-CD73 antibodies comprise a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 37-39, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some embodiments, the anti-CD73 antibodies comprise a light chain comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In certain embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In certain embodiments, the anti-CD73 antibodies comprise: (i) a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs: 34, 40, and 36, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 37-39, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In some embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs: 30, 33, and 66; and (ii) an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some embodiments, the anti-CD73 antibodies comprise: (i) a heavy chain comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 34-36, respectively, or SEQ ID NOs:34, 40, and 36, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66; and (ii) a light chain comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88. In certain embodiments, the anti-CD73 antibodies comprise a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs:34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65. In certain embodiments, the anti-CD73 antibodies comprise a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88 and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in SEQ ID NO: 61, 64, and 65. In certain embodiments, the anti-CD73 antibodies comprise: (i) a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88, and (ii) a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 or 3-F03_413 (i.e., the amino acid sequence set forth in SEQ ID NO:62 or 63, respectively). In certain embodiments, the anti-CD73 antibodies comprise a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 (i.e., the amino acid sequence set forth in SEQ ID NO:62). In certain embodiments, the anti-CD73 antibodies comprise a VH comprising the VH CDR1, VH CDR2, and VH CDR3 of 3-F03_413 (see Table 5, e.g., according to the IMGT definition, i.e., the amino acid sequences set forth in SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 (i.e., the amino acid sequence set forth in SEQ ID NO:63). In some embodiments, the anti-CD73 antibodies comprise a VH comprising the amino acid sequence set forth in SEQ ID NO:62. In some embodiments, the anti-CD73 antibodies comprise a VH comprising the amino acid sequence set forth in SEQ ID NO:63. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 or 3-F03_F13 (i.e., the amino acid sequence set forth in SEQ ID NO:30 or 33, respectively). In some embodiments, the anti-CD73 antibodies comprise a heavy chain comprising a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 (i.e., the amino acid sequence set forth in SEQ ID NO:30). In some embodiments, the anti-CD73 antibodies comprise a heavy chain comprising a VH comprising the VH CDR1, VH CDR2, and VH CDR3 of 3-F03_413 (see Table 5, e.g., according to the IMGT definition, i.e., the amino acid sequences set forth in SEQ ID NOs: 34, 40, and 36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_413 (i.e., the amino acid sequence set forth in SEQ ID NO:33). In some embodiments, the anti-CD73 antibodies comprise a heavy chain comprising the amino acid sequence set forth in SEQ ID NO:30. In some embodiments, the anti-CD73 antibodies comprise a heavy chain comprising the amino acid sequence set forth in SEQ ID NO:33. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03_413 (i.e., the amino acid sequence set forth in SEQ ID NO:61). In certain embodiments, the anti-CD73 antibodies comprise a VL comprising the VL CDR1, VL CDR2, and VL CDR3 of 3-F03_411 or 3-F03_413 (see Table 3, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03_413 (i.e., the amino acid sequence set forth in SEQ ID NO:61). In some embodiments, the anti-CD73 antibodies comprise a VL comprising the amino acid sequence set forth in SEQ ID NO:61. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03_413 (i.e., the amino acid sequence set forth in SEQ ID NO:31). In some embodiments, the anti-CD73 antibodies comprise a light chain comprising a VL comprising the VL CDR1, VL CDR2, and VL CDR3 of 3-F03_411 or 3-F03_413 (see Table 5, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03_413 (i.e., the amino acid sequence set forth in SEQ ID NO:31). In some embodiments, the anti-CD73 antibodies comprise a light chain comprising the amino acid sequence set forth in SEQ ID NO:31. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 or 3-F03_413 (i.e., the amino acid sequence set forth in SEQ ID NO:62 or 63, respectively) and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03_413 (i.e., the amino acid sequence set forth in SEQ ID NO:61). In certain embodiments, the anti-CD73 antibodies comprise: (i) a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03 (i.e., the amino acid sequence set forth in SEQ ID NO:62), and (ii) a VL comprising the VL CDR1, VL CDR2, and VL CDR3 of 3-F03_411 (see Table 3, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03 (i.e., the amino acid sequence set forth in SEQ ID NO:61). In certain embodiments, the anti-CD73 antibodies comprise: (i) a VH comprising the VH CDR1, VH CDR2, and VH CDR3 of 3-F03_413 (see Table 5, e.g., according to the IMGT definition, i.e., the amino acid sequences set forth in SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_413 (i.e., the amino acid sequence set forth in SEQ ID NO:63), and (ii) a VL comprising the VL CDR1, VL CDR2, and VL CDR3 of 3-F03_413 (see Table 5, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_413 (i.e., the amino acid sequence set forth in SEQ ID NO:61). In some embodiments, the anti-CD73 antibody comprises: (i) a VH comprising the amino acid sequence set forth in SEQ ID NO:62; and (ii) a VL comprising the amino acid sequence set forth in SEQ ID NO:61. In some embodiments, the anti-CD73 antibody comprises: (i) a VH comprising the amino acid sequence set forth in SEQ ID NO:63; and (ii) a VL comprising the amino acid sequence set forth in SEQ ID NO:61. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 or 3-F03_413 (i.e., the amino acid sequence set forth in SEQ ID NO:30 or 33) and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03_413 (i.e., the amino acid sequence set forth in SEQ ID NO:31). In some embodiments, the anti-CD73 antibodies comprise: (i) a heavy chain comprising the a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 (i.e., the amino acid sequence set forth in SEQ ID NO:30), and (ii) a light chain comprising a VL comprising the VL CDR1, VL CDR2, and VL CDR3 of 3-F03_411 (see Table 3, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03 (i.e., the amino acid sequence set forth in SEQ ID NO:31). In some embodiments, the anti-CD73 antibodies comprise: (i) a heavy chain comprising the a VH comprising the VH CDR1, VH CDR2, and VH CDR3 of 3-F03_413 (see Table 5, e.g., according to the IMGT definition, i.e., the amino acid sequences set forth in SEQ ID NOs: 34, 40, and 36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03 (i.e., the amino acid sequence set forth in SEQ ID NO:33), and (ii) a light chain comprising a VL comprising the VL CDR1, VL CDR2, and VL CDR3 of 3-F03_413 (see Table 5, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_413 (i.e., the amino acid sequence set forth in SEQ ID NO:31). In some embodiments, the anti-CD73 antibody comprises: (i) a heavy chain comprising the amino acid sequence set forth in SEQ ID NO:30; and (ii) a light chain comprising the amino acid sequence set forth in SEQ ID NO:31. In some embodiments, the anti-CD73 antibody comprises: (i) a heavy chain comprising the amino acid sequence set forth in SEQ ID NO:33; and (ii) a light chain comprising the amino acid sequence set forth in SEQ ID NO:31.

The CD73-binding epitope of 3-F03 (and variants thereof, e.g., 3-F03_411 and 3-F03_413) contains AAVLPFGGTFDLVQ (SEQ ID NO:78) (i.e., amino acids 386-399 of the amino acid sequence set forth in SEQ ID NO:70) and ILPNFLANGGDGFQMIKDEL (SEQ ID NO:79) (i.e., amino acids 470-489 of the amino acid sequence set forth in SEQ ID NO:70). This disclosure features antibodies that bind to CD73 an epitope within AAVLPFGGTFDLVQ (SEQ ID NO:78) and ILPNFLANGGDGFQMIKDEL (SEQ ID NO:79). This disclosure features antibodies that bind to the same epitope as 3-F03 (or a variant thereof, e.g., 3-F03_411 or 3-F03_413). This disclosure also features antibodies that competitively inhibit binding of 3-F03 (or a variant thereof, e.g., 3-F03_411 or 3-F03_413) to human CD73.

In some embodiments, the VH of 3-F03 (or a variant thereof, e.g., 3-F03_411 or 3-F03_413) is linked to a heavy chain constant region comprising a CH1 domain and a hinge region. In some embodiments, the VH of 3-F03 (or a variant thereof, e.g., 3-F03_411 or 3-F03_413) is linked to a heavy chain constant region comprising a CH3 domain. In some embodiments, the CH3 domain lacks the C-terminal lysine (K) amino acid residue. In some embodiments, the CH3 domain contains the C-terminal lysine (K) amino acid residue. In certain embodiments, the VH of 3-F03 (or a variant thereof, e.g., 3-F03_411 or 3-F03_413) is linked to a heavy chain constant region comprising a CH1 domain, hinge region, CH2 domain, and CH3 domain from human IgG1. In some embodiments, the CH3 domain from human IgG1 lacks the C-terminal lysine (K) amino acid residue. In some embodiments, the CH3 domain from human IgG1 contains the C-terminal lysine (K) amino acid residue. In certain embodiments such an antibody contains one or more additional mutations in the heavy chain constant region that increase the stability of the antibody. In certain embodiments, the heavy chain constant region includes substitutions that modify the properties of the antibody (e.g., decrease Fc receptor binding, increase or decrease antibody glycosylation, decrease binding to C1q). In certain embodiments, the heavy chain constant region includes an alanine (A) at position Asparagine-297 (N297, according to EU numbering) of the heavy chain constant region to reduce effector function.

In certain embodiments, the anti-CD73 antibody is an IgG antibody. In one embodiment, the antibody is an IgG1 antibody. In one embodiment, the antibody is an IgG4 antibody. In another embodiment, the antibody is an IgG2 antibody. In certain embodiments, the anti-CD73 antibody comprises a heavy chain constant region lacking one or more lysine (K) amino acid residues relative to a wild type heavy chain constant region. For example, in certain embodiments, the antibody comprises heavy chain constant region lacking the C-terminal lysine (K) amino acid residue of the CH3 domain of the heavy chain constant region. In certain embodiments, the anti-CD73 antibody comprises a heavy chain constant region having the amino acid sequence set forth in SEQ ID NO:73. In certain embodiments, the anti-CD73 antibody comprises a heavy chain constant region having the amino acid sequence set forth in SEQ ID NO:75. In certain embodiments, the anti-CD73 antibody comprises a light chain constant region having the amino acid sequence set forth in SEQ ID NO:74. In certain embodiments, the anti-CD73 antibody comprises a heavy chain constant region having the amino acid sequence set forth in SEQ ID NO:73 and a light chain constant region having the amino acid sequence set forth in SEQ ID NO:74. In certain embodiments, the anti-CD73 antibody comprises a heavy chain constant region having the amino acid sequence set forth in SEQ ID NO:75 and a light chain constant region having the amino acid sequence set forth in SEQ ID NO:74.

Antibody Fragments

In some instances, the anti-CD73 antibody is an antibody fragment. Fragments of the antibodies described herein (e.g., Fab, Fab', F(ab')$_2$, Facb, and Fv) may be prepared by proteolytic digestion of intact antibodies. For example, antibody fragments can be obtained by treating the whole antibody with an enzyme such as papain, pepsin, or plasmin. Papain digestion of whole antibodies produces F(ab)$_2$ or Fab fragments; pepsin digestion of whole antibodies yields F(ab')$_2$ or Fab; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., J. Immunol., 152:2968-2976 (1994); Better, M. and Horwitz, A. H., Methods in Enzymology, 178:476-496 (1989); Plueckthun, A. and Skerra, A., Methods in Enzymology, 178:476-496 (1989); Lamoyi, E., Methods in Enzymology, 121:652-663 (1989); Rousseaux, J. et al., Methods in Enzymology, (1989) 121: 663-669 (1989); and Bird, R. E. et al., TIBTECH, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)$_2$ fragments (Carter et al., Bio/Technology, 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046.

Minibodies

In some instances, the anti-CD73 antibody is a minibody. Minibodies of anti-CD73 antibodies include diabodies, single chain (scFv), and single-chain (Fv)2 (sc(Fv)2).

A "diabody" is a bivalent minibody constructed by gene fusion (see, e.g., Holliger, P. et al., Proc. Natl. Acad. Sci. U.S.A, 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.

An scFv is a single-chain polypeptide antibody obtained by linking the VH and VL with a linker (see, e.g., Huston et al., Proc. Natl. Acad. Sci. U.S.A, 85:5879-5883 (1988); and Plickthun, "The Pharmacology of Monoclonal Antibodies" Vol. 113, Ed Resenburg and Moore, Springer Verlag, New York, pp. 269-315, (1994)). The order of VHs and VLs to be linked is not particularly limited, and they may be arranged in any order. Examples of arrangements include: [VH] linker [VL]; or [VL] linker [VH]. The heavy chain variable domain and light chain variable domain in an scFv may be derived from any anti-CD73 antibody described herein.

An sc(Fv)$_2$ is a minibody in which two VHs and two VLs are linked by a linker to form a single chain (Hudson, et al., J. Immunol. Methods, (1999) 231: 177-189 (1999)). An sc(Fv)2 can be prepared, for example, by connecting scFvs with a linker. The sc(Fv)2 of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order.

Bispecific Antibodies

In some instances, the anti-CD73 antibody is a bispecific antibody. Bispecific antibodies are antibodies that have binding specificities for at least two different epitopes. Exemplary bispecific antibodies may bind to two different epitopes of the CD73 protein. Other such antibodies may combine a CD73 binding site with a binding site for another protein. Bispecific antibodies can be prepared as full length antibodies or low molecular weight forms thereof (e.g., F(ab')2 bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., Nature, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

Multivalent Antibodies

In some instances, the anti-CD73 antibody is a multivalent antibody. A multivalent antibody may be internalized (and/or catabolized) faster than a bivalent antibody by a cell expressing an antigen to which the antibodies bind. The antibodies describe herein can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. An exemplary dimerization domain comprises (or consists of) an Fc region or a hinge region. A multivalent antibody can comprise (or consist of) three to about eight (e.g., four) antigen binding sites. The multivalent antibody optionally comprises at least one polypeptide chain (e.g., at least two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is a polypeptide chain of an Fc region, X1 and X2 represent an amino acid or peptide spacer, and n is 0 or 1.

Conjugated Antibodies

In some instances, the anti-CD73 antibody is a conjugated antibody. The antibodies disclosed herein may be conjugated antibodies, which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}$Y, $^{131}$I), fluorescent substances, luminescent substances, haptens, enzymes, metal chelates, drugs, and toxins (e.g., calcheamicin, *Pseudomonas* exotoxin A, ricin (e.g. deglycosylated ricin A chain)).

In one embodiment, to improve the cytotoxic actions of anti-CD73 antibodies and consequently their therapeutic effectiveness, the antibodies are conjugated with highly toxic substances, including radioisotopes and cytotoxic agents. These conjugates can deliver a toxic load selectively to the target site (i.e., cells expressing the antigen recognized by the antibody) while cells that are not recognized by the antibody are spared. In order to minimize toxicity, conjugates are generally engineered based on molecules with a short serum half-life (thus, the use of murine sequences, and IgG3 or IgG4 isotypes).

In certain embodiments, an anti-CD73 antibody is modified with a moiety that improves its stabilization and/or retention in circulation, e.g., in blood, serum, or other tissues, e.g., by at least 1.5, 2, 5, 10, or 50 fold. For example, the anti-CD73 antibody can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-CD73 antibody can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies can be prepared by performing chemical modifications on the antibodies, respectively, or the lower molecular weight forms thereof described herein. Methods for modifying antibodies are well known in the art (e.g., U.S. Pat. Nos. 5,057,313 and 5,156,840).

Methods of Producing Antibodies

Antibodies may be produced in bacterial or eukaryotic cells. Some antibodies, e.g., Fabs, can be produced in bacterial cells, e.g., *E. coli* cells. Antibodies can also be produced in eukaryotic cells such as transformed cell lines (e.g., CHO, 293E, COS). In addition, antibodies (e.g., scFvs) can be expressed in a yeast cell such as *Pichia* (see, e.g., Powers et al., J Immunol Methods. 251:123-35 (2001)), *Hanseula*, or *Saccharomyces*. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an anti-CD73 antibody (e.g., CL25, HzCL25, 3-F03, 3-F03_411, or 3-F03_413) is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted—therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Polynucleotides, Expression Vectors, and Cells

The disclosure also provides polynucleotides and vectors encoding an anti-CD73 antibody or portion thereof (e.g., VH, VL, HC, or LC) described herein. The polynucleotides of the disclosure can be in the form of RNA or in the form of DNA. In some instances, the polynucleotide is DNA. In some instances, the polynucleotide is complementary DNA (cDNA). In some instances, the polynucleotide is RNA.

In some instances, the polynucleotide encodes a VH comprising the VH CDR1, VH CDR2, and VH CDR3 of any antibody described herein (see, e.g., Tables 1, 2, 3, and 5). In some instances, the polynucleotide encodes a VL comprising the VL CDR1, VL CDR2, and VL CDR3 of any antibody described herein (see, e.g., Tables 1, 2, 3, and 5). In some instances, the polynucleotide encodes a heavy chain comprising a VH comprising the VH CDR1, VH CDR2, and VH CDR3 of any antibody described herein (see, e.g., Tables 1, 2, 3, and 5). In some instances, the polynucleotide encodes a light chain comprising a VL comprising the VL CDR1, VL CDR2, and VL CDR3 of any antibody described herein (see, e.g., Tables 1, 2, 3, and 5). In some instances, the polynucleotide is operably linked to a promoter.

In some instances, the polynucleotide comprises: (i) a first nucleic acid sequence encoding a first polypeptide, wherein the first polypeptide comprises a VH comprising the VH CDR1, VH CDR2, and VH CDR3 of any antibody described herein (see, e.g., Tables 1, 2, 3, and 5); and (ii) a second nucleic acid sequence encoding a second polypeptide, wherein the second polypeptide comprises a VL comprising the VL CDR1, VL CDR2, and VL CDR3 of any antibody described herein (see, e.g., Tables 1, 2, 3, and 5). In some instances, the polynucleotide comprises: (i) a first nucleic acid sequence encoding a first polypeptide, wherein the first polypeptide comprises a heavy chain comprising a VH comprising the VH CDR1, VH CDR2, and VH CDR3 of any antibody described herein (see, e.g., Tables 1, 2, 3, and 5); and (ii) a second nucleic acid sequence encoding a second polypeptide, wherein the second polypeptide comprises a light chain comprising a VL comprising the VL CDR1, VL CDR2, and VL CDR3 of any antibody described herein (see, e.g., Tables 1, 2, 3, and 5). In some instances, the first nucleic acid is operably linked to a first promoter and the second nucleic acid is operably linked to a second promoter.

In some instances, the polynucleotide encodes the VH of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:22, 26, and 82-84. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In some instances, the polynucleotide encodes a polypeptide comprising the amino acid sequence set forth in any one of SEQ ID NOs:22, 26, and 82-84. In some instances, the polynucleotide encodes a polypeptide comprising the amino acid sequence set forth in SEQ ID NO:22. In some instances, the polynucleotide is operably linked to a promoter.

In some instances, the polynucleotide encodes the VL of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:23, 27, 80, and 81. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO:23, 27, 80, and 81. In some instances, the polynucleotide encodes a polypeptide comprising the amino acid sequence set forth in any one of SEQ ID NOs:23, 27, 80, and 81. In some instances, the polynucleotide encodes a polypeptide comprising the amino acid sequence set forth in SEQ ID NO:23. In some instances, the polynucleotide is operably linked to a promoter.

In some instances, the polynucleotide comprises: (i) a first nucleic acid encoding a first polypeptide, wherein the first polypeptide comprises the VH of CL25 or a variant thereof (e.g., a humanized version thereof, e.g., HzCL25); and (ii) a second nucleic acid encoding a second polypeptide, wherein the second polypeptide comprises the VL of CL25 or a variant thereof (e.g., a humanized version thereof, e.g., HzCL25). In some instances, the polynucleotide comprises: (i) a first nucleic acid sequence encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NOs:22, 26, and 82-84, and (ii) a second nucleic acid sequence encoding a second polypeptide, wherein the second polypeptide comprises an amino acid sequence having at least 80%, at least 85%, at least 90%, at least 95%, at least 97%, or 100% identity to the amino acid sequence set forth in any one of SEQ ID NOs:23, 27, 80, and 81. In some instances, the polynucleotide comprises: (i) a first nucleic acid sequence encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) a second nucleic acid sequence encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some instances, the first nucleic acid encodes the amino acid sequence set forth in any one of SEQ ID NOs:22, 26, and 82-84 and the second nucleic acid encodes the amino acid sequence set forth in any one of SEQ ID NOs:23, 27, 80, and 81. In some instances, the first nucleic acid encodes the amino acid sequence set forth in SEQ ID NO:22 and the second nucleic acid encodes the amino acid sequence set forth in SEQ ID NO:23. In some instances, the first nucleic acid is operably linked to a first promoter and the second nucleic acid is operably linked to a second promoter.

In some instances, the polynucleotide encodes the heavy chain of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:24. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In some instances, the polynucleotide encodes a polypeptide comprising the amino acid sequence set forth in SEQ ID NO:24. In some instances, the polynucleotide comprises the sequence set forth in SEQ ID NO:89. In some instances, the polynucleotide is operably linked to a promoter.

In some instances, the polynucleotide encodes the light chain of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:25. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some instances, the polynucleotide encodes a polypeptide comprising the amino acid sequence set forth in SEQ ID NO:25. In some instances, the polynucleotide comprises the sequence set forth in SEQ ID NO:90. In some instances, the polynucleotide is operably linked to a promoter.

In some instances, the polynucleotide encodes the heavy chain of CL25 or a variant thereof (e.g., a humanized version thereof, e.g., HzCL25) and the light chain of CL25 or a variant thereof (e.g., a humanized version thereof, e.g., HzCL25). In some instances, the polynucleotide comprises: (i) a first nucleic acid encoding a first polypeptide, wherein the first polypeptide comprises an amino acid sequence having at least 80%, at least 85%, at least 90%, at least 95%, at least 97%, or 100% identity to the amino acid sequence set forth in SEQ ID NO:24, and (ii) a second nucleic acid encoding a second polypeptide, wherein the second polypeptide comprises an amino acid sequence having at least 80%, at least 85%, at least 90%, at least 95%, at least 97%, or 100% identity to the amino acid sequence set forth in SEQ ID NO:25. In some instances, the polynucleotide comprises: (i) a first nucleic acid encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24, and (ii) a second nucleic acid encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some instances, the polynucleotide comprises: (i) a first nucleic acid encoding a first polypeptide, wherein the first polypeptide comprises the amino acid sequence set forth in SEQ ID NO:24, and (ii) a second nucleic acid encoding a second polypeptide, wherein the second polypeptide comprises the amino acid sequence set forth in SEQ ID NO:25. In some instances, the polynucleotide comprises: (i) a first nucleic acid comprising the sequence set forth in SEQ ID NO:89, and (ii) a second nucleic acid comprising the sequence set forth in SEQ ID NO:90. In some instances, the first nucleic acid is operably linked to a first promoter and the second nucleic acid is operably linked to a second promoter.

In some instances, the polynucleotide encodes the VH of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs: 32, 60, 62, 63, 67-69, 77, and 85-88. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In some instances, the polynucleotide encodes a polypeptide comprising the amino acid sequence set forth in any one of SEQ ID NOs: 32, 60, 62, 63, 67-69, 77, and 85-88. In some instances, the polynucleotide encodes a polypeptide comprising the amino acid sequence set forth in SEQ ID NO:62. In some instances, the polynucleotide encodes a polypeptide comprising the amino acid sequence set forth in SEQ ID NO:63. In some instances, the polynucleotide is operably linked to a promoter.

In some instances, the polynucleotide encodes the VL of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:61, 64, and 65. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 61, 64, and 65. In some instances, the polynucleotide encodes a polypeptide comprising the amino acid sequence set forth in any one of SEQ ID NOs: 61, 64, and 65. In some instances, the polynucleotide encodes a polypeptide comprising the amino acid sequence set forth in SEQ ID NO:61. In some instances, the polynucleotide is operably linked to a promoter.

In some instances, the polynucleotide comprises: (i) a first nucleic acid encoding a first polypeptide, wherein the first polypeptide comprises the VH of 3-F03 or a variant thereof (e.g., 3-F03_411 or 3-F03_413); and (ii) a second nucleic acid encoding a second polypeptide, wherein the second polypeptide comprises the VL of 3-F03 or a variant thereof (e.g., 3-F03_411 or 3-F03_413). In some instances, the polynucleotide comprises: (i) a first nucleic acid sequence encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NOs: 32, 60, 62, 63, 67-69, 77, and 85-88, and (ii) a second nucleic acid sequence encoding a second polypeptide, wherein the second polypeptide comprises an amino acid sequence having at least 80%, at least 85%, at least 90%, at least 95%, at least 97%, or 100% identity to the amino acid sequence set forth in any one of SEQ ID NOs:61, 64, and 65. In some instances, the polynucleotide comprises: (i) a first nucleic acid sequence encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) a second nucleic acid sequence encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:61, 64, and 65. In some instances, the first nucleic acid encodes the amino acid sequence set forth in any one of SEQ ID NOs: 32, 60, 62, 63, 67-69, 77, and 85-88 and the second nucleic acid encodes the amino acid sequence set forth in any one of SEQ ID NOs:61, 64, and 65. In some instances, the first nucleic acid encodes the amino acid sequence set forth in SEQ ID NO:62 and the second nucleic acid encodes the amino acid sequence set forth in SEQ ID NO:61. In some instances, the first nucleic acid encodes the amino acid sequence set forth in SEQ ID NO:63 and the second nucleic acid encodes the amino acid sequence set forth in SEQ ID NO:61. In some instances, the first nucleic acid is operably linked to a first promoter and the second nucleic acid is operably linked to a second promoter.

In some instances, the polynucleotide encodes the heavy chain of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NO: 30, 33, and 66. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 30, 33, and 66. In some instances, the polynucleotide encodes a polypeptide comprising the amino acid sequence set forth in any one of SEQ ID NO: 30, 33, and 66. In some instances, the polynucleotide encodes a polypeptide comprising the amino acid sequence set forth in SEQ ID NO:30. In some instances, the polynucleotide encodes a polypeptide comprising the amino acid sequence set forth in SEQ ID NO:33. In some instances, the polynucleotide comprises the sequence set forth in SEQ ID NO:91. In some instances, the polynucleotide comprises the sequence set forth in SEQ ID NO:93. In some instances, the polynucleotide is operably linked to a promoter.

In some instances, the polynucleotide encodes the light chain of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:31. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some instances, the polynucleotide encodes a polypeptide comprising the amino acid sequence set forth in SEQ ID NO: 31. In some instances, the polynucleotide encodes a polypeptide comprising the amino acid sequence set forth in SEQ ID NO:31. In some instances, the polynucleotide comprises the sequence set forth in SEQ ID NO:92. In some instances, the polynucleotide is operably linked to a promoter.

In some instances, the polynucleotide encodes the heavy chain of 3-F03 or a variant thereof (e.g., 3-F03_411 or 3-F03_413) and the light chain of 3-F03 or a variant thereof (e.g., 3-F03_411 or 3-F03_413). In some instances, the polynucleotide comprises: (i) a first nucleic acid encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NO: 30, 33, and 66, and (ii) a second nucleic acid encoding a second polypeptide, wherein the second polypeptide comprises an amino acid sequence having at least 80%, at least 85%, at least 90%, at least 95%, at least 97%, or 100% identity to the amino acid sequence set forth in SEQ ID NO: 31. In some instances, the polynucleotide comprises: (i) a first nucleic acid encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 30, 33, and 66, and (ii) a second nucleic acid encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some instances, the polynucleotide comprises: (i) a first nucleic acid encoding a first polypeptide, wherein the first polypeptide comprises the amino acid sequence set forth in any one of SEQ ID NO: 30, 33, and 66, and (ii) a second nucleic acid encoding a second polypeptide, wherein the second polypeptide comprises the amino acid sequence set forth in SEQ ID NO: 31. In some instances, the polynucleotide comprises: (i) a first nucleic acid encoding a first polypeptide, wherein the first polypeptide comprises the amino acid sequence set forth in SEQ ID NO:30, and (ii) a second nucleic acid encoding a second polypeptide, wherein the second polypeptide comprises the amino acid sequence set forth in SEQ ID NO:31. In some instances, the polynucleotide comprises: (i) a first nucleic acid encoding a first polypeptide, wherein the first polypeptide comprises the amino acid sequence set forth in SEQ ID NO:33, and (ii) a second nucleic acid encoding a second polypeptide, wherein the second polypeptide comprises the amino acid sequence set forth in SEQ ID NO:31. In some instances, the polynucleotide comprises: (i) a first nucleic acid comprising the sequence set forth in SEQ ID NO:91, and (ii) a second nucleic acid comprising the sequence set forth in SEQ ID NO:92. In some instances, the polynucleotide comprises: (i) a first nucleic acid comprising the sequence set forth in SEQ ID NO:93, and (ii) a second nucleic acid comprising the sequence set forth in SEQ ID NO:92. In some instances, the first nucleic acid is operably linked to a first promoter and the second nucleic acid is operably linked to a second promoter.

In some embodiments, a polynucleotide described herein is isolated.

Also provided herein are expression vectors encoding the anti-CD73 antibodies or portions thereof (e.g., VH, VL, HC, and/or LC) described herein. Also provided herein are expression vectors comprising one or more polynucleotides described herein. Various types of expression vectors are known in the art and described herein (e.g., see the section "Methods of Producing Antibodies" above).

Also provided herein are cells comprising the anti-CD73 antibodies described herein. Also provided herein are cells comprising one or more polynucleotides described herein. Also provided herein are cells comprising one or more expression vectors described herein. Various types of cells are known in the art and described herein (e.g., see the section "Methods of Producing Antibodies" above).

Anti-CD73 Antibodies with Altered Glycosylation

Different glycoforms can profoundly affect the properties of a therapeutic, including pharmacokinetics, pharmacodynamics, receptor-interaction and tissue-specific targeting (Graddis et al., 2002, Curr Pharm Biotechnol. 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, PNAS, 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. BioProcess International April 2003. 44-53); the microheterogeneity of human IgG oligosaccharides can affect biological functions such as CDC and ADCC, binding to various Fc receptors, and binding to C1q protein (Wright A. & Morrison SL. TIBTECH 1997, 15 26-32; Shields et al. J Biol Chem. 2001 276(9):6591-604; Shields et al. J Biol Chem. 2002; 277(30): 26733-40; Shinkawa et al. J Biol Chem. 2003 278(5):3466-73; Umana et al. Nat Biotechnol. 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, Therapeutic Immunology 2:77-94 (1995). Thus, in some instances, the anti-CD73 antibody contains an Asn297Ala substitution relative to a wild type constant region.

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 J. Immunol. 148: 3062) and an aglycosyl anti-CD3 antibody does not induce cytokine release syndrome in mice or humans (Boyd, 1995 supra; Friend, 1999 Transplantation 68:1632). Aglycosylated forms of the anti-CD73 antibody also have reduced effector function.

Importantly, while removal of the glycans in the CH2 domain appears to have a significant effect on effector function, other functional and physical properties of the antibody remain unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 Mol. Immunol. 29:949).

The anti-CD73 antibodies of the present invention may be modified or altered to elicit increased or decreased effector function(s) (compared to a second CD73-specific antibody). Methods for altering glycosylation sites of antibodies are described, e.g., in U.S. Pat. Nos. 6,350,861 and 5,714,350, WO 05/18572 and WO 05/03175; these methods can be used to produce anti-CD73 antibodies of the present invention with altered, reduced, or no glycosylation.

Indications

The anti-CD73 antibodies of the present disclosure can modulate the activity of CD73. Accordingly, the compounds, salts or stereoisomers described herein can be used in methods of inhibiting CD73 by contacting CD73 with any one or more of the antibodies or compositions described herein. In some embodiments, the antibodies can be used in methods of inhibiting activity of CD73 in an individual/patient in need of the inhibition by administering an effective amount of an antibody described herein. In some embodiments, modulating is inhibiting. In some embodiments, the contacting is in vivo. In some embodiments, the contacting is ex vivo or in vitro.

Another aspect of the present disclosure pertains to methods of treating a CD73-associated disease or disorder in an individual (e.g., patient) by administering to the individual in need of such treatment a therapeutically effective amount or dose of one or more antibodies of the present disclosure or a pharmaceutical composition thereof. A CD73-associated disease or disorder can include any disease, disorder or condition that is directly or indirectly linked to expression or activity of CD73, including overexpression and/or abnormal activity levels.

Another aspect of the present disclosure pertains to methods of treating a disease or disorder (e.g., cancer) in an individual (e.g., patient) by administering to the individual in need of such treatment a therapeutically effective amount or dose of one or more antibodies of the present disclosure or a pharmaceutical composition thereof, wherein the disease or disorder has a high adenosine signature. Methods of determining that a disease or disorder has a high adenosine signature are known in the art. For instance, gene expression analysis of tumor tissue may be performed using a defined panel of adenosine-responsive genes.

The compounds of the present disclosure are useful in the treatment of diseases related to the activity of CD73 including, for example, cancer, inflammatory diseases, cardiovascular diseases, neurodegenerative diseases, immunomodulatory disorders, central nerve system diseases, and diabetes.

Based on the compelling roles of CD73 in multiple immunosuppressive mechanisms, developing inhibitors can boost the immune system to suppress tumor progression. Anti-CD73 antibodies can be used to treat, alone or in combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer (e.g., hepatocellular carcinoma), uterine cancer, head and neck cancer (e.g., head and neck squamous cell carcinoma), and renal cell carcinoma. In some embodiments, the prostate cancer is metastatic castrate-resistant prostate carcinoma (mCRPC). In some embodiments, the colorectal cancer is colorectal carcinoma (CRC).

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is head and neck cancer (e.g., head and neck squamous cell carcinoma), colorectal cancer, lung cancer (e.g., non-small cell lung cancer (NSCLC)), melanoma, ovarian, bladder, liver cancer (e.g., hepatocellular carcinoma), or renal cell carcinoma.

In some embodiments, the disease or disorder is mesothelioma or adrenocarcinoma. In some embodiments, the disease or disorder is mesothelioma. In some embodiments, the disease or disorder is adrenocarcinoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the antibodies of the disclosure can be used in treating pulmonary inflammation, including bleomycin-induced pulmonary fibrosis and injury related to adenosine deaminase deficiency.

In some embodiments, the antibodies of the disclosure can be used as a treatment for inflammatory disease such as allergic reactions (e.g., CD73-dependent allergic reactions) and other CD73-immune reactions. Further inflammatory diseases that can be treated by antibodies of the disclosure include respiratory disorders, sepsis, reperfusion injury, and thrombosis.

In some embodiments, the antibodies of the disclosure can be used as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality.

In some embodiments, the antibodies of the disclosure can be used as a treatment for disorders in motor activity; deficiency caused by degeneration of the striatonigral dopamine system; and Parkinson's disease; some of the motivational symptoms of depression.

In some embodiments, the compounds of the disclosure can be used as a treatment for diabetes and related disorders, such as insulin resistance. Diabetes affects the production of adenosine and the expression of A2B adenosine receptors (A2BRs) that stimulate IL-6 and CRP production, insulin resistance, and the association between A2BR gene single-nucleotide polymorphisms (ADORA2B SNPs) and inflammatory markers. The increased A2BR signaling in diabetes may increase insulin resistance in part by elevating pro-inflammatory mediators. Selective anti-CD73 antibodies may be useful to treat insulin resistance.

The terms "individual" or "patient" or "subject", used interchangeably, refer to any animal, including mammals, preferably mice, rats, other rodents, rabbits, dogs, cats, swine, cattle, sheep, horses, or primates, and most preferably humans (i.e., a human subject).

The phrase "therapeutically effective amount" refers to the amount of active antibody or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the antibodies of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Pharmaceutical Compositions

An anti-CD73 antibody described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the anti-CD73 antibody may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

Administration

The anti-CD73 antibody can be administered to a subject, e.g., a subject in need thereof, for example, a human subject, by a variety of methods. For many applications, the route of administration is one of: intravenous injection or infusion (IV), subcutaneous injection (SC), intraperitoneally (IP), or intramuscular injection. It is also possible to use intraarticular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The route and/or mode of administration of the antibody can also be tailored for the individual case, e.g., by monitoring the subject, e.g., using tomographic imaging, e.g., to visualize a tumor.

The antibody can be administered as a fixed dose, or in a mg/kg patient weight dose. The dose can also be chosen to reduce or avoid production of antibodies against the anti-CD73 antibody. Dosage regimens are adjusted to provide the desired response, e.g., a therapeutic response or a combinatorial therapeutic effect. Generally, doses of the anti-CD73 antibody (and optionally a second agent) can be used in order to provide a subject with the agent in bioavailable quantities.

Dosage unit form or "fixed dose" or "flat dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody may be administered via continuous infusion.

The following are examples of the practice of the invention. They are not to be construed as limiting the scope of the invention in any way.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Generation of Anti-Human CD73 Monoclonal Antibodies

To generate anti-human CD73 monoclonal antibodies, mice were immunized with recombinant human CD73 (SEQ ID NO:70) protein comprising a C-terminal HIS-tag and B cells were isolated from the mouse spleen and lymph nodes. Antibody sequences of the B cells were determined using 10× Genomics VH/VL paired B cell sequencing. The murine VH/VL pairs were expressed as chimeras with huIgG1 Fc (SEQ ID NOs: 73 and 74) and tested for binding and functionality. An antibody designated CL25 was produced by this process. Table 1, above, shows the amino acid sequences of the CL25 CDRs according to IMGT, Chothia, AbM, Kabat, and Contact numbering and the mature VH, VL, heavy chain, and light chain.

Chimeric antibody CL25 (comprising the murine VH of SEQ ID NO:26 and murine VL of SEQ ID NO:27) was humanized to minimize the immunogenicity of the antibody frameworks while maintaining specific activity. Humanization was conducted by aligning the VH and VL sequences to a database of human VH and VK genes. The CDRs (Table 1) from the murine CL25 antibody were grafted into several top human VH and VK genes. The VH and VL sequences of exemplary humanized CL25 antibodies are depicted in FIG. 1A-FIG. 1C. Alignments of the VH and VL of CL25 and exemplary humanized CL25 antibodies are depicted in FIG. 1D and FIG. 1E, respectively. Several framework mutations present in the murine CL25 were also tested along with the murine CDRs (FIG. 1A-FIG. 1E). The humanized version of CL25 having a VH of SEQ ID NO:22 and a VL of SEQ ID NO:23, referred to herein as "HzCL25", was selected for further studies. Table 2, above, shows the amino acid sequences of the HzCL25 CDRs according to IMGT, Chothia, AbM, Kabat, and Contact numbering and the mature VH, VL, heavy chain, and light chain.

Example 2: Binding of Anti-Human CD73 Monoclonal Antibodies to Cell Surface CD73

Figure 2B:
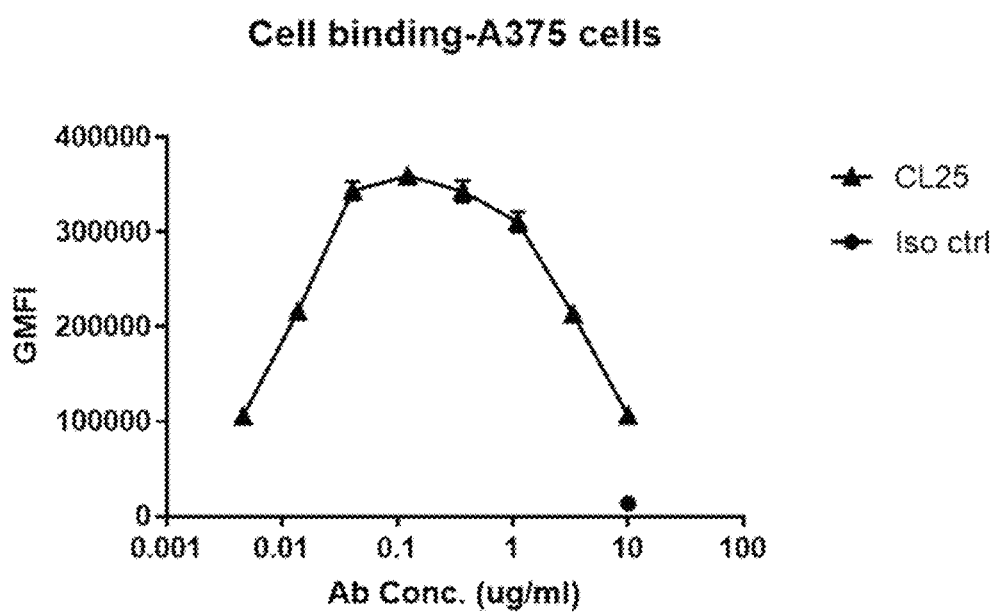
FIG. 2B is a graph depicting the cell binding (measured by GMFI) for CL25, or isotype control (iso ctrl) at the indicated concentrations on A375 cells.

To test the binding of humanized and non-humanized CL25 clones to cell surface CD73, MDA-MB-231 or A375 cells were washed and added to 96-well plates at $5 \times 10^4$ cells/well. The cells were stained with the indicated concentration of antibodies for 30 minutes on ice (FIG. 2A and FIG. 2B). Next, the cells were washed and stained using goat anti-mouse secondary conjugated to phycoerythrin (PE) for 30 minutes on ice. The cells were then washed and analyzed by flow cytometry. Geometric mean fluorescence intensity (GMFI) of CD73 staining was graphed (FIG. 2A and FIG. 2B). Both CL25 and HzCL25 displayed high potency binding to cells with high levels of surface CD73 (MDA-MB-231 cells) and moderate levels of surface CD73 (as tested in A375 cells).

Figure 3A:
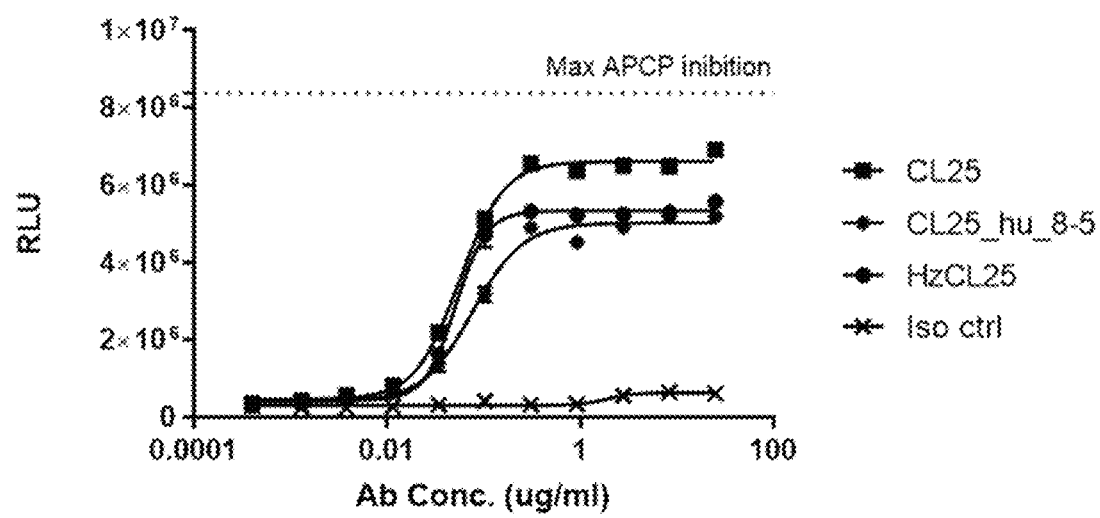
FIG. 3A is a graph depicting the cellular CD73 inhibition on A375 cells treated with the indicated antibodies or isotype control (iso ctrl) at the indicated concentrations.
Figure 3B:
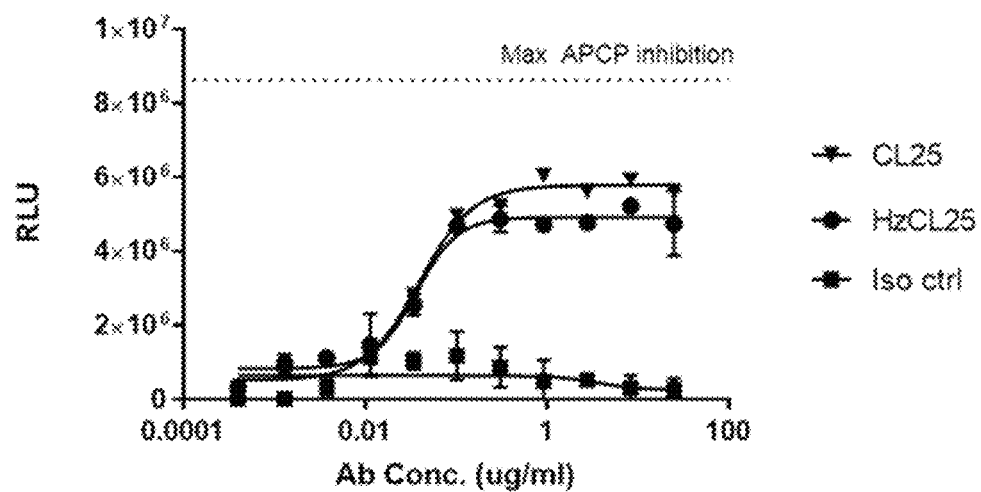
FIG. 3B is a graph depicting the cellular CD73 inhibition on MDA-MB-231 cells treated with the indicated antibodies or isotype control (iso ctrl) at the indicated concentrations.
Figure 3C:
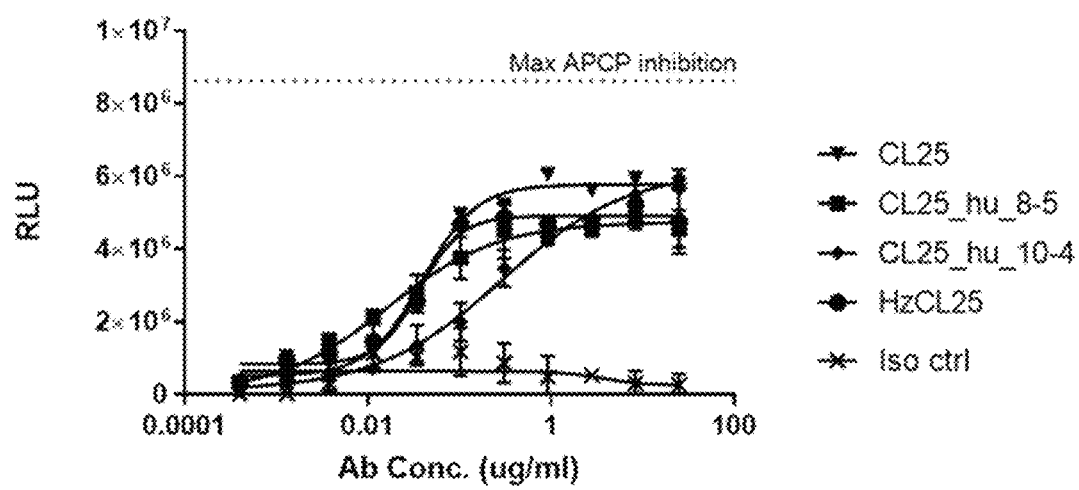
FIG. 3C is a graph depicting the cellular CD73 inhibition on MDA-MB-231 cells treated with the indicated antibodies or isotype control (iso ctrl) at the indicated concentrations.

Example 3: Anti-Human CD73 Monoclonal Antibody-Mediated Cellular CD73 Inhibition To measure ability of anti-CD73 antibody to inhibit CD73 activity on cells, A375 and MDA-MB-231 cells were washed with serum free RPMI media (ThermoFisher) and plated in 96-well plates at a concentration of $8 \times 10^4$ cells/well for A375 or $1 \times 10^4$ cells/well for MDA-MB-231. The cells were incubated with the indicated concentration of antibodies or APCP at 37° C. 5% $CO_2$ for 30 minutes (FIG. 3A, FIG. 3B, and FIG. 3C). Next, adenosine monophosphate (AMP) was added to a final concentration of 100 µM and cells were incubated an additional 3 hours at 37° C. 5% $CO_2$. Plates were centrifuged for 1-2 minutes at 300 g and 25 µL of supernatant was transferred into a new 96-well plates. AMP-Glo Assay was used according to the manufacturer's instructions (Promega). Relative luminescence unit (RLU) is directly correlated with the AMP concentration in this assay. Results are depicted in FIG. 3A, FIG. 3B, and FIG. 3C.

Both CL25 and HzCL25 had good potency in inhibiting cellular CD73 in both tested cell types (FIG. 3A, FIG. 3B, and FIG. 3C). HzCL25 had a similar ability as CL25 to inhibit cellular CD73 (FIG. 3A, FIG. 3B, and FIG. 3C).

Example 4: Anti-Human CD73 Monoclonal Antibody-Mediated Soluble CD73 Inhibition

Figure 4:
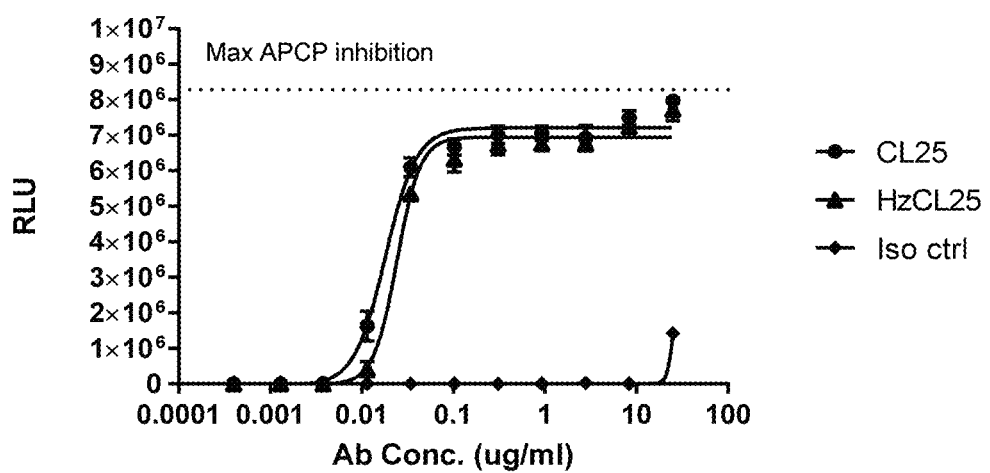
FIG. 4 is a graph depicting inhibition of recombinant CD73 treated with the indicated antibodies or isotype control (iso ctrl) at the indicated concentrations.

To measure the ability of the CD73 antibodies to inhibit CD73 activity of recombinant protein, recombinant human CD73 (rhuCD73) (SEQ ID NO:70) was added to 96-well plates at a final concentration of 0.008 µg/mL with the indicated concentration of antibodies (FIG. 4) or adenosine 5'[α,β-methylene]diphosphate (APCP) and incubated at 37° C. 5% $CO_2$ for 30 minutes. After the 30 minute incubation, AMP was added to a final concentration of 100 µM and the reactions were incubated an additional 3 hours at 37° C. 5% $CO_2$. 25 µL of supernatant was transferred into new 96-well plates. The AMP-Glo Assay was used according to the manufacturer's instructions. RLU is a directly correlated with the AMP concentration in this assay. Results are depicted in FIG. 4. Both CL25 and HzCL25 showed high potency and no hook-effect (FIG. 4). HzCL25 had a similar ability as CL25 to inhibit cellular CD73 (FIG. 4).

Example 5: Anti-Human CD73 Monoclonal Antibody-Mediated Reversal of AMP-Mediated Suppression of T Cell Proliferation To measure the ability of the CD73 antibodies to reverse AMP-mediated suppression of T cell proliferation, primary human $CD4^+$ T cells were purified from peripheral blood mononuclear cells (PBMCs) using a human $CD4^+$ T-cell isolation kit (Miltenyi Biotec). Isolated $CD4^+$ T cells were labeled with 1 µM of carboxyfluorescein succinimidyl ester (CFSE) (BD Biosciences) according to the manufacturer's protocol. CFSE labeled cells were resuspended in RPMI containing 10% fetal bovine serum and 60 IU/ml recombinant human IL-2. Approximately 50,000 cells/well were added in round bottom 96-well plate. Dynabeads human T activator CD3/CD28 beads were added to cell suspension at bead:cell ratio 1:1 and incubated for 1 hour at 37 degrees C. Serial dilutions of antibodies were added into the designated wells and incubated for 30 minutes at 37 degrees C. Finally AMP was added at a final concentration of 1000 µM and the whole culture was incubated for 5 days at 37 degrees C. in the incubator. After 5 days, $CD4^+$ T cell proliferation was determined by CFSE based flow cytometry analysis using LSRFORTESSA X-20 analyzer (BD Biosciences).

Figure 5A:
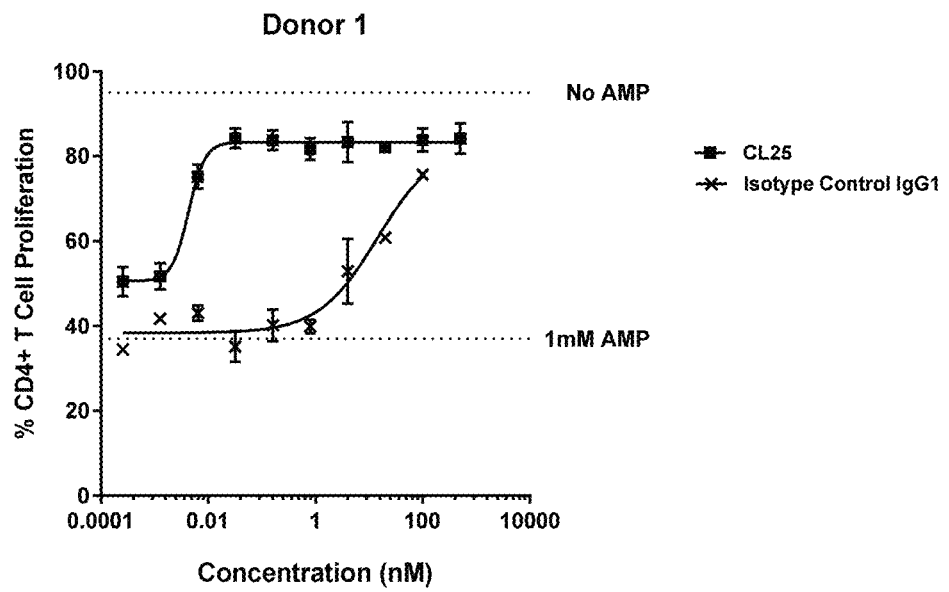
FIGS. 5A-5N are each graphs depicting the percent CD4+ T cell proliferation in donor cells treated with the indicated antibody or isotype control at various concentrations.
Figure 5B:
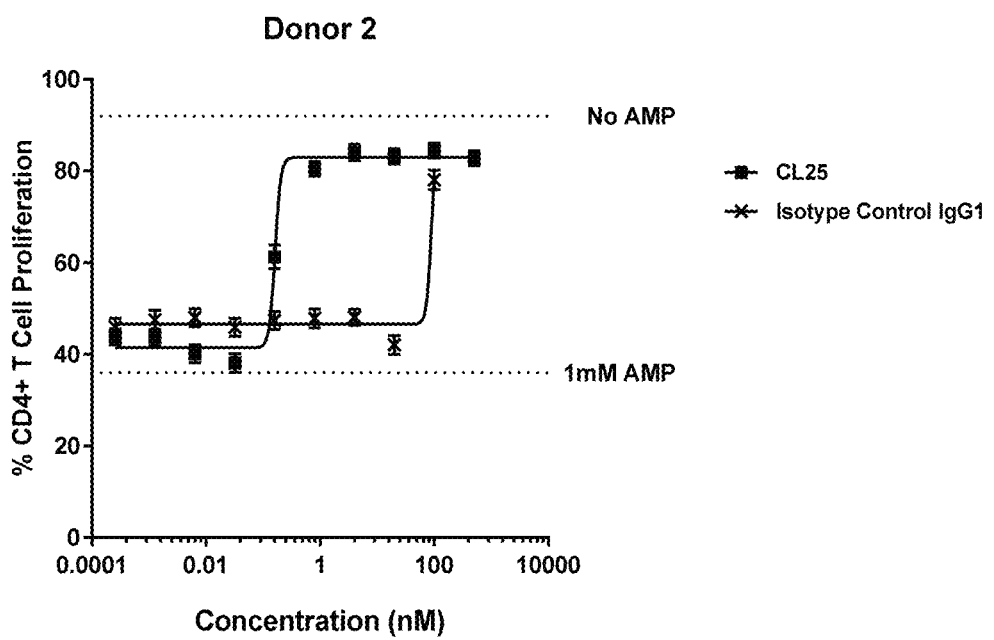
Figure 5C:
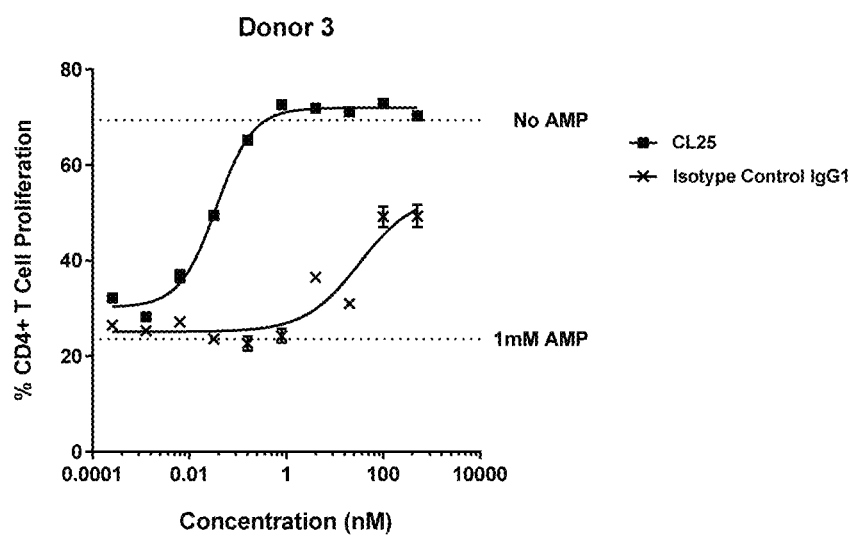
Figure 5D:
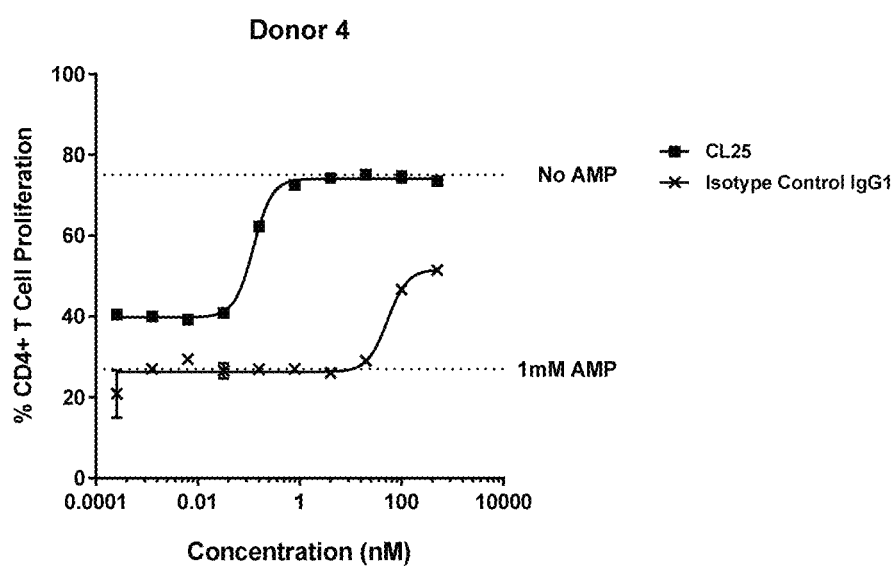
Figure 5E:
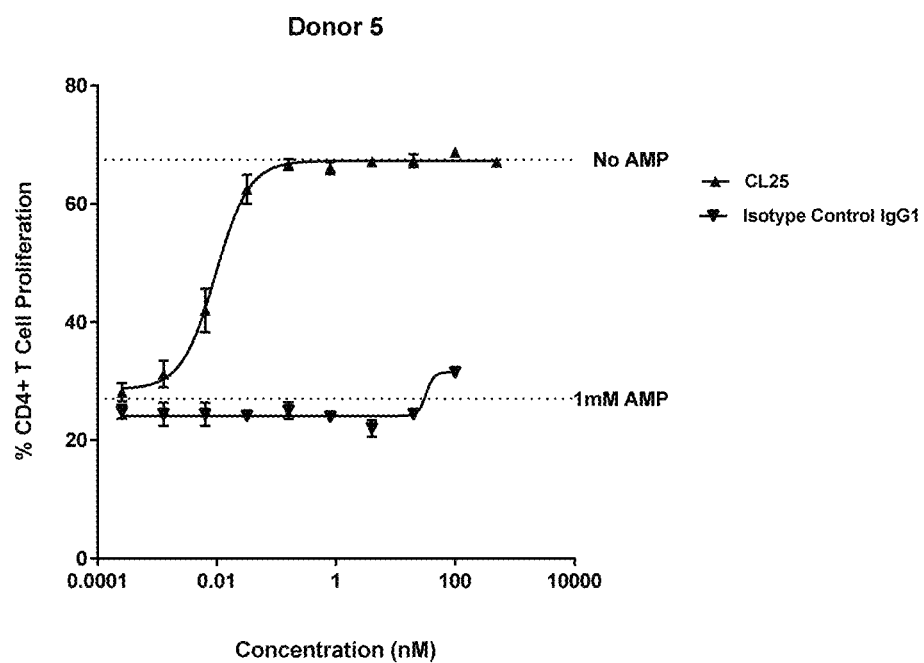
Figure 5F:
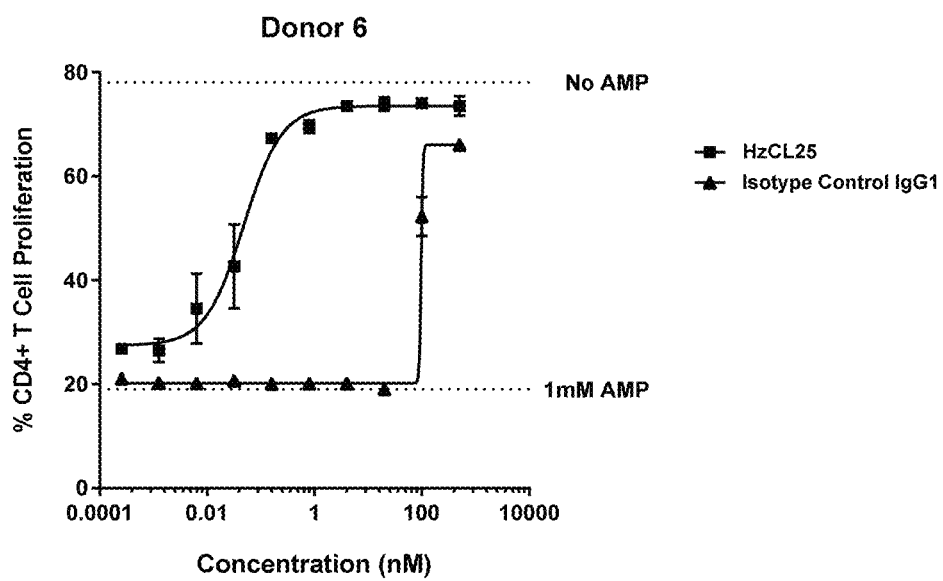
Figure 5G:
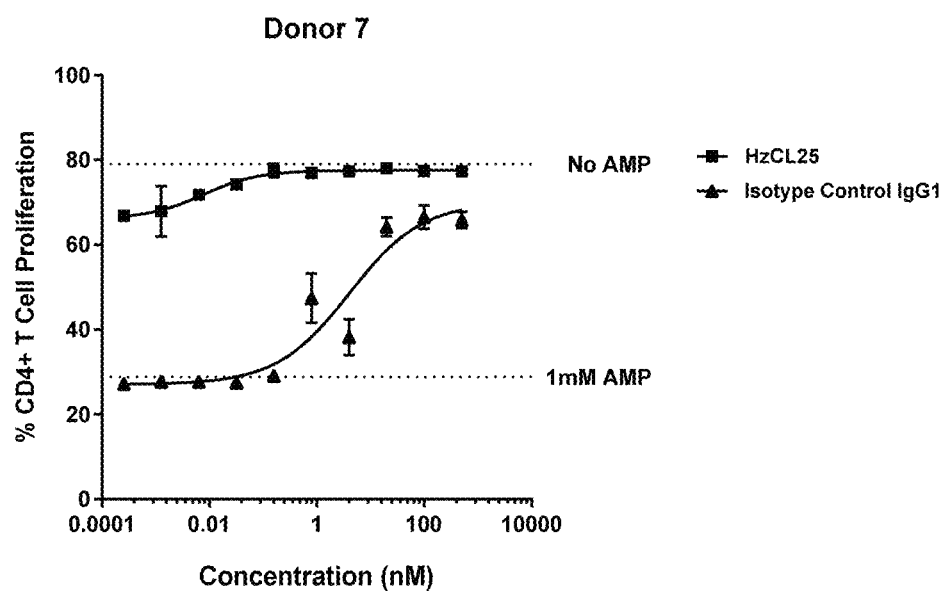
Figure 5H:
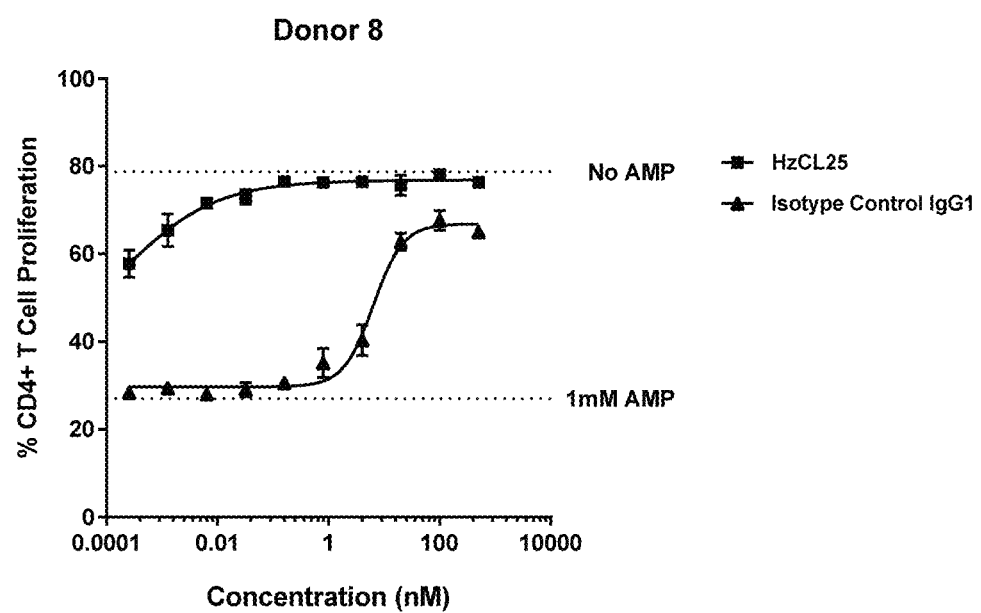
Figure 5I:
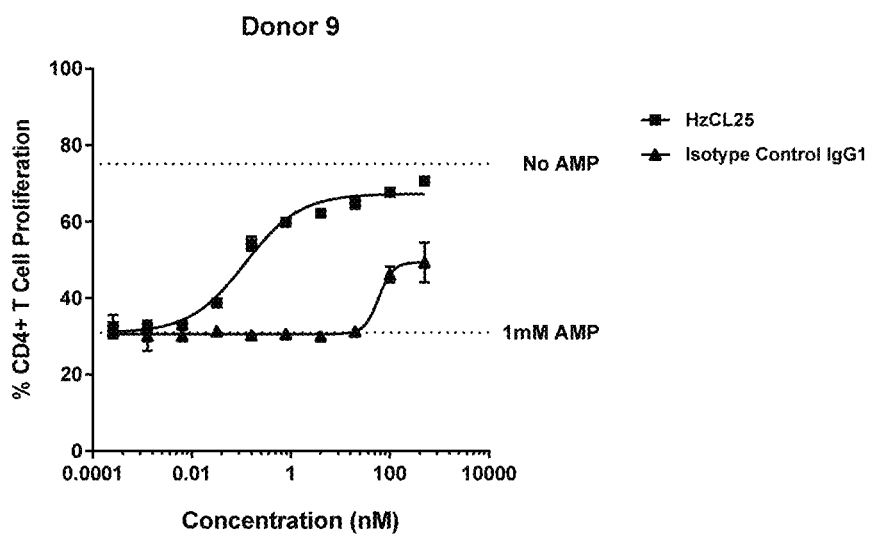
Figure 5J:
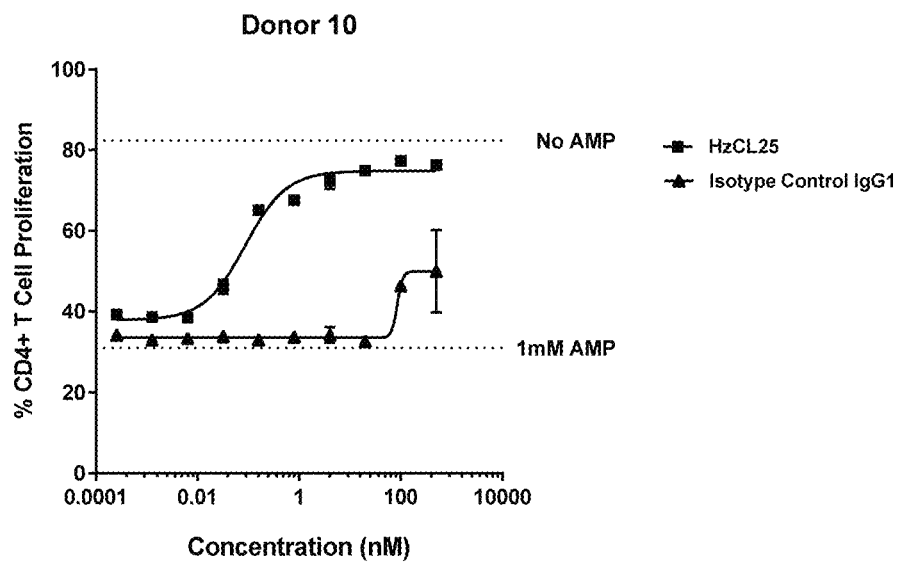
Figure 5K:
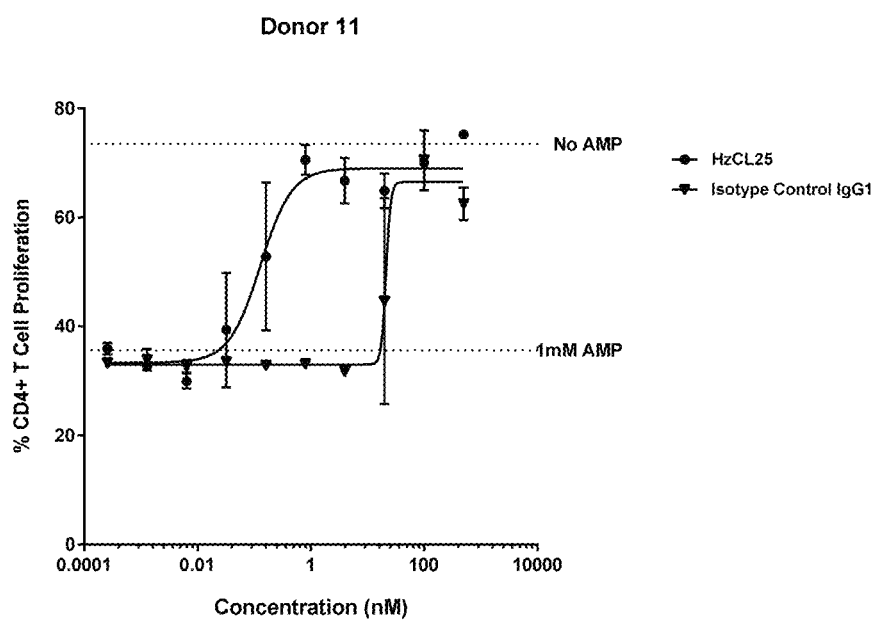
Figure 5L:
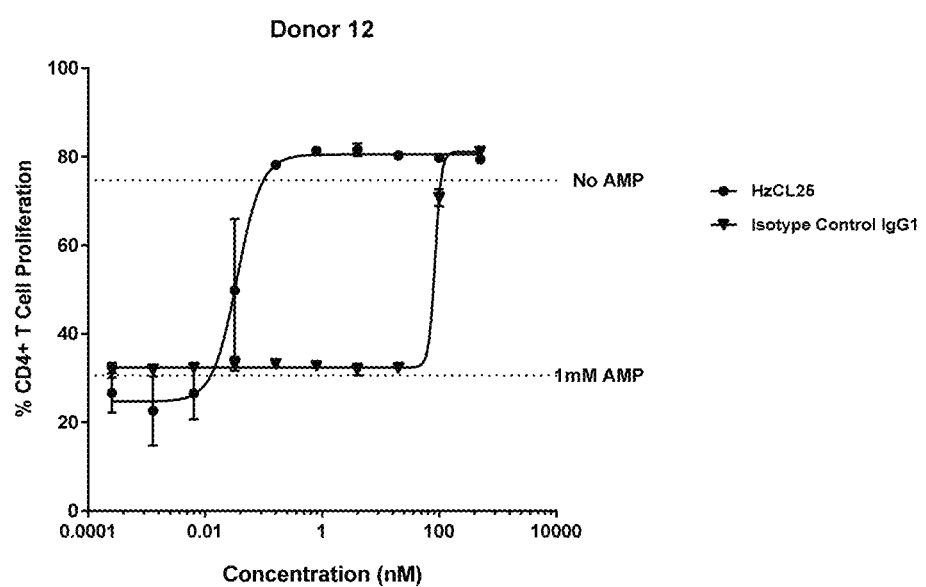
Figure 5M:
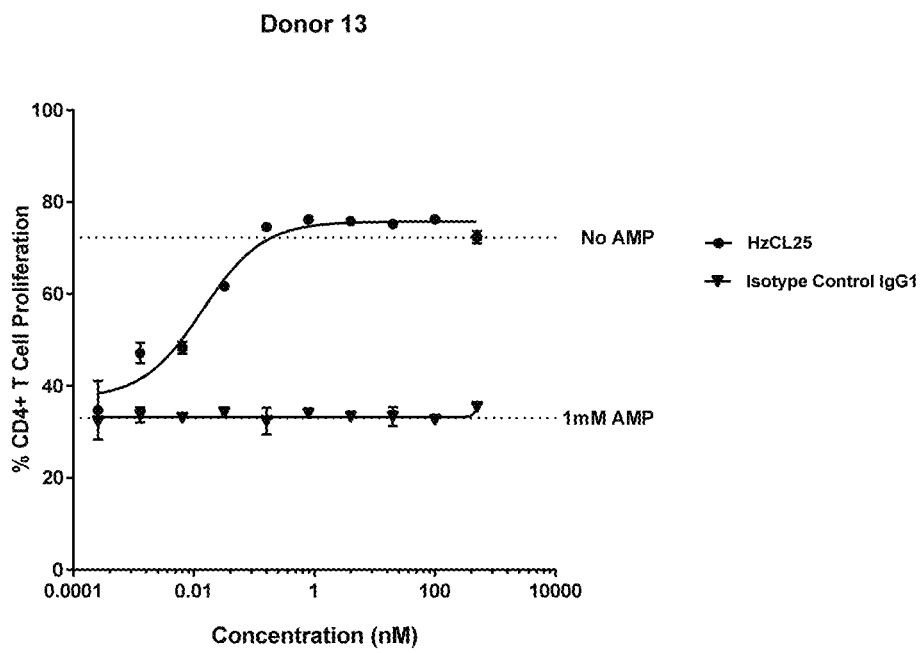
Figure 5N:
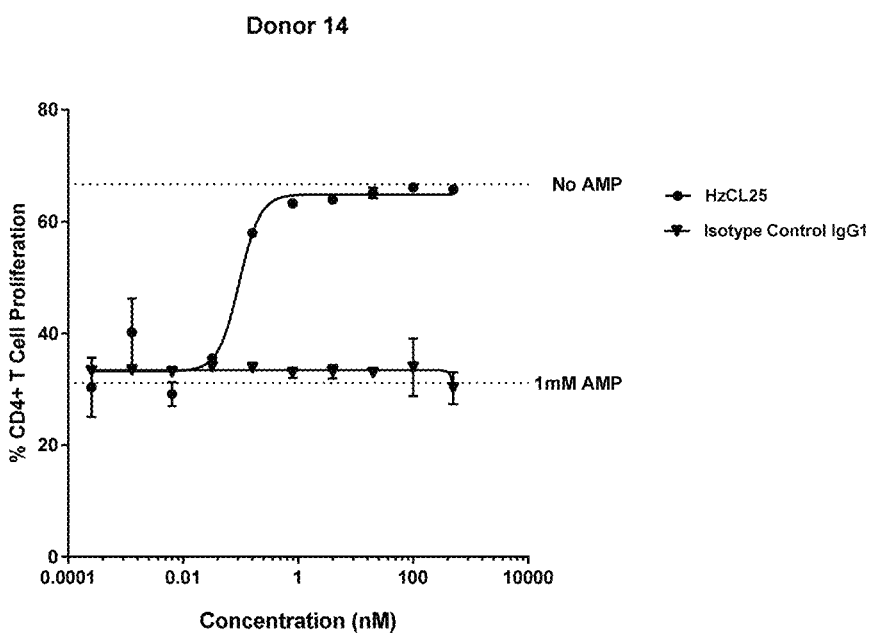

Anti-CD73 antibody reversed AMP-mediated suppression of CD4+ T cell proliferation in a concentration dependent manner in multiple different human donors (FIGS. 5A-5N).

Example 6: Binding Affinity

CD73 enzymatic activity requires substrate binding in the open conformation. After substrate binding, CD73 has to go through a large conformational change from open to closed conformation to convert AMP to adenosine. Antibody binding that inhibits or modulates this conformational change will potentially decrease the rate of AMP to adenosine conversion.

To assess the binding affinity of HzCL25, surface plasmon resonance (SPR) was performed using a Biacore 8K instrument (GE Healthcare) at 25° C. The SPR running buffer (10 mM HEPES, 150 mM NaCl, 3 mM EDTA and 0.05% v/v Surfactant P20, pH 7.4) was prepared from 10×HBS-EP Buffer (GE Healthcare). Anti-human Fc antibodies (GE Healthcare) were immobilized via amine coupling on all sixteen flow cells of an S series sensor chip CM5 (GE Healthcare). The immobilization levels were 9000 RU for all flow cells. The desired capturing level of anti-CD73 antibody was achieved by flowing appropriate concentration of anti-CD73 antibody through the active flow cell of each channel. The non-cleavable ADP analogue APCP (adenosine-5'-(α,β-methylene) diphosphate) with the presence of $Zn^{2+}$ can be used to shift the CD73 conformational equilibrium from open towards closed. Therefore, recombinant CD73 was incubated with SPR running buffer in the presence of 100 μM APCP and 10 μM $ZnCl_2$ (closed SPR running buffer) to study the binding of anti-CD73 antibody to the CD73 in the closed conformation. To achieve this, the ABA injection feature in Biacore 8K was used. For open conformation, the ABA injection sequence started with 60 seconds injection of running buffer. Then, CD73 3-fold serial dilution concentration series prepared from CD73 stock (BPS Bioscience) and running buffer were injected for 180 seconds immediately followed by running buffer for 240 seconds. For closed conformation, the normal SPR running buffer was replaced by closed SPR running buffer. Surface was regenerated with 30 seconds injection of 3 M $MgCl_2$. Binding kinetics and affinity parameters were obtained from a global fit of the data to 1 to 1 binding model. Binding affinities and kinetic association and dissociation rate constants to human, cynomolgus, and mouse CD73 in either open or closed conformations are shown in Table 6 below. The results in Table 6 ensure cynomolgus pharmacokinetic data will reflect human pharmacokinetic data.

Example 8: CD73 Cell Surface Levels

Figure 7:
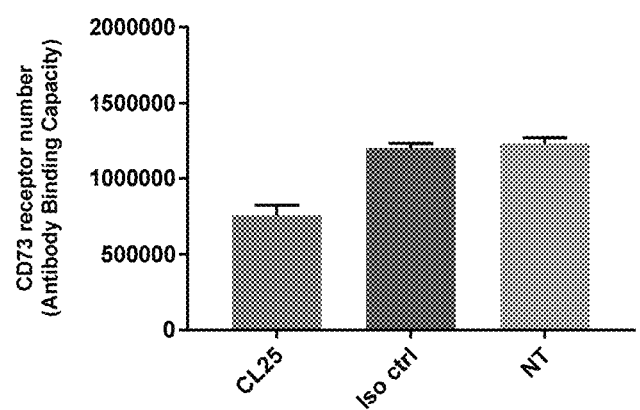
FIG. 7 is a graph depicting surface CD73 levels after 24 hour incubation with the indicated antibody or isotype control (iso ctrl), or without treatment (NT), as measured with a directly conjugated non-competing antibody.

To measure the amount of CD73 on the cell surface after antibody treatment, MDA-MB-231 cells were re-suspended in media (10% FBS RPMI-1640) and plated in 96-well plates at $1\times10^5$ cells/well. Indicated antibodies were added at a final concentration of 10 μg/mL and plates were incubated at 37° C. 5% $CO_2$ for 24 hours. Cells were recovered using Versene and transferred to new 96-well plates. Cells were washed and stained for 30 minutes on ice with 10 μg/mL of non-competing antibody directly conjugated to Dy650. Cells were washed and analyzed by flow cytometry. CD73 cell surface receptor density was determined by Antibody Binding Capacity (ABC) using Quantum Simply Cellular beads. Treatment of cells with CL25 for 24 hours decreased the levels of cell surface CD73 (FIG. 7).

TABLE 6

Binding affinities and kinetic association and dissociation rate constants to human (SEQ ID NO:70), cynomolgus (SEQ ID NO:72), and mouse (SEQ ID NO:71) CD73 in either open or closed conformations for the indicated antibodies (Ab).

| | | Open | | | Closed | | |
|---|---|---|---|---|---|---|---|
| Ab | CD73 | $k_a$ (1/Ms) | $k_d$ (1/s) | $K_D$ (M) | $k_a$ (1/Ms) | $k_d$ (1/s) | $K_D$ (M) |
| CL25 | human | >1E+06 | 3.94E−04 | <3.94E−10 | 9.03E+05 | 3.44E−04 | 3.81E−10 |
| | Cynomolgus | >1E+06 | 6.58E−04 | <6.58E−10 | 9.36E+05 | 4.95E−04 | 5.29E−10 |
| | Murine | No Binding | | | No Binding | | |
| HzCL25 | Human | >1E+06 | 4.49E−04 | <4.49E−10 | Not performed | | |
| | Cynomolgus | >1E+06 | 4.68E−04 | <4.68E−10 | Not performed | | |
| | Murine | No binding | | | Not performed | | |
| CL25_hu_8-4 | Human | 7.70E+05 | 1.76E−03 | 2.29E−09 | Not performed | | |
| CL25_hu_8-5 | Human | >1E+06 | 9.49E−04 | 7.18E−10 | Not performed | | |
| CL25_hu_8-6 | Human | 7.15E+05 | 1.11E−03 | 1.55E−09 | Not performed | | |
| CL25_hu_9-4 | Human | 3.82E+05 | 2.64E−03 | 6.90E−09 | Not performed | | |
| CL25_hu_9-5 | Human | 5.65E+05 | 1.14E−03 | 2.02E−09 | Not performed | | |
| CL25_hu_9-6 | Human | 4.24E+05 | 9.53E−04 | 2.25E−09 | Not performed | | |
| CL25_hu_10-4 | Human | 8.87E+05 | 1.07E−03 | 1.20E−09 | Not performed | | |
| CL25_hu_10-6 | Human | 5.24E+05 | 9.20E−04 | 1.75E−09 | Not performed | | |
| CL25_hu_11-4 | Human | 6.24E+05 | 1.55E−03 | 2.48E−09 | Not performed | | |
| CL25_hu_11-5 | Human | 7.99E+05 | 1.17E−03 | 1.46E−09 | Not performed | | |
| CL25_hu_11-6 | Human | 5.50E+05 | 1.01E−03 | 1.84E−09 | Not performed | | |

Example 7: Epitope Mapping

Figure 6:
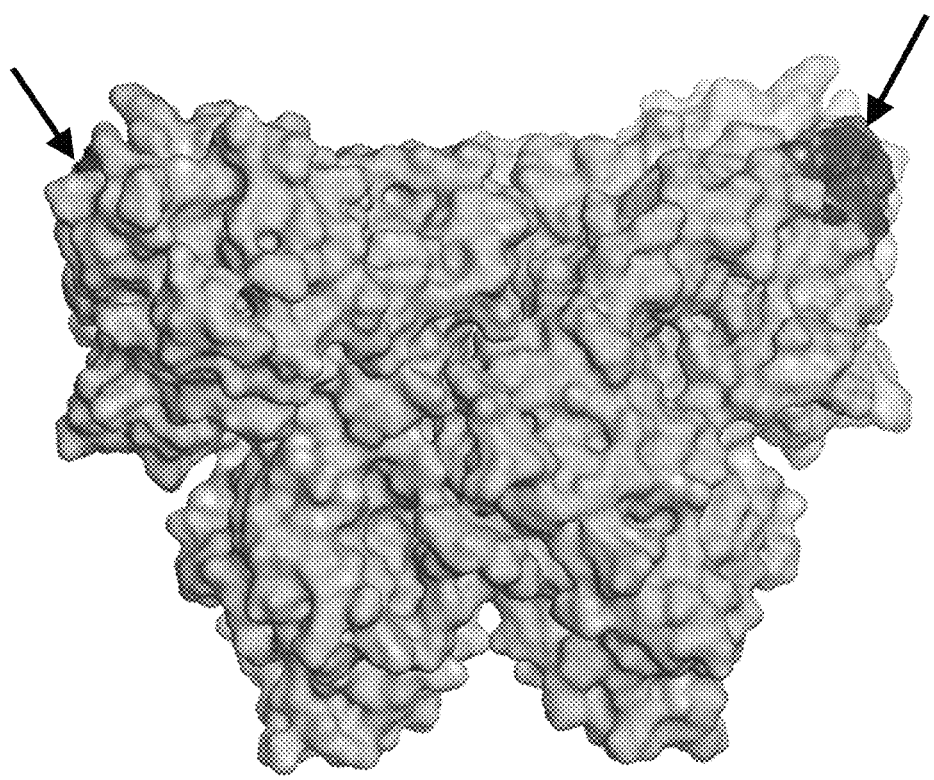
FIG. 6 is a map of the crystal structure of human CD73 (4H2F.pdb) with the CL25 antibody epitope indicated in dark grey (with arrows).

To map the epitope of CL25, Hydrogen-deuterium exchange mass spectrometry (HDX) was performed. CD73 was incubated in deuterium oxide either alone or in complex with CL25 Fab. The deuterium exchange was carried out at 20° C. for 0 seconds, 60 seconds, 600 seconds, or 3600 seconds. The exchange reaction was quenched by low pH and the proteins were digested with pepsin/protease VIII. The deuterium levels at the identified peptides were monitored from the mass shift on LC-MS. The deuterium buildup curves over exchange time for all the peptides were plotted vs time. Peptides with significant reduction in deuterium uptakes upon binding to Fab were assigned as the epitopes for each antibody. The epitope determined by HDX-MS for CL25 is mapped onto the crystal structure of human CD73 (4H2F.pdb) (FIG. 6) and is TKVQQIRRAEPNVL (SEQ ID NO:76) (i.e., amino acids 40-53 of SEQ ID NO:70).

Example 9: Effect of Anti-CD73 Antibody on Tumor Growth

The in vivo efficacy of the CL25 antibody was tested. HzCL25 was suspended in 1× phosphate buffered saline (PBS) (Life Technologies) for intraperitoneal dosing of hu-CD34 NSG mice (Jackson laboratories). 1×PBS and Fc disabled human IgG1 suspended in 1×PBS was included in this study as a control. Mice with humanized immune systems were purchased from Jackson Labs (Bar Harbor, Me.). Briefly, 3 week old female NSG/NOD SCID mice received a single dose of irradiation toxic to immune cell precursors and were then "rescued" by injection of human cord blood, CD34+ selected cells. After 12 weeks (to allow recovery and engraftment of the human immune cells), the mice were received at the AALAS certified vivarium at the Incyte Research Institute. The mice comprised recipients of three distinct human immune donors to better represent individual variations in immune response.

The left flank of the mice were shaved the day prior to inoculation with $5\times10^6$ cells of the human melanoma line A375 (ATCC, Manassas Va.) suspended in matrigel (Corning Life Sciences, Tewksbury, Mass.). On day 11, tumor dimensions were measured by Vernier calipers, and volume estimated by the formula Volume=[L (long dimension)×W2 (short dimension)]/2. Mice were randomized into 3 groups of 5 or 6 mice of approximate mean volume (~200 mm³) and donor representation. Tumors were measured every 2-4 days for the duration of the study.

HzCL25 was diluted in PBS to concentrations of 1 and 0.1 mg/ml, and a matching isotype control (cx00376-001), was diluted to 1 mg/ml fresh on the morning of administration. Every six days, from day 11, antibody was given to the mice by intraperitoneal injection at 10 ml/kg, achieving effective doses of 1 and 10 mg/kg of body weight. A total of three doses were given.

Forty-eight hours after the third and final dose, mice were euthanized by $CO_2$ asphyxiation. Tumors were excised, placed into media containing proteases, placed on ice, and then disrupted into single cell suspensions by use of the GentleMacs Tissue Disruptor (Miltenyi, Auburn CA). The cells remained on ice while being processed for flow cytometry and enzymatic assay.

Figure 8:
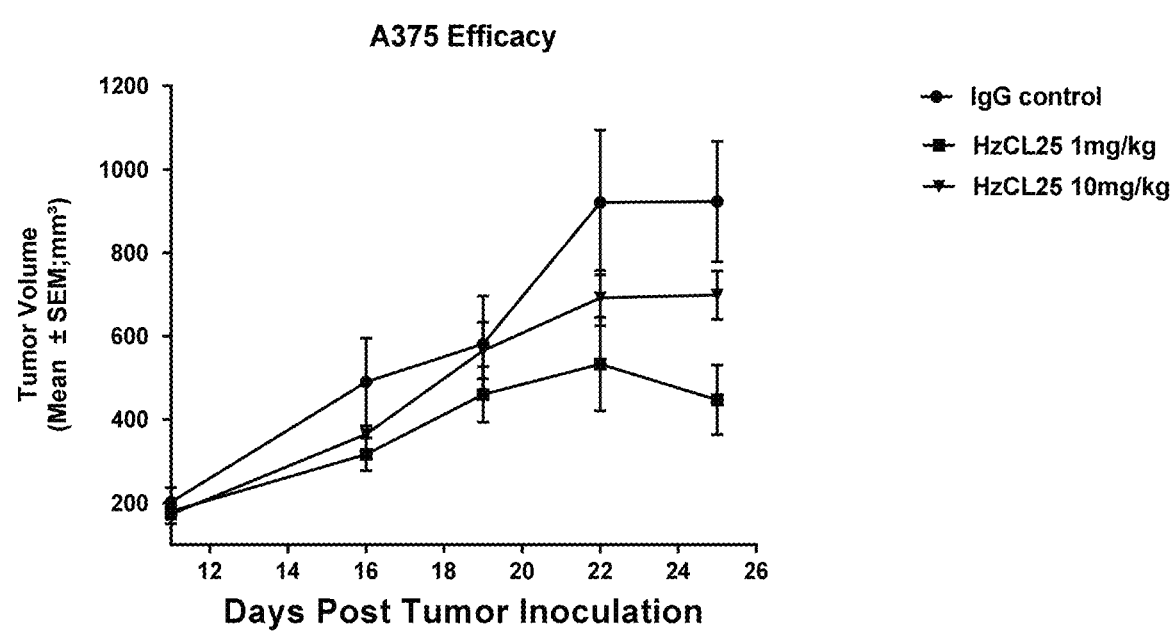
FIG. 8 is a graph depicting the mean tumor volume at the indicated days post tumor inoculation for mice administered isotype control (IgG control) or 1 mg/kg or 10 mg/kg of HzCL25.

Mice administered HzCL25 exhibited tumor growth inhibition at both doses; the low dose significantly (p=0.026, two tailed t test) slowed growth 56% (FIG. 8).

Example 10: Ex Vivo Enzymatic Activity Assay

Figure 9:
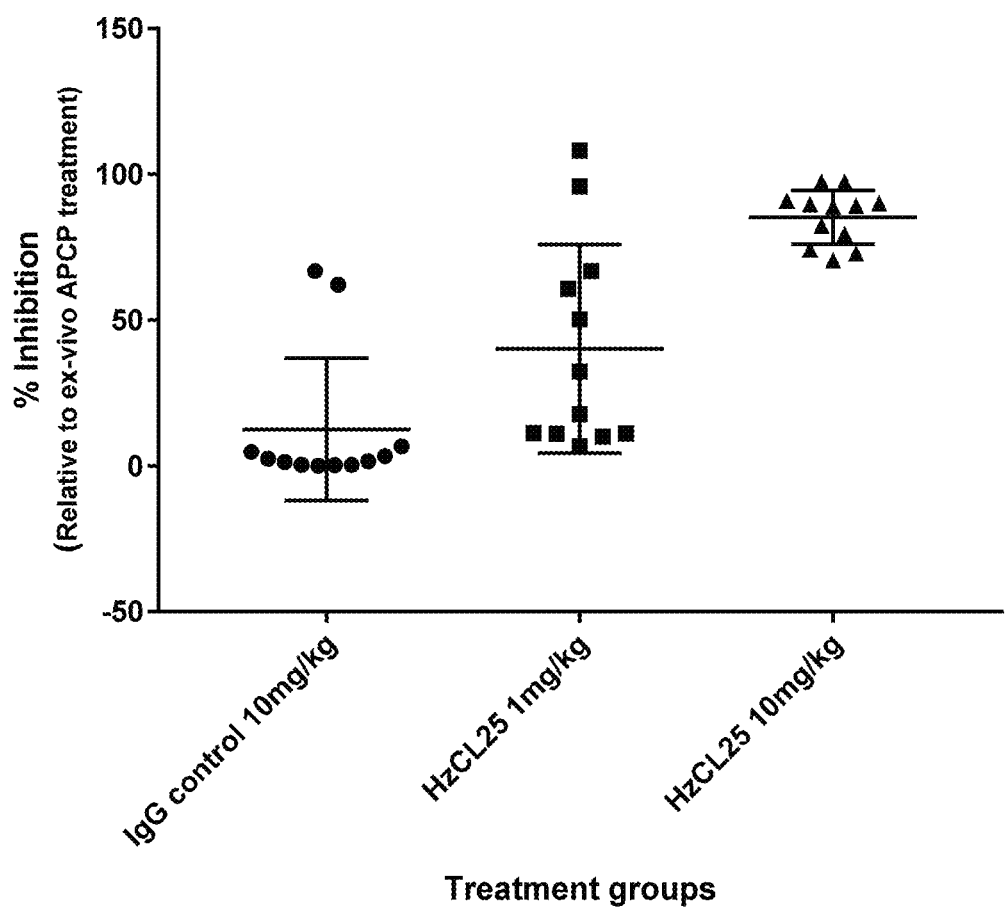
FIG. 9 is a graph depicting the percent inhibition of CD73 in tumors harvested from mice treated administered isotype control (IgG control) or 1 mg/kg or 10 mg/kg of HzCL25.

To evaluate the enzymatic activity of CD73 in tumor-bearing mice administered HzCL25, single cell suspension of the tumor homogenates from the experiment of FIG. 8 were sorted for live cells using Dead Cell Removal MicroBeads (Miltenyi Biotec). Post cell selection, 10,000 live cells per well were plated with 100 µM of AMP. As a positive control, 250 µM APCP treated cells were used. Following treatment, AMP-glo kit (Promega; Cat. #V5011) was used to detect enzymatic activity of CD73 as per the manufacturer's guidelines. Luminescence was used as a measure for AMP level detection and readouts from each animal were normalized to APCP-treated culture readouts, where APCP-treated cultures were considered to demonstrate maximum inhibition of CD73 activity (FIG. 9). As shown in FIG. 9, HzCL25 demonstrated a dose-dependent inhibition of CD73 enzymatic activity upon tumor cells.

Example 11: Free Surface CD73 of Anti-CD73-Treated Tumors

Figure 10A:
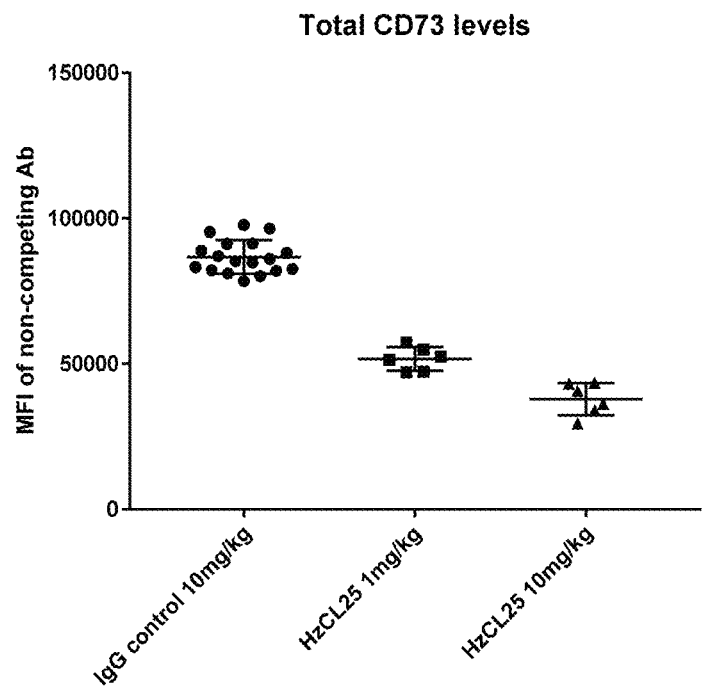
FIG. 10A is a graph depicting the total surface CD73 levels for single cell suspensions of tumor cells only from mice treated with the indicated antibodies at the indicated doses, as determined by the mean fluorescence intensity (MFI) of non-competing antibody.
Figure 10B:
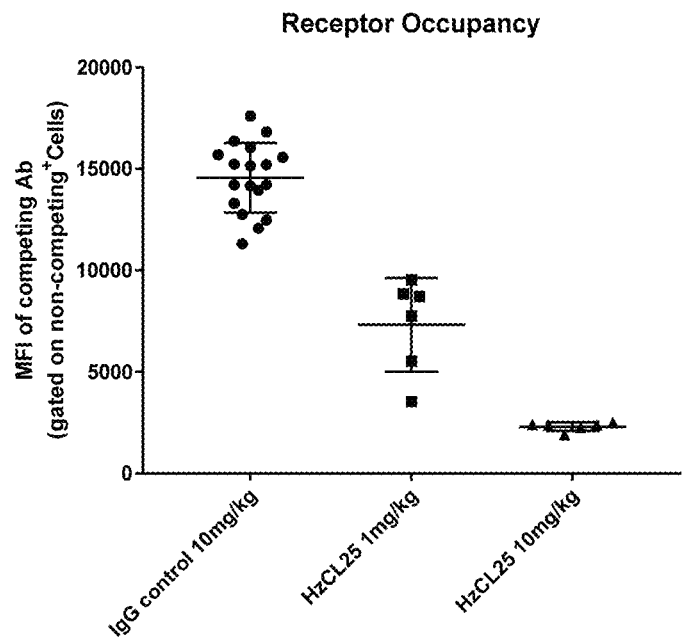
FIG. 10B is a graph depicting the receptor occupancy for single cell suspensions of tumor cells only from mice treated with the indicated antibodies at the indicated doses, as determined by the MFI of competing antibody.

To evaluate the receptor coverage post-treatment, single cell suspensions of tumor homogenates from the experiment of FIG. 8 were stained with fluorochrome-conjugated antibodies against viability dye (Biolegend, Cat. #423110), human CD45 (Biolegend, Cat. #304036), mouse CD45 (BD Biosciences, Cat. #563410), mouse CD90.2 (BD Biosciences, Cat. #565257), and competing (AF488-conjugated CL25 antibody) or non-competing antibody (PE-conjugated Antibody X). Cells were run and analyzed using BD FACSymphony flow cytometry analyzer and FlowJo software package respectively. Analysis was performed by gating on live cell population, followed by mouse cells and human immune cell exclusion, focusing on the tumor cell population. Total CD73 levels on tumor cells were detected using fluorophore tagged non-competing CD73 antibody. In a dose-dependent manner, HzCL25 decreased the total CD73 levels on tumor cells (FIG. 10A). Of the cells expressing CD73 as measured in FIG. 10A, free surface CD73 was measured using a fluorophore tagged competing (CL25) antibody (FIG. 10B). HzCL25 treatment demonstrated a dose-dependent decrease in free surface CD73 (FIG. 10B). Furthermore, this reduction in free surface CD73 levels for both dosages was significantly lower compared to IgG treated tumors (FIG. 10B).

Figure 11A:
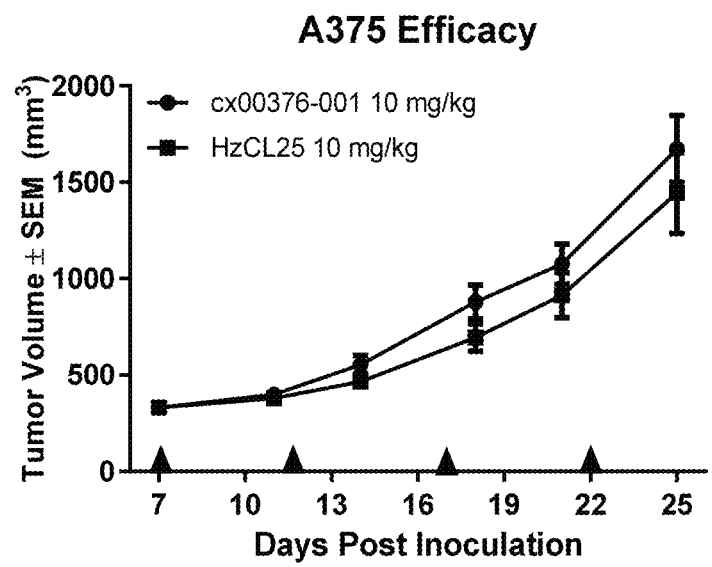
FIG. 11A is a graph depicting the mean tumor volume at the indicated days post-inoculation with 10 mg/kg of isotype control (cx00376-001) or HzCL25. Triangles on the x-axis indicate days of drug administration.
Figure 11B:
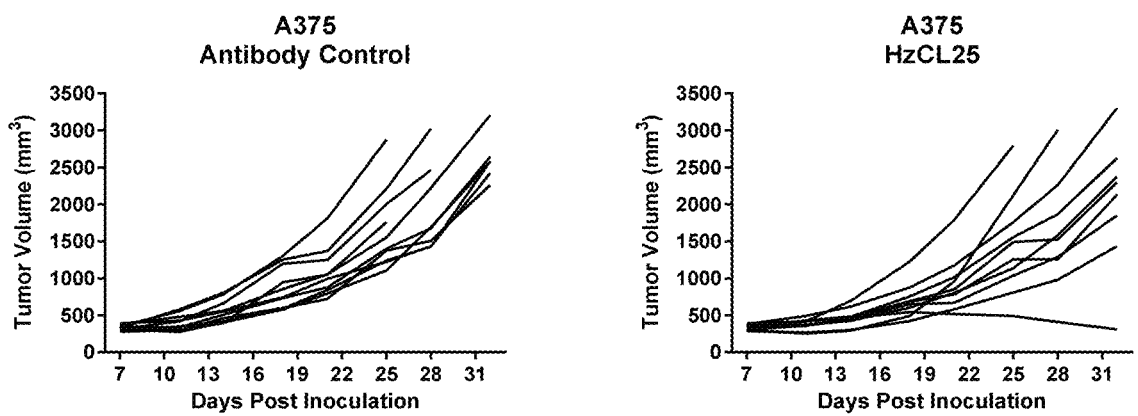
FIG. 11B is a graph depicting the individual tumor volume through day 33 for the mice of FIG. 11A treated with isotype control (left) or HzCL25 (right).

Example 12: Pharmacokinetic and Pharmacodynamics In Vivo Studies of Anti-CD73 Antibody To assess the efficacy of HzCL25 in vivo, female human CD34⁺ reconstituted mice (21 weeks of age; The Jackson Laboratory, Bar Harbor, Me.) were inoculated subcutaneously with 5×10⁶ A375 human melanoma cells (ATCC #CRL-1619). The treatment of tumor-bearing mice was started 7 days post-inoculation, when tumor volume reached approximately 330 mm³. A375 engrafted humanized NSG mice were dosed intraperitoneally with HzCL25 at 10 mg/kg every 5 days. The study animals received 6 total doses of antibody, with the final dose on day 32. Tumors were collected from mice with tumors greater than 10% of their body weight on days 26 and 29, and from all remaining animals on day 33. Serum was collected from all animals on day 26, again from mice with tumors greater than 10% of their body weight on day 29, and from all remaining animals on day 33. Through 26 days (at which time the control IgG group had reached its mean efficacy endpoint), HzCL25 provided modest but insignificant tumor growth inhibition of 14% (FIG. 11A). However, extended dosing through 32 days showed marked differences in tumor growth rates and survival between HzCL25-treated animals and those remaining mice receiving the IgG control (FIG. 11B).

A separate pharmacodynamic (PD) study was initiated on day 22 with HzCL25 at 10 mg/kg every 3 days for a total of 2 doses of antibody. Tumors from PD animals were collected on day 27, 48 hours post-second antibody dose. To measure soluble human CD73 (hCD73) in mouse sera following antibody treatment, MSD plates were coated with a non-competing capture IgG antibody at 1 µg/mL and incubated at 4° C. overnight. Plates were washed and 1:5 diluted mouse serum samples were added. A standard curve was generated using recombinant human CD73 (rhuCD73). Plates were incubated for 2 hours at room temperature with shaking at 600 rpm. Plates were washed and competing (HzCL25) or non-competing (Antibody X) antibodies directly conjugated to sulfo-tag were added to the plate at 1 µg/mL and incubated for 1 hour at room temperature with shaking at 600 rpm. Plates were washed and 150 µL of Read Buffer were added and analyzed using an MSD plate reader. Soluble hCD73 levels from mouse sera were calculated from the standard curve. Although treatment with HzCL25 slightly stabilized soluble human CD73 in mice, the level of soluble human CD73 was still far below the level of antibody in the mice (FIG. 12).

Example 13: Generation of Anti-Human CD73 Monoclonal Antibody 3-F03

To generate additional anti-human CD73 monoclonal antibodies, multiple selection rounds of a single donor library were performed. The library of approximately 1.5E12 phage particles was enriched over three rounds of panning using 200 nM biotinylated human CD73 (SEQ ID NO:70). The scFv cassettes from this pool were then recombined into a yeast display vector and a library of approximately 5.4E7 was created. This library was selected by FACS for three rounds using 100 nM biotinylated murine CD73 (SEQ ID NO:71). Unique sequences were obtained from the final sorting output by Sanger sequencing of yeast colonies. The yeast 3-F03 scFv sequence was identified from this pool and contained a VH of the amino acid sequence set forth in SEQ ID NO:77 and a VL of the amino acid sequence set forth in SEQ ID NO:65.

To construct a full-length human 3-F03 antibody, the yeast 3-F03 scFv sequences were modified prior to cloning into a human IgG1 scaffold comprising the human IgG1 constant region set forth in SEQ ID NO:73 and the human kappa light chain constant region set forth in SEQ ID NO:74. For the VH, the N-terminal glutamate (E) of SEQ ID NO:77 was removed and the threonine (T) at Kabat position H77 of SEQ ID NO:77 (i.e., position 78 of SEQ ID NO:77) was substituted with an alanine (A). For the VL, the N-terminal alanine (A) of SEQ ID NO:65 was removed. The resulting full-length human 3-F03 antibody contains the VH and VL set forth in the amino acid sequences of SEQ ID NOs:60 and 61, respectively. The resulting full-length human 3-F03 antibody contains the heavy chain and light chain set forth in the amino acid sequences of SEQ ID NOs: 66 and 31, respectively. This antibody is referred to herein as "3-F03". Table 3, above, shows the amino acid sequences of the 3-F03 CDRs according to IMGT, Chothia, AbM, Kabat, and Contact numbering and of the mature VH, VL, heavy chain, and light chain.

Example 14: Binding of 3-F03 to Cell Surface CD73

Figure 13A:
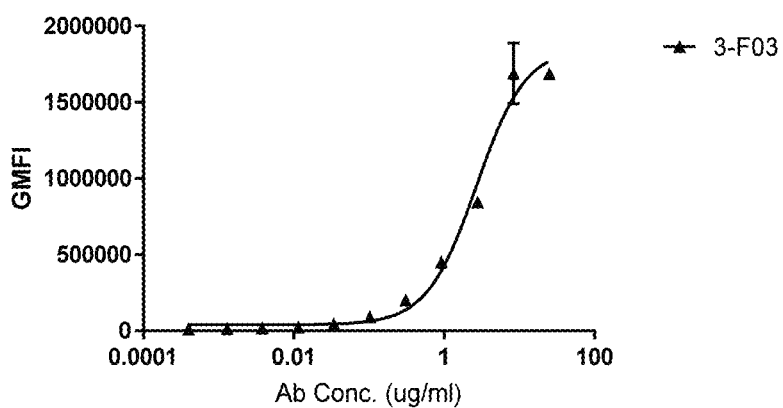
FIG. 13A is a graph depicting the cell binding (GMFI) for antibody 3-F03 at the indicated concentrations on MDA-MB-231 cells.
Figure 13B:
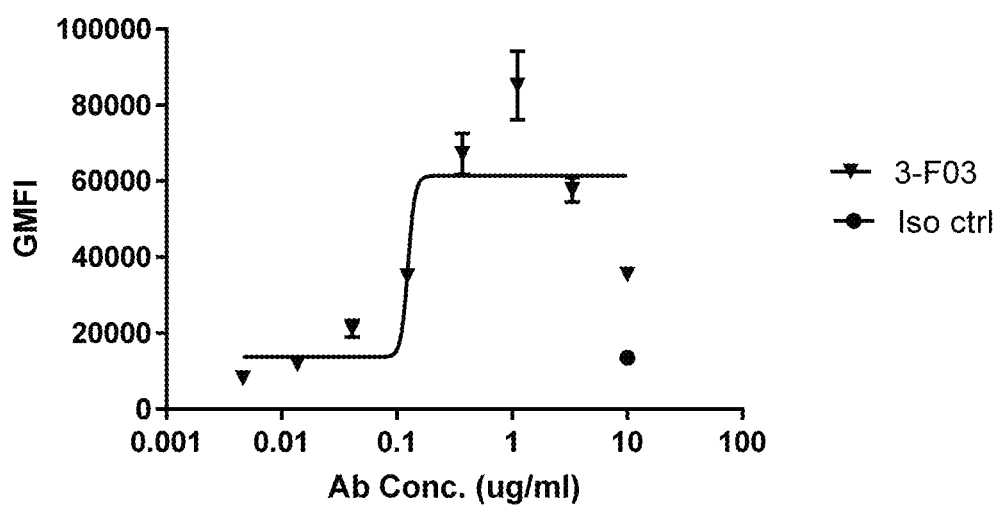
FIG. 13B is a graph depicting the cell binding (measured by GMFI) for 3-F03 or isotype control (Iso ctrl) at the indicated concentrations on A375 cells.

The binding of 3-F03 to cell surface CD73 was performed as described in Example 2, above. 3-F03 displays high potency binding to cells with high levels of surface CD73 (MDA-MB-231), and moderate levels of CD73 (A375 cells) (FIG. 13A and FIG. 13B).

Example 15: 3-F03-Mediated Cellular CD73 Inhibition

The ability of 3-F03 to inhibit CD73 activity on cells was evaluated as described in Example 3, above. Results are depicted in FIG. 14A and FIG. 14B.

Figure 14A:
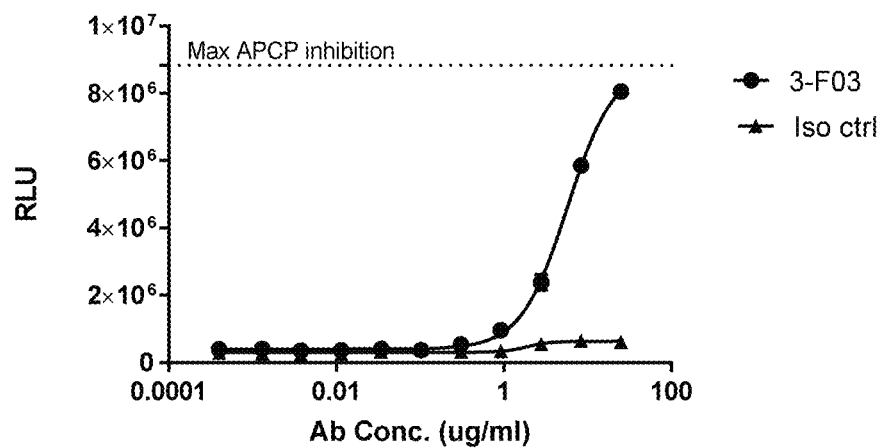
FIG. 14A is a graph depicting the cellular CD73 inhibition on A375 cells treated with 3-F03 or isotype control (Iso ctrl) at the indicated concentrations.
Figure 14B:
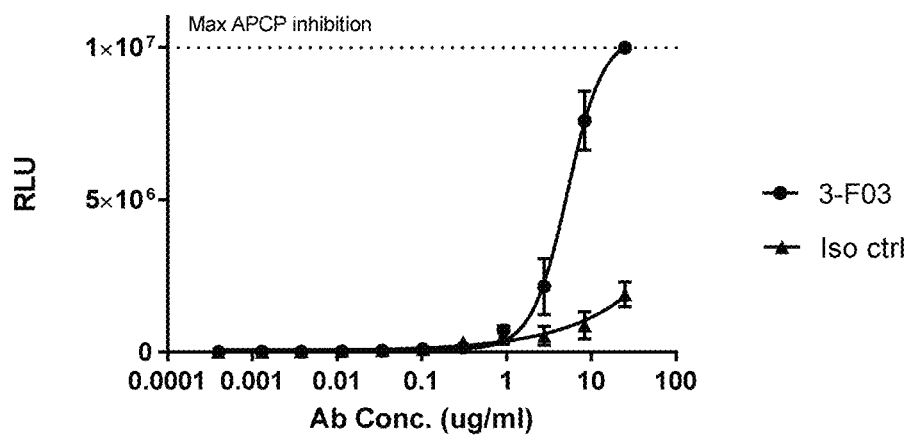
FIG. 14B is a graph depicting the cellular CD73 inhibition on MDA-MB-231 cells treated with 3-F03 or isotype control (Iso ctrl) at the indicated concentrations.

Clone 3-F03 showed maximum inhibition of cellular CD73 in both tested cell types as compared to the small molecule inhibitor of CD73, APCP (FIG. 14A and FIG. 14B).

Example 16: 3-F03-Mediated Soluble CD73 Inhibition

The ability of 3-F03 to inhibit CD73 activity of recombinant protein was evaluated as described in Example 4, above, except that 0.025 ug/mL of rhuCD73 was used.

Figure 15:
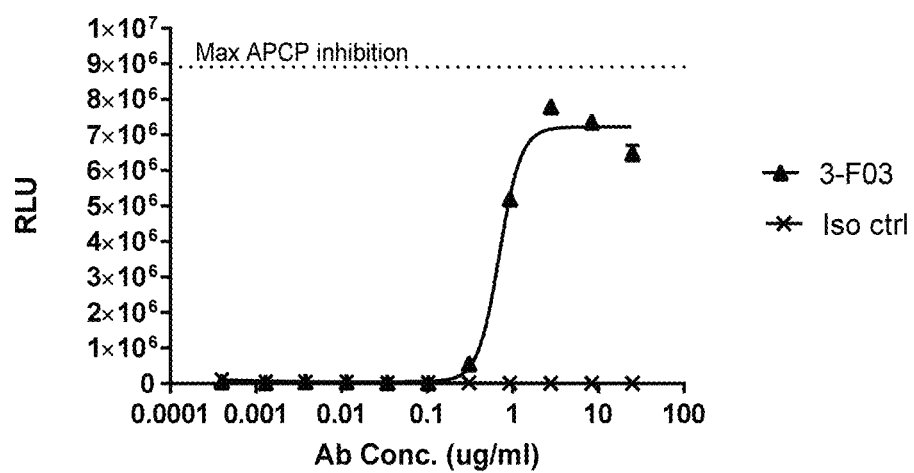
FIG. 15 is a graph depicting inhibition of recombinant CD73 treated with 3-F03 or isotype control (Iso control) at the indicated concentrations.
Figure 16A:
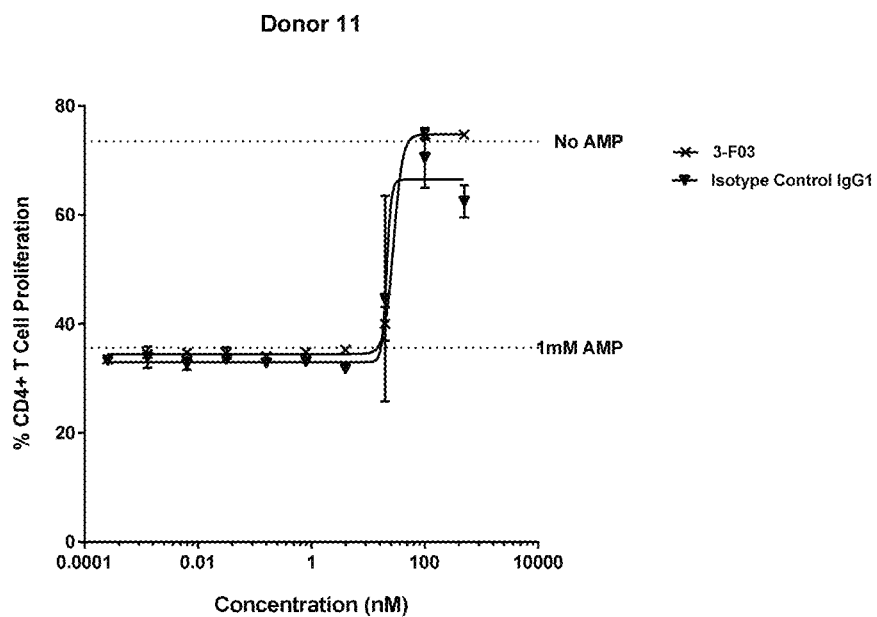
FIGS. 16A-16D are each graphs depicting the percent CD4+ T cell proliferation in donor cells treated with the 3-F03 antibody or isotype control at various concentrations.
Figure 16B:
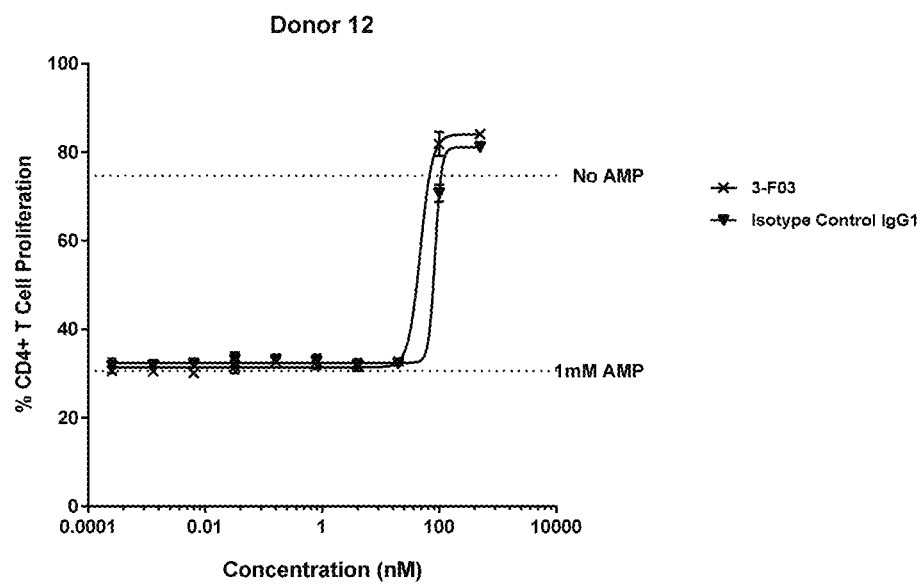
Figure 16C:
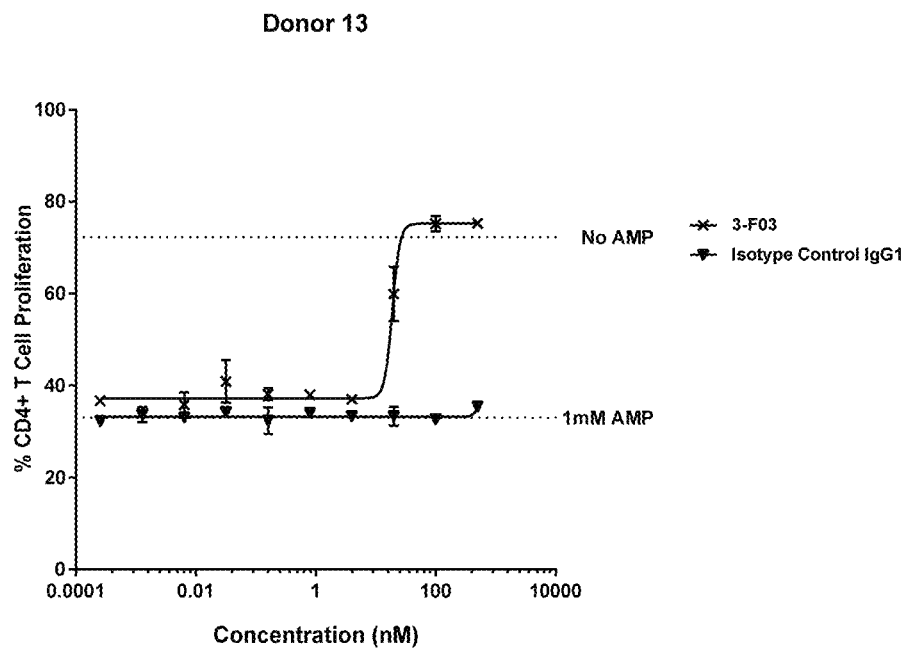
Figure 16D:
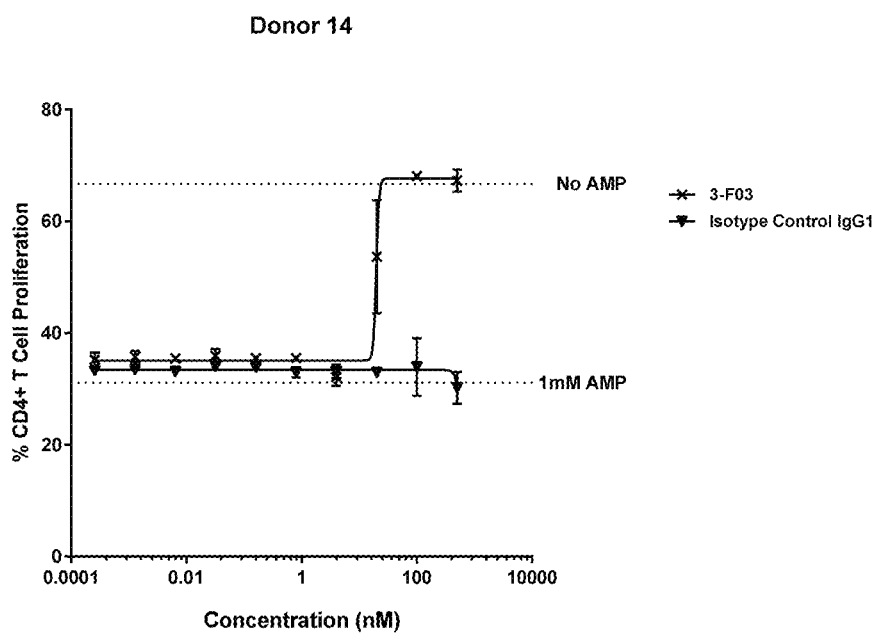

Results are depicted in FIG. 15. Antibody 3-F03 had good potency (FIG. 15). Antibody 3-F03 did not exhibit any hook-effect.

Example 17: Anti-Human CD73 Monoclonal Antibody-Mediated Reversal of AMP-Mediated Suppression of T Cell Proliferation The ability of 3-F03 to reverse AMP-mediated suppression of T cell proliferation was evaluated as described in Example 5, above. 3-F03 reversed AMP-mediated suppression of CD4+ T cell proliferation in a concentration dependent manner in multiple different human donors (FIGS. 16A-16D).

Example 18: Binding Affinity of Anti-CD73 Antibody

The binding affinity of 3-F03 was evaluated as described in Example 6, above. Binding affinities and kinetic association and dissociation rate constants to human, cynomolgus, and mouse CD73 in either open or closed conformations are shown in Table 7 below.

TABLE 7

Binding affinities and kinetic association and dissociation rate constants to human, cynomolgus, and mouse CD73 in either open or closed conformations.

| Sample | | Open | | | Closed | | |
|---|---|---|---|---|---|---|---|
| Name | CD73 | $k_a$ (1/Ms) | $k_d$ (1/s) | $K_D$ (M) | $k_a$ (1/Ms) | $k_d$ (1/s) | $K_D$ (M) |
| 3-F03 | human | 2.15E+05 | 7.96E−05 | 3.70E−10 | No Binding | | |
| | Cynomolgus | 3.01E+05 | 2.21E−04 | 7.34E−10 | No Binding | | |
| | Murine | 2.17E+05 | 3.60E−04 | 1.66E−09 | No Binding | | |

Example 19: Epitope Mapping of 3-F03

Figure 17:
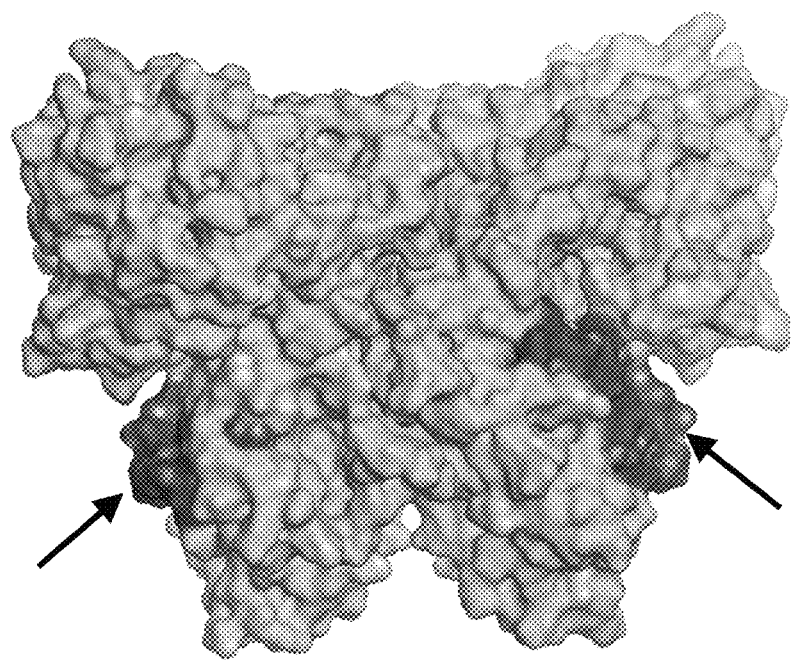
FIG. 17 is a map of the crystal structure of human CD73 (4H2F.pdb) with the 3-F03 antibody epitope indicated in dark grey (with arrows).

The epitope of 3-F03 was mapped as described in Example 7, above. The epitopes determined by HDX-MS for 3-F03 are mapped onto the crystal structure of human CD73 (4H2F.pdb) (FIG. 17) and are AAVLPFGGTFDLVQ (SEQ ID NO:78) (i.e., amino acids 386-399 of SEQ ID NO:70) and ILPNFLANGGDGFQMIKDEL (SEQ ID NO:79) (i.e., amino acids 470-489 of SEQ ID NO:70).

Example 20: Effect of 3-F03 on CD73 Cell Surface Levels

Figure 18:
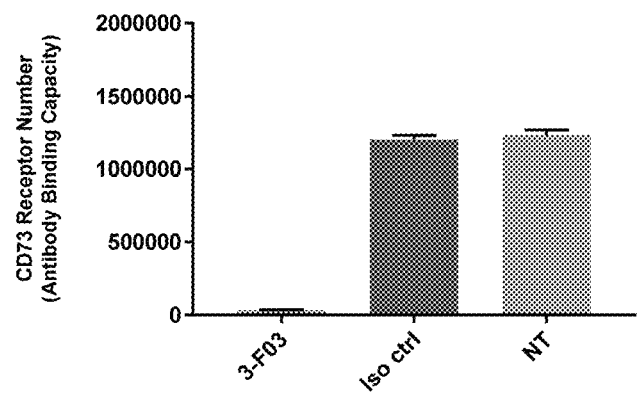
FIG. 18 is a graph depicting CD73 surface levels after 24 hour incubation with 3-F03, isotype control (iso ctrl), or not treated (NT) as measured with a directly conjugated non-competing antibody, CL43-Dy650.

The amount of CD73 on the cell surface after treatment with 3-F03 was evaluated as described in Example 8, above. 3-F03 dramatically decreased the level of detectable CD73 on the cell surface compared to an isotype control antibody or non-treated cells (FIG. 18).

Example 21: In Vivo Studies

Figure 19A:
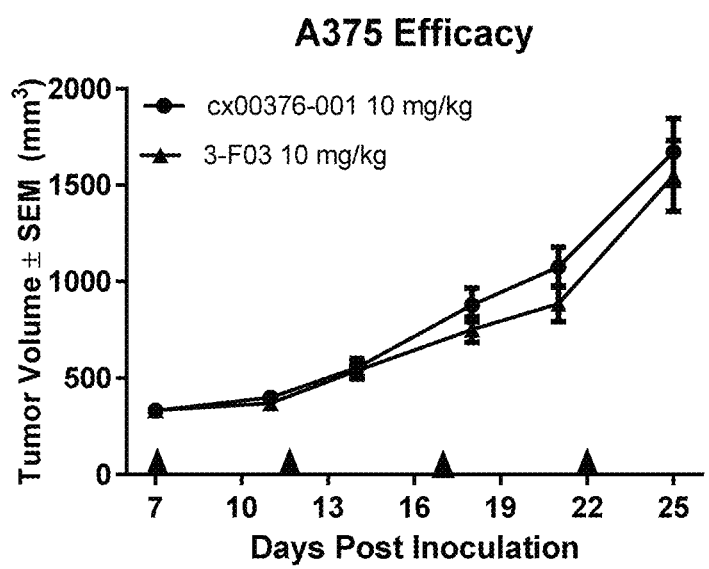
FIG. 19A is a graph depicting the mean tumor volume at the indicated days post-inoculation with 10 mg/kg of isotype control (cx00376-001) or 3-F03. Triangles on x-axis indicate days of drug administration.
Figure 19B:
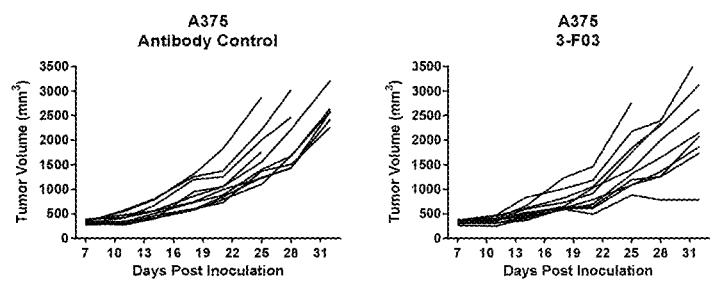
FIG. 19B is a graph depicting the individual tumor volume through day 33 for the mice of FIG. 19A treated with isotype control (left) or 3-F03 (right).

The in vivo efficacy of 3-F03 was evaluated as described in Example 12, above. Through 26 days, at which time, the control IgG group had reached its mean efficacy endpoint, 3-F03 provided modest but statistically insignificant tumor growth inhibition of 8% (FIG. 19A). However, extended dosing through 32 days showed marked differences in tumor growth rates and survival between 3-F03 treated animals and those remaining mice receiving the IgG control (FIG. 19B).

The PD properties of 3-F03 were also evaluated as described in Example 12, above. Treatment with 3-F03 did not stabilize soluble human CD73 in mice, as there was no detectable increase in total or free soluble human CD73 upon treatment with 3-F03 (FIG. 20).

Example 22: 3-F03 Variants

Sequences of the 3-F03 light chain (LC, SEQ ID NO:66) and heavy chain (HC, SEQ ID NO:31) were used to construct a homology model. FIG. 21A-FIG. 21J provide the amino acid sequences of the VH and VL of exemplary 3-F03 variants. Antibodies comprising these VH and VL sequences contained the heavy chain constant region set forth in SEQ ID NO:73 and light chain constant region set forth in SEQ ID NO:74. Table 8 provides the binding affinity and kinetics of the exemplary 3-F03 variants. None of the mutations tested dramatically impacted binding to CD73 by Biacore. All tested mutations had affinities within tenfold of the 3-F03 antibody, with the majority within two fold of 3-F03.

confirm the Biacore studies (Table 8): these mutations did not dramatically alter human CD73 binding for these variant clones.

Figure 23:
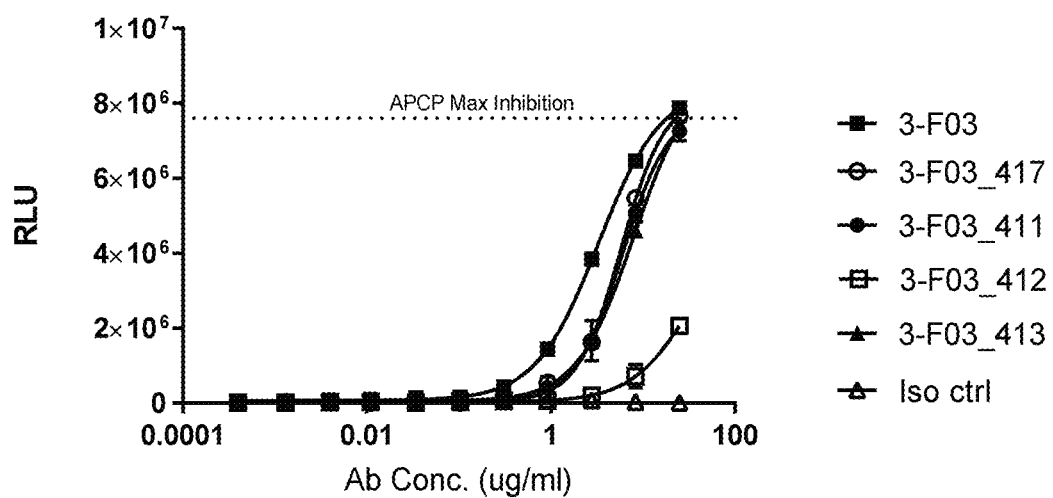
FIG. 23 is a graph depicting the cellular CD73 inhibition on MDA-MB-231 cells treated with the indicated antibodies or isotype control at the indicated concentrations.

To test the ability of 3-F03 variants to inhibit CD73 activity on cells, MDA-MB-231 cells were washed with serum free RPMI media and plated $1\times10^4$ cells/well in 96-well plates. Cells were incubated with the indicated concentration of antibodies or APCP at 37° C. 5% $CO_2$ for 30 minutes. Next, AMP was added to a final concentration of 100 μM and cells were incubated an additional 3 hours at 37° C. 5% $CO_2$. Plates were centrifuged for 1-2 minutes at 300 g and 25 μL of supernatant was transferred into a new 96-well plates. AMP-Glo Assay was used according to the manufacturer's instructions. RLU is a directly correlated with the AMP concentration in this assay. 3-F03 showed maximum inhibition among the 3-F03 variants (FIG. 23). Variants 3-F03_417, 3-F03_411 and 3-F03_413 displayed

TABLE 8

Biacore binding affinity and kinetics of 3-F03 variants. — = absent.

| | Mutation made (kabat numbering) | | | | | |
|---|---|---|---|---|---|---|
| Sample Name | VH1 (E or —) | VH53 (D, E, or S) | VH77 (A or T) | VL1 (A, D, or —) | $k_a$ (1/Ms) | $k_d$ (1/s) | $K_D$ (M) |
| 3-F03_396 | E | D | T | A | 1.39E+05 | 1.78E−04 | 1.28E−09 |
| 3-F03_408 | E | D | T | — | 1.40E+05 | 1.86E−04 | 1.33E−09 |
| 3-F03_402 | — | D | T | A | 1.32E+05 | 1.84E−04 | 1.39E−09 |
| 3-F03_384 | E | D | T | D | 1.40E+05 | 1.98E−04 | 1.41E−09 |
| 3-F03_399 | E | D | A | A | 1.38E+05 | 1.97E−04 | 1.43E−09 |
| 3-F03_411 | E | D | A | — | 1.39E+05 | 2.04E−04 | 1.47E−09 |
| 3-F03_414 | — | D | T | — | 1.31E+05 | 1.98E−04 | 1.51E−09 |
| 3-F03_390 | — | D | T | D | 1.29E+05 | 2.12E−04 | 1.64E−09 |
| 3-F03_398 | E | E | T | A | 9.26E+04 | 1.59E−04 | 1.71E−09 |
| 3-F03_387 | E | D | A | D | 1.37E+05 | 2.38E−04 | 1.74E−09 |
| 3-F03_386 | E | E | T | D | 9.23E+04 | 1.64E−04 | 1.78E−09 |
| 3-F03_401 | E | E | A | A | 9.15E+04 | 1.67E−04 | 1.82E−09 |
| 3-F03_413 | E | E | A | — | 9.13E+04 | 1.71E−04 | 1.88E−09 |
| 3-F03_405 | — | D | A | A | 1.26E+05 | 2.39E−04 | 1.90E−09 |
| 3-F03_410 | E | E | T | — | 9.01E+04 | 1.76E−04 | 1.95E−09 |
| 3-F03_389 | E | E | A | D | 9.17E+04 | 1.89E−04 | 2.06E−09 |
| 3-F03_393 | — | D | A | D | 1.14E+05 | 2.39E−04 | 2.09E−09 |
| 3-F03_417 | — | D | A | — | 1.34E+05 | 2.84E−04 | 2.12E−09 |
| 3-F03_392 | — | E | T | D | 8.08E+04 | 1.80E−04 | 2.23E−09 |
| 3-F03_404 | — | E | T | A | 8.35E+04 | 1.89E−04 | 2.26E−09 |
| 3-F03_419 | — | E | A | — | 8.28E+04 | 2.00E−04 | 2.41E−09 |
| 3-F03_416 | — | E | T | — | 9.01E+04 | 2.21E−04 | 2.45E−09 |
| 3-F03_407 | — | E | A | A | 8.74E+04 | 2.35E−04 | 2.69E−09 |
| 3-F03_395 | — | E | A | D | 7.12E+04 | 2.10E−04 | 2.94E−09 |
| 3-F03_388 | E | S | A | D | 1.15E+05 | 8.68E−04 | 7.56E−09 |
| 3-F03_397 | E | S | T | A | 6.07E+04 | 4.89E−04 | 8.04E−09 |
| 3-F03_385 | E | S | T | D | 6.33E+04 | 5.38E−04 | 8.50E−09 |
| 3-F03_400 | E | S | A | A | 6.15E+04 | 5.29E−04 | 8.60E−09 |
| 3-F03_409 | E | S | T | — | 6.02E+04 | 5.46E−04 | 9.06E−09 |
| 3-F03_403 | — | S | T | A | 5.79E+04 | 5.41E−04 | 9.34E−09 |
| 3-F03_415 | — | S | T | — | 5.99E+04 | 6.06E−04 | 1.01E−08 |
| 3-F03_391 | — | S | T | D | 5.69E+04 | 5.84E−04 | 1.03E−08 |
| 3-F03_406 | — | S | A | A | 7.41E+04 | 7.65E−04 | 1.03E−08 |
| 3-F03_412 | E | S | A | — | 5.27E+04 | 6.38E−04 | 1.21E−08 |
| 3-F03_394 | — | S | A | D | 4.84E+04 | 6.30E−04 | 1.30E−08 |
| 3-F03_418 | — | S | A | — | 5.55E+04 | 7.99E−04 | 1.44E−08 |

Figure 22:
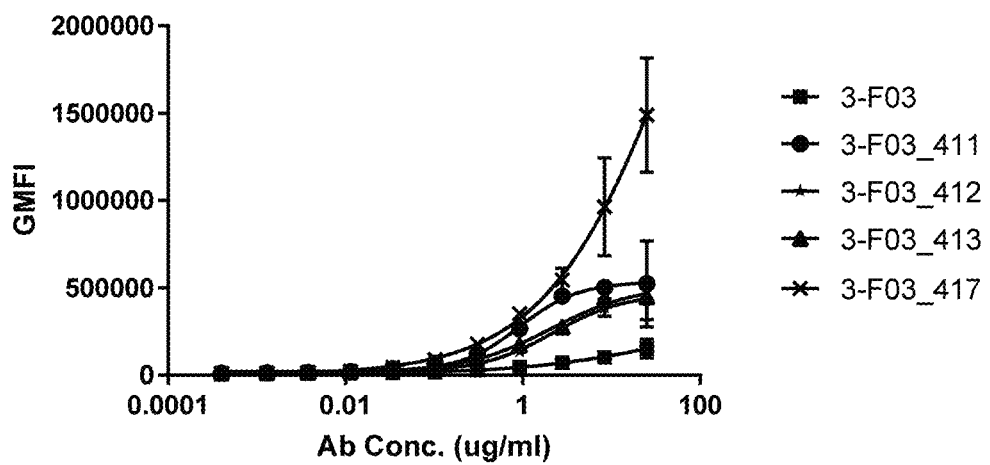
FIG. 22 is a graph depicting cell binding (GMFI) for the indicated antibodies at the indicated concentrations on MDA-MB-231 cells.

To test the binding of engineered 3-F03 variants to cell surface CD73, MDA-MB-231 cells were washed and added to 96-well plates at $5\times10^4$ cells/well. Cells were stained with the indicated concentration of antibodies for 1 hour on ice. Cells were then washed and stained goat anti-mouse secondary conjugated to PE for 30 minute on ice. Cells were then washed and analyzed by flow cytometry. The GMFI of CD73 staining is graphed (FIG. 22). Each of the 3-F03 variants had a similar binding profile, except for 3-F03_417, which showed a slightly higher Ymax (FIG. 22). These data slightly lower potency compared to 3-F03 (FIG. 23). Variant 3-F03_412 did not inhibit membrane bound CD73 on MDA-MB-231 cells (FIG. 23).

Example 23: Tumor Adenosine Levels of Anti-CD73 Antibody-Treated Tumors

The ability of HzCL25 and 3-F03 to modulate intratumoral adenosine was assessed in vivo. Female human CD34+ reconstituted mice (29 weeks of age; The Jackson Laboratory, Bar Harbor, ME) were inoculated subcutaneously with 3×10⁶ MDA-MB-231 cells (ATCC #HTB-26), suspended in matrigel (Corning Life Sciences) on their left flank, with three mice per treatment group. The treatment of tumor-bearing mice was started 10 days post inoculation, when tumor volume reached approximately 240 mm³. HzCL25, 3-F03 or an IgG isotype control was diluted to 1 mg/ml in phosphate-buffered saline (PBS) and administered to mice by intraperitoneal injection at a dose of 10 mg/kg on day 12, and again, 5 days later on day 17. On day 18, mice were euthanized, tumors excised, placed into cryo-tubes and flash frozen in liquid nitrogen.

To determine adenosine concentration in the tumors, frozen tissue samples were sectioned and subjected to quantitative MALDI mass spectrometry imaging (MSI) in triplicate at 80 μm spatial resolution. Based on the MSI datasets acquired from the tissue sections and a dilution series of standards spotted onto control sections, the quantification of adenosine in selected tissue sections was obtained with multi-imaging software. A correlation between the calibration curve and the signal obtained was made to determine the concentration of analytes in each region of interest. Tumor containing regions of interest were identified by H&E staining of serial sections.

Figure 26:
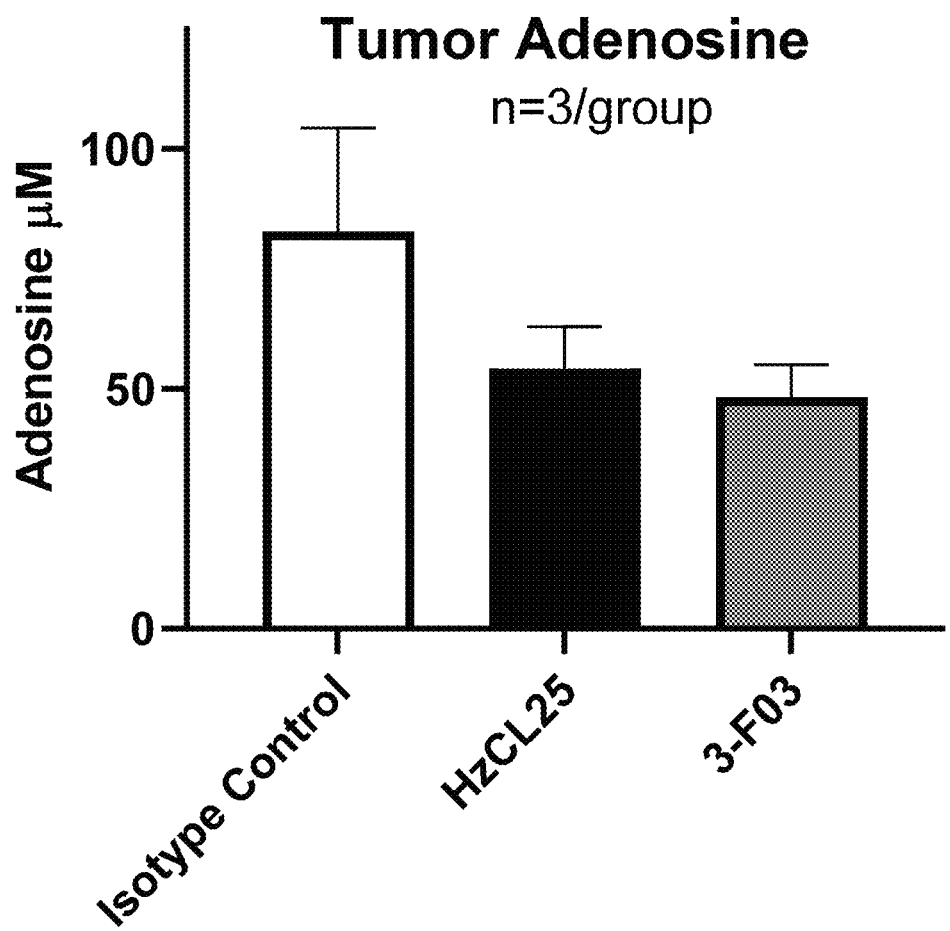
FIG. 26 is a graph depicting the concentration of adenosine in tumors treated with isotype control antibody, HzCL25, or 3-F03.

As demonstrated in FIG. 26, treatment with HzCL25 or 3-F03 resulted in a 35% and 42% decrease in intratumoral adenosine concentrations, respectively.

Example 24: CD73 Enzyme Inhibition by Anti-CD73 Antibodies

The molecular mechanism of inhibition of 3-F03 and HzCL25 was investigated using an enzymatic assay where recombinant full length CD73 was used and the production of adenosine was measured by LCMS. The data was analyzed using a mixed-inhibition model and the findings for both 3-F03 and HzCL25 are summarized in Table 9.

Briefly, the inhibition potencies of the agents were measured in an enzyme assay using adenosine $^{13}C_{10}$, $^{15}N_5$, 5'-monophoshpate sodium salt solution (650676, Sigma) as substrate and detecting product, adenosine by LC-MS. Antibody agents were serially diluted in buffer and a volume of 5 μL was transferred to a 96-well plate. 20 μL of 0.5 pM recombinant CD73 in assay buffer (25 mM Tris, 5 mM $MgCl_2$, 0.005% Brij35 pH 7.5) was added to the plate and pre-incubated for 2 hours at 25° C. The assay was initiated by the addition of a 25 μL solution containing AMP at various concentrations. The reactions were run for 0.5 hr at 25° C. and then quenched with 50 μL of methanol.

Figure 27:
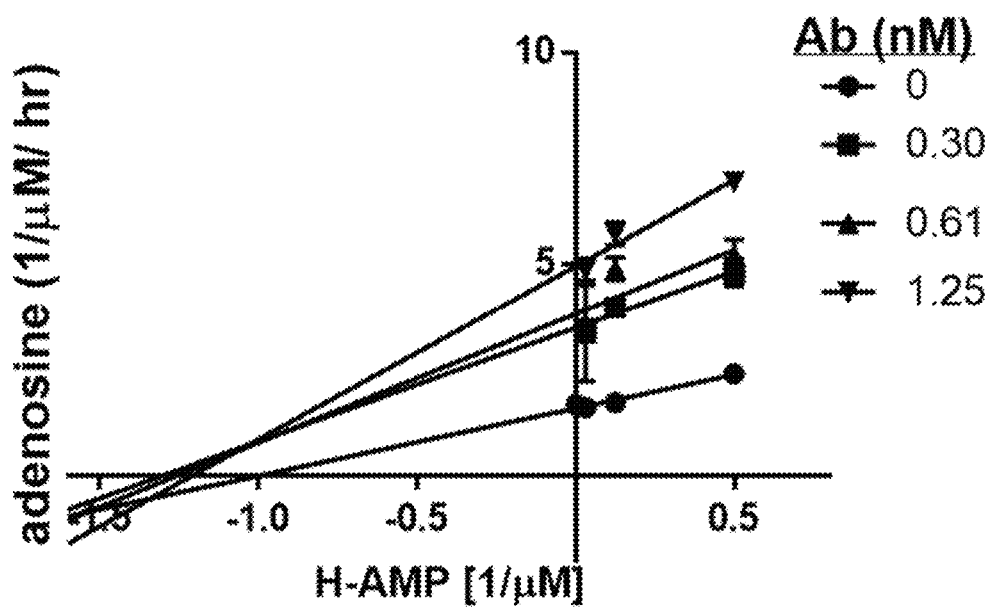
FIG. 27 is a graph depicting inhibition of adenosine at the indicated concentrations of HzCL25 antibody (Ab) and AMP.
Figure 28:
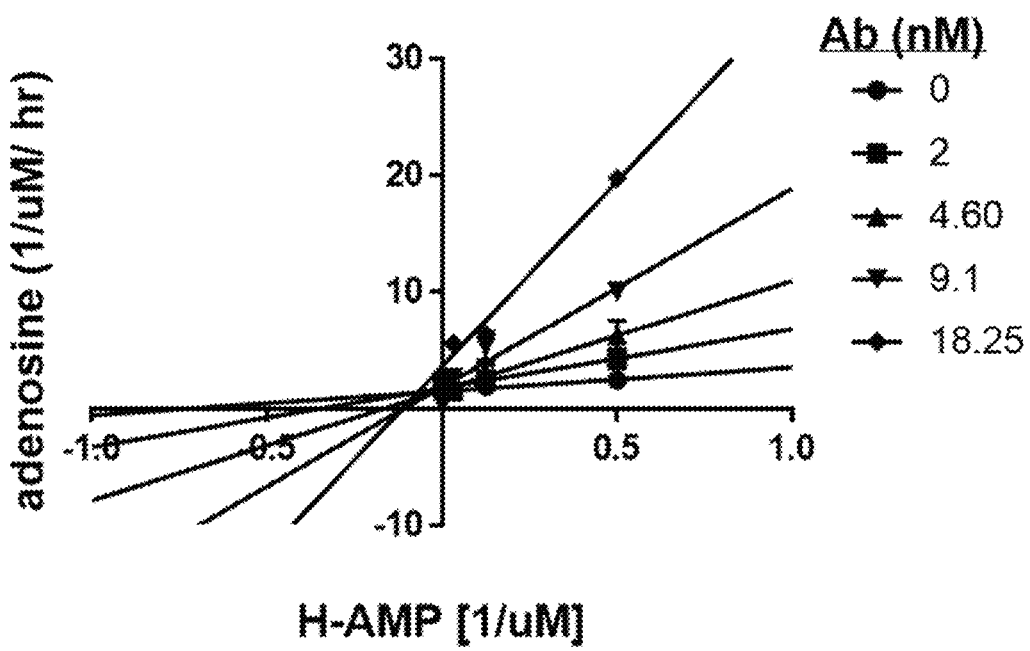
FIG. 28 is a graph depicting inhibition of adenosine at the indicated concentrations of 3-F03 antibody (Ab) and AMP.

The results indicated that HzCL25 is a non-competitive inhibitor, with Ki value of 0.3±0.2 nM, and α value close to unity (FIG. 27). 3-F03 is a mixed-inhibitor with Ki of 1.5±0.7 nM and a of 19±12 indicating that 3-F03 has a higher affinity towards free enzyme than enzyme substrate, and exhibits a competitiveness nature (FIG. 28).

Figure 29:
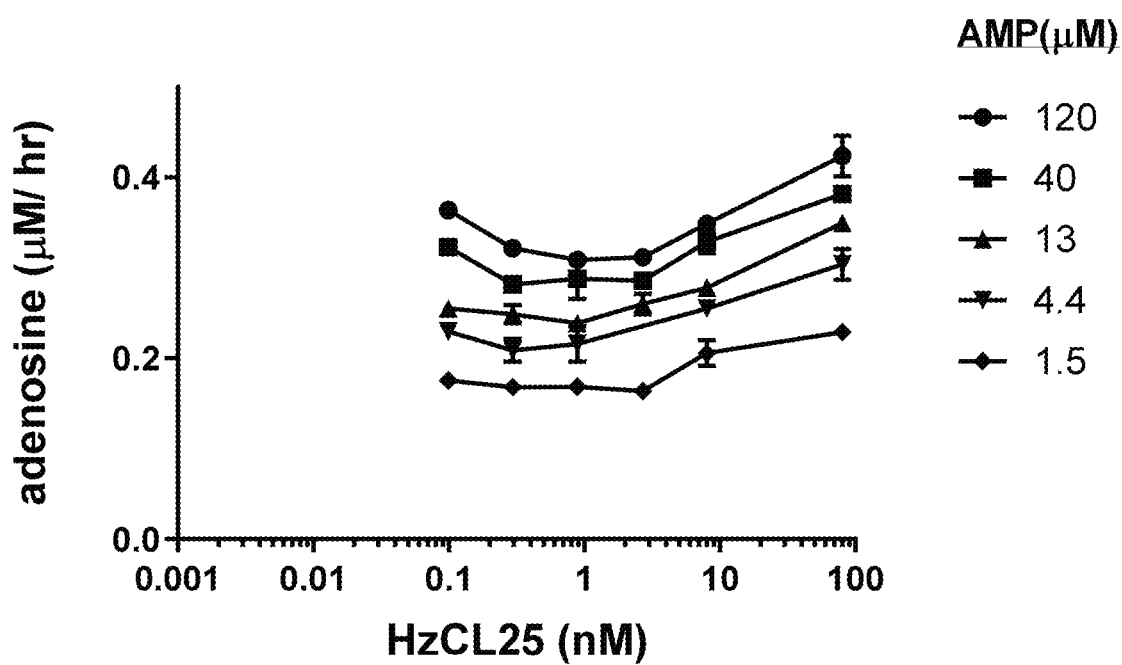
FIG. 29 is a graph depicting inhibition of adenosine at the indicated concentrations of HzCL25 antibody (Ab) and AMP.

In addition, HzCL25 exhibited a "hook" effect, where a loss of inhibition was observed at high agent concentrations (FIG. 29). This is an indication that the stoichiometry of HzCL25 and CD73 molecular interactions changes as their concentration ratio changes, which shifts the molecule population from the inhibited species to non-inhibited species.

TABLE 9

Summary of kinetic parameters for HzCL25 and 3-F03.

| Agent | Mechanism of Action | $K_i$ (nM) | α | $K_m$ (uM) |
|---|---|---|---|---|
| 3-F03 IgG | mixed inhibition | 1.5 ± 0.7 | 19 ± 12 | 1.4 ± 0.5 |
| HzCL25 IgG | non-competitive inhibition | 0.3 ± 0.2 | 2.1 ± 1.7 | 0.9 ± 0.3 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody that binds to human CD73, wherein the antibody comprises a variable heavy (VH) domain comprising a VH complementarity determining region (CDR)1, a VH CDR2, and a VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
wherein the antibody comprises a variable light (VL) domain comprising a VL CDR1, a VL CDR2, and a VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6).

2. The antibody of claim 1, wherein the VH domain comprises the amino acid sequence set forth in SEQ ID NO:22.

3. The antibody of claim 1, wherein the antibody comprises a heavy chain and wherein the heavy chain comprises the amino acid sequence set forth in SEQ ID NO:24.

4. The antibody of claim 1, wherein the VL domain comprises the amino acid sequence set forth in SEQ ID NO:23.

5. The antibody of claim 1, wherein the antibody comprises a light chain and wherein the light chain comprises the amino acid sequence set forth in SEQ ID NO:25.

6. The antibody of claim 1, wherein the VH domain is at least 80% identical to the amino acid sequence set forth in SEQ ID NO:22 and the VL domain is at least 80% identical to the amino acid sequence set forth in SEQ ID NO:23.

7. An antibody that binds to human CD73, wherein the antibody comprises a variable heavy (VH) domain and a variable light (VL) domain, wherein the VH domain comprises the amino acid sequence set forth in SEQ ID NO:22 and the VL domain comprises the amino acid sequence set forth in SEQ ID NO:23.

8. An antibody that binds to human CD73, wherein the antibody comprises a heavy chain and a light chain, and wherein the heavy chain comprises the amino acid sequence set forth in SEQ ID NO:24 and the light chain comprises the amino acid sequence set forth in SEQ ID NO:25.

9. The antibody of claim 1, which is a humanized antibody.

10. The antibody of claim 1, wherein the antibody is a bispecific antibody, a single chain antibody, an Fab fragment, an F(ab')₂ fragment, an Fab' fragment, an Fsc fragment, an Fv fragment, an scFv, an sc(Fv)₂, or a diabody.

11. A pharmaceutical composition comprising the antibody of claim 1 and a pharmaceutically acceptable carrier.

12. The antibody of claim 1, which is an IgG antibody.

13. The antibody of claim 1, which is an IgG1 antibody.

14. The antibody of claim 1, which is an IgG1/kappa antibody.

15. The antibody of claim 1, wherein the antibody is aglycosylated.

16. The antibody of claim 1, wherein the antibody comprises a heavy chain and a light chain, wherein the heavy chain comprises a heavy chain constant region, and wherein the heavy chain constant region includes an alanine at position asparagine-297, according to EU numbering.

17. The antibody of claim 1, wherein the antibody comprises a heavy chain and a light chain, and wherein the heavy chain is at least 80% identical to the amino acid sequence set forth in SEQ ID NO:24 and the light chain is at least 80% identical to the amino acid sequence set forth in SEQ ID NO: 25.

18. The antibody of claim 7, which is an IgG antibody.

19. The antibody of claim 7, which is an IgG1 antibody.

20. The antibody of claim 7, which is an IgG1/kappa antibody.

21. The antibody of claim 7, wherein the antibody is aglycosylated.

22. The antibody of claim 7, wherein the antibody comprises a heavy chain and a light chain, wherein the heavy chain comprises a heavy chain constant region, wherein the heavy chain constant region includes an alanine at position asparagine-297, according to EU numbering.

23. The antibody of claim 7, wherein the antibody is a bispecific antibody, a single chain antibody, an Fab fragment, an F(ab')₂ fragment, an Fab' fragment, an Fsc fragment, an FIT fragment, an scFv, an sc(Fv)₂, or a diabody.

24. A pharmaceutical composition comprising the antibody of claim 7 and a pharmaceutically acceptable carrier.

25. A pharmaceutical composition comprising the antibody of claim 8 and a pharmaceutically acceptable carrier.

26. A pharmaceutical composition comprising the antibody of claim 14 and a pharmaceutically acceptable carrier.

27. A pharmaceutical composition comprising the antibody of claim 20 and a pharmaceutically acceptable carrier.

* * * * *

SEQUENCE LISTING

```
<160> NUMBER OF SEQ ID NOS: 93

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Thr Phe Thr Ser Tyr Gly
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2
```

```
Ile Tyr Pro Gly Ser Gly Asn Thr
1               5

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Arg Tyr Asp Tyr Leu Gly Ser Ser Tyr Gly Phe Asp Tyr
1               5                   10

<210> SEQ ID NO 4
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gln Asp Val Ser Thr Ala
1               5

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Ala Ser
1

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln His Tyr Asn Thr Pro Tyr Thr
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Tyr Thr Phe Thr Ser Tyr
1               5
```

```
<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Tyr Pro Gly Ser Gly Asn
1               5

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Tyr Asp Tyr Leu Gly Ser Ser Tyr Gly Phe Asp Tyr
1               5                   10

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Ala Ser Gln Asp Val Ser Thr Ala Val Ala
1               5                   10

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Ala Ser Tyr Arg Tyr Ser
1               5

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Tyr Thr Phe Thr Ser Tyr Gly Leu Ser
1               5                   10

<210> SEQ ID NO 13
<211> LENGTH: 10
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic peptide"

<400> SEQUENCE: 13

Glu Ile Tyr Pro Gly Ser Gly Asn Thr Tyr
1               5                   10

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Gly Leu Ser
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Glu Ile Tyr Pro Gly Ser Gly Asn Thr Tyr Tyr Asn Glu Lys Phe Lys
1               5                   10                  15

Gly

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Thr Ser Tyr Gly Leu Ser
1               5

<210> SEQ ID NO 17
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Trp Met Gly Glu Ile Tyr Pro Gly Ser Gly Asn Thr Tyr
1               5                   10

<210> SEQ ID NO 18
<211> LENGTH: 13
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 18

Ala Arg Tyr Asp Tyr Leu Gly Ser Ser Tyr Gly Phe Asp
1               5                   10

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Thr Ala Val Ala Trp Tyr
1               5

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Leu Leu Ile Tyr Ser Ala Ser Tyr Arg Tyr
1               5                   10

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gln His Tyr Asn Thr Pro Tyr
1               5

<210> SEQ ID NO 22
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
                20                  25                  30

Gly Leu Ser Trp Val Arg Gln Met Pro Gly Lys Gly Leu Glu Trp Met
            35                  40                  45

Gly Glu Ile Tyr Pro Gly Ser Gly Asn Thr Tyr Tyr Asn Glu Lys Phe
        50                  55                  60

Lys Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120
```

<210> SEQ ID NO 23
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Tyr Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Asn Thr Pro Tyr
                85                  90                  95

Thr Phe Gly Gly Gly Thr Lys Leu Glu Ile Lys
            100                 105
```

<210> SEQ ID NO 24
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Gly Leu Ser Trp Val Arg Gln Met Pro Gly Lys Gly Leu Glu Trp Met
        35                  40                  45

Gly Glu Ile Tyr Pro Gly Ser Gly Asn Thr Tyr Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
```

```
                20                  25                  30
Val Ala Trp Tyr Gln Gln Lys Pro Gly Gln Pro Pro Lys Leu Leu Ile
            35                  40                  45

Tyr Ser Ala Ser Tyr Arg Tyr Ser Gly Val Pro Asp Arg Phe Ser Gly
     50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln His Tyr Asn Thr Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Val Gln Leu Gln Gln Ser Gly Ala Glu Leu Ala Arg Pro Gly Ala
1               5                   10                  15

Ser Val Lys Leu Ser Cys Arg Ala Ser Gly Tyr Thr Phe Thr Ser Tyr
            20                  25                  30

Gly Leu Ser Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Tyr Asp Tyr Leu Gly Ser Ser Tyr Gly Phe Asp Tyr Trp Gly
            100                 105                 110

Gln Gly Thr Thr Leu Thr Val Ser Ser
        115                 120

<210> SEQ ID NO 27
<211> LENGTH: 107
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 27

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Asn Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asn Thr Pro Tyr
                85                  90                  95

Thr Phe Gly Gly Gly Thr Lys Leu Glu Ile Lys
            100                 105

<210> SEQ ID NO 28
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Trp Ile Gly Glu Ile Tyr Pro Gly Ser Gly Asn Thr Tyr
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Ala Ser Tyr Arg Tyr Asn
1               5

<210> SEQ ID NO 30
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45
```

```
Ala Val Met Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ile Ala Ala Lys Gly Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Ala Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 31
<211> LENGTH: 212
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31
```

| | | | | | | | | | | | | | | | |
|---|---|---|---|---|---|---|---|---|---|---|---|---|---|---|---|
| Ile | Gln | Met | Thr | Gln | Ser | Pro | Ser | Ser | Leu | Ser | Ala | Ser | Val | Gly | Asp |
| 1 | | | | 5 | | | | | 10 | | | | | 15 | |
| Arg | Val | Thr | Ile | Thr | Cys | Arg | Ala | Ser | Gln | Gly | Ile | Ser | Asn | Tyr | Leu |
| | | | 20 | | | | | 25 | | | | | 30 | | |
| Ala | Trp | Tyr | Gln | Gln | Lys | Pro | Gly | Lys | Ala | Pro | Lys | Leu | Leu | Ile | Tyr |
| | | | 35 | | | | | 40 | | | | | 45 | | |
| Ala | Ala | Ser | Thr | Leu | Gln | Ser | Gly | Val | Pro | Ser | Arg | Phe | Ser | Gly | Ser |
| | 50 | | | | | 55 | | | | | 60 | | | | |
| Gly | Ser | Gly | Thr | Asp | Phe | Thr | Leu | Thr | Ile | Ser | Ser | Leu | Gln | Pro | Glu |
| 65 | | | | 70 | | | | | 75 | | | | | 80 | |
| Asp | Phe | Ala | Thr | Tyr | Tyr | Cys | Gln | Gln | Ser | Tyr | Ser | Thr | Pro | His | Phe |
| | | | | 85 | | | | | 90 | | | | | 95 | |
| Gly | Gln | Gly | Thr | Arg | Leu | Glu | Ile | Lys | Arg | Thr | Val | Ala | Ala | Pro | Ser |
| | | | 100 | | | | | 105 | | | | | 110 | | |
| Val | Phe | Ile | Phe | Pro | Pro | Ser | Asp | Glu | Gln | Leu | Lys | Ser | Gly | Thr | Ala |
| | | | 115 | | | | | 120 | | | | | 125 | | |
| Ser | Val | Val | Cys | Leu | Leu | Asn | Asn | Phe | Tyr | Pro | Arg | Glu | Ala | Lys | Val |
| | 130 | | | | | 135 | | | | | 140 | | | | |
| Gln | Trp | Lys | Val | Asp | Asn | Ala | Leu | Gln | Ser | Gly | Asn | Ser | Gln | Glu | Ser |
| 145 | | | | 150 | | | | | 155 | | | | | 160 | |
| Val | Thr | Glu | Gln | Asp | Ser | Lys | Asp | Ser | Thr | Tyr | Ser | Leu | Ser | Ser | Thr |
| | | | | 165 | | | | | 170 | | | | | 175 | |
| Leu | Thr | Leu | Ser | Lys | Ala | Asp | Tyr | Glu | Lys | His | Lys | Val | Tyr | Ala | Cys |
| | | | 180 | | | | | 185 | | | | | 190 | | |
| Glu | Val | Thr | His | Gln | Gly | Leu | Ser | Ser | Pro | Val | Thr | Lys | Ser | Phe | Asn |
| | | | 195 | | | | | 200 | | | | | 205 | | |
| Arg | Gly | Glu | Cys | | | | | | | | | | | | |
| | 210 | | | | | | | | | | | | | | |

```
<210> SEQ ID NO 32
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32
```

| | | | | | | | | | | | | | | | |
|---|---|---|---|---|---|---|---|---|---|---|---|---|---|---|---|
| Val | Gln | Leu | Val | Glu | Ser | Gly | Gly | Gly | Leu | Val | Gln | Pro | Gly | Gly | Ser |
| 1 | | | | 5 | | | | | 10 | | | | | 15 | |
| Leu | Arg | Leu | Ser | Cys | Ala | Ala | Ser | Gly | Phe | Thr | Phe | Ser | Ser | Tyr | Asp |
| | | | 20 | | | | | 25 | | | | | 30 | | |
| Met | His | Trp | Val | Arg | Gln | Ala | Pro | Gly | Lys | Gly | Leu | Glu | Trp | Val | Ala |
| | | | 35 | | | | | 40 | | | | | 45 | | |
| Val | Met | Ser | Tyr | Ser | Gly | Ser | Asn | Lys | Tyr | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ser | Lys | Asn | Thr | Leu | Tyr | Leu |
| 65 | | | | 70 | | | | | 75 | | | | | 80 | |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |

Thr Glu Ile Ala Ala Lys Gly Asp Tyr Trp Gly Gln Gly Thr Leu Val
            100                 105                 110

Thr Val Ser Ser
        115

<210> SEQ ID NO 33
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
    435                 440                 445

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Phe Thr Phe Ser Ser Tyr Asp
1               5

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Met Ser Tyr Asp Gly Ser Asn Lys
1               5

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Thr Glu Ile Ala Ala Lys Gly Asp Tyr
1               5                   10

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 37

Gln Gly Ile Ser Asn Tyr
1               5

<210> SEQ ID NO 38
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ala Ser
1

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gln Gln Ser Tyr Ser Thr Pro His
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Ser Tyr Glu Gly Ser Asn Lys
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Phe Thr Phe Ser Ser Tyr
1               5

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Tyr Asp Gly Ser Asn
1               5
```

```
<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Tyr Glu Gly Ser Asn
1               5

<210> SEQ ID NO 44
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Arg Ala Ser Gln Gly Ile Ser Asn Tyr Leu Ala
1               5                   10

<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Ala Ser Thr Leu Gln Ser
1               5

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Phe Thr Phe Ser Ser Tyr Asp Met His
1               5                   10

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Val Met Ser Tyr Asp Gly Ser Asn Lys Tyr
1               5                   10

<210> SEQ ID NO 48
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Val Met Ser Tyr Glu Gly Ser Asn Lys Tyr
1               5                   10

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ser Tyr Asp Met His
1               5

<210> SEQ ID NO 50
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Val Met Ser Tyr Asp Gly Ser Asn Lys Tyr Tyr Ala Asp Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Val Met Ser Tyr Glu Gly Ser Asn Lys Tyr Tyr Ala Asp Ser Val Lys
1               5                   10                  15

Gly

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Ile Ala Ala Lys Gly Asp Tyr
1               5

<210> SEQ ID NO 53
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Ser Tyr Asp Met His
1               5

<210> SEQ ID NO 54
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Trp Val Ala Val Met Ser Tyr Asp Gly Ser Asn Lys Tyr
1               5                   10

<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Trp Val Ala Val Met Ser Tyr Glu Gly Ser Asn Lys Tyr
1               5                   10

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ala Thr Glu Ile Ala Ala Lys Gly Asp
1               5

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Asn Tyr Leu Ala Trp Tyr
1               5

<210> SEQ ID NO 58
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 58

Leu Leu Ile Tyr Ala Ala Ser Thr Leu Gln
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Gln Ser Tyr Ser Thr Pro
1               5

<210> SEQ ID NO 60
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 61
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Ser Asn Tyr Leu
            20                  25                  30

Ala Trp Tyr Gln Gln Lys Pro Gly Lys Ala Pro Lys Leu Leu Ile Tyr
        35                  40                  45
```

Ala Ala Ser Thr Leu Gln Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro His Phe
                85                  90                  95

Gly Gln Gly Thr Arg Leu Glu Ile Lys
            100                 105

<210> SEQ ID NO 62
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Asp Gly Ser Asn Lys Tyr Tyr Ala Asp Ser Val
    50                  55                  60

Lys Gly Arg Phe Thr Ile Ser Arg Asp Asn Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser
        115

<210> SEQ ID NO 63
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

```
Ala Thr Glu Ile Ala Ala Lys Gly Asp Tyr Trp Gly Gln Gly Thr Leu
                100                 105                 110

Val Thr Val Ser Ser
        115

<210> SEQ ID NO 64
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro His
                85                  90                  95

Phe Gly Gln Gly Thr Arg Leu Glu Ile Lys
            100                 105

<210> SEQ ID NO 65
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro His
                85                  90                  95

Phe Gly Gln Gly Thr Arg Leu Glu Ile Lys
            100                 105

<210> SEQ ID NO 66
<211> LENGTH: 446
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 66

```
Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Val Arg Gln Ala Pro Gly Lys Gly Leu Glu Trp Val Ala
        35                  40                  45

Val Met Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 67
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Ser Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 68
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110
```

-continued

```
Val Thr Val Ser Ser
            115

<210> SEQ ID NO 69
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Ser Gly Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser
            115

<210> SEQ ID NO 70
<211> LENGTH: 523
<212> TYPE: PRT
<213> ORGANISM: Homo sapiens

<400> SEQUENCE: 70

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175
```

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
            195                 200                 205

Gly Val Asp Val Val Gly Gly His Ser Asn Thr Phe Leu Tyr Thr
            210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Gln Ala Tyr Ala
            245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
            290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
            325                 330                 335

Leu Ile Cys Asp Ala Met Ile Asn Asn Asn Leu Arg His Thr Asp Glu
            340                 345                 350

Met Phe Trp Asn His Val Ser Met Cys Ile Leu Asn Gly Gly Ile
            355                 360                 365

Arg Ser Pro Ile Asp Glu Arg Asn Asn Gly Thr Ile Thr Trp Glu Asn
            370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
            405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
            485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Phe Ser
            515                 520

<210> SEQ ID NO 71
<211> LENGTH: 523
<212> TYPE: PRT
<213> ORGANISM: Mus musculus

<400> SEQUENCE: 71

Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val

```
            20                  25                  30
Gly Gly Val Ala Arg Leu Phe Thr Lys Val Gln Gln Ile Arg Lys Glu
            35                  40                  45
Glu Pro Asn Val Leu Phe Leu Asp Ala Gly Asp Gln Tyr Gln Gly Thr
50                  55                  60
Ile Trp Phe Thr Val Tyr Lys Gly Leu Glu Val Ala His Phe Met Asn
65                  70                  75                  80
Ile Leu Gly Tyr Asp Ala Met Ala Leu Gly Asn His Glu Phe Asp Asn
                85                  90                  95
Gly Val Glu Gly Leu Ile Asp Pro Leu Leu Arg Asn Val Lys Phe Pro
            100                 105                 110
Ile Leu Ser Ala Asn Ile Lys Ala Arg Gly Pro Leu Ala His Gln Ile
            115                 120                 125
Ser Gly Leu Phe Leu Pro Ser Lys Val Leu Ser Val Gly Gly Glu Val
            130                 135                 140
Val Gly Ile Val Gly Tyr Thr Ser Lys Glu Thr Pro Phe Leu Ser Asn
145                 150                 155                 160
Pro Gly Thr Asn Leu Val Phe Glu Asp Glu Ile Ser Ala Leu Gln Pro
                165                 170                 175
Glu Val Asp Lys Leu Lys Thr Leu Asn Val Asn Lys Ile Ile Ala Leu
            180                 185                 190
Gly His Ser Gly Phe Glu Met Asp Lys Leu Ile Ala Gln Lys Val Arg
            195                 200                 205
Gly Val Asp Ile Val Val Gly Gly His Ser Asn Thr Phe Leu Tyr Thr
            210                 215                 220
Gly Asn Pro Pro Ser Lys Glu Val Pro Ala Gly Lys Tyr Pro Phe Ile
225                 230                 235                 240
Val Thr Ala Asp Asp Gly Arg Gln Val Pro Val Val Gln Ala Tyr Ala
                245                 250                 255
Phe Gly Lys Tyr Leu Gly Tyr Leu Lys Val Glu Phe Asp Asp Lys Gly
            260                 265                 270
Asn Val Ile Thr Ser Tyr Gly Asn Pro Ile Leu Leu Asn Ser Ser Ile
            275                 280                 285
Pro Glu Asp Ala Thr Ile Lys Ala Asp Ile Asn Gln Trp Arg Ile Lys
            290                 295                 300
Leu Asp Asn Tyr Ser Thr Gln Glu Leu Gly Arg Thr Ile Val Tyr Leu
305                 310                 315                 320
Asp Gly Ser Thr Gln Thr Cys Arg Phe Arg Glu Cys Asn Met Gly Asn
                325                 330                 335
Leu Ile Cys Asp Ala Met Ile Asn Asn Asn Leu Arg His Pro Asp Glu
            340                 345                 350
Met Phe Trp Asn His Val Ser Met Cys Ile Val Asn Gly Gly Gly Ile
            355                 360                 365
Arg Ser Pro Ile Asp Glu Lys Asn Asn Gly Thr Ile Thr Trp Glu Asn
            370                 375                 380
Leu Ala Ala Val Leu Pro Phe Gly Gly Thr Phe Asp Leu Val Gln Leu
385                 390                 395                 400
Lys Gly Ser Thr Leu Lys Lys Ala Phe Glu His Ser Val His Arg Tyr
                405                 410                 415
Gly Gln Ser Thr Gly Glu Phe Leu Gln Val Gly Gly Ile His Val Val
            420                 425                 430
Tyr Asp Ile Asn Arg Lys Pro Trp Asn Arg Val Val Gln Leu Glu Val
            435                 440                 445
```

```
Leu Cys Thr Lys Cys Arg Val Pro Ile Tyr Glu Pro Leu Glu Met Asp
        450                 455                 460

Lys Val Tyr Lys Val Thr Leu Pro Ser Tyr Leu Ala Asn Gly Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Glu Tyr Ile Ser Lys Met Lys Val Val
                500                 505                 510

Tyr Pro Ala Val Glu Gly Arg Ile Lys Phe Ser
                515                 520

<210> SEQ ID NO 72
<211> LENGTH: 523
<212> TYPE: PRT
<213> ORGANISM: Macaca fascicularis

<400> SEQUENCE: 72

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
                20                  25                  30

Gly Gly Val Ala Arg Leu Phe Thr Lys Val Gln Gln Ile Arg Arg Ala
            35                  40                  45

Glu Pro Asn Val Leu Leu Leu Asp Ala Gly Asp Gln Tyr Gln Gly Thr
        50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Thr Asp Lys Leu Ile Ala Gln Lys Val Arg
        195                 200                 205

Gly Val Asp Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
```

```
                        290                 295                 300
Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Ile Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Phe Ser
        515                 520

<210> SEQ ID NO 73
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 74
<211> LENGTH: 107
<212> TYPE: PRT
<213> ORGANISM: Homo sapiens

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 75
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 14
<212> TYPE: PRT
<213> ORGANISM: Homo sapiens

<400> SEQUENCE: 76

Thr Lys Val Gln Gln Ile Arg Arg Ala Glu Pro Asn Val Leu
1               5                   10

<210> SEQ ID NO 77
<211> LENGTH: 117

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser
        115

<210> SEQ ID NO 78
<211> LENGTH: 14
<212> TYPE: PRT
<213> ORGANISM: Homo sapiens

<400> SEQUENCE: 78

Ala Ala Val Leu Pro Phe Gly Gly Thr Phe Asp Leu Val Gln
1               5                   10

<210> SEQ ID NO 79
<211> LENGTH: 20
<212> TYPE: PRT
<213> ORGANISM: Homo sapiens

<400> SEQUENCE: 79

Ile Leu Pro Asn Phe Leu Ala Asn Gly Gly Asp Gly Phe Gln Met Ile
1               5                   10                  15

Lys Asp Glu Leu
            20

<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Leu
        35                  40                  45
```

```
Tyr Ser Ala Ser Tyr Arg Tyr Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Asn Thr Pro Tyr
                85                  90                  95

Thr Phe Gly Gly Gly Thr Lys Leu Glu Ile Lys
                100                 105

<210> SEQ ID NO 81
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Ile Arg Met Thr Gln Ser Pro Ser Ser Phe Ser Ala Ser Thr Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln His Tyr Asn Thr Pro Tyr
                85                  90                  95

Thr Phe Gly Gly Gly Thr Lys Leu Glu Ile Lys
                100                 105

<210> SEQ ID NO 82
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Leu Ser Trp Val Arg Gln Ala Thr Gly Gln Gly Leu Glu Trp Met
            35                  40                  45

Gly Glu Ile Tyr Pro Gly Ser Gly Asn Thr Tyr Tyr Asn Glu Lys Phe
        50                  55                  60

Lys Gly Arg Val Thr Met Thr Ala Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
                100                 105                 110

Ala Gly Thr Thr Val Thr Val Ser Ser
```

115                 120

<210> SEQ ID NO 83
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Leu Ser Trp Val Arg Gln Ala Thr Gly Gln Gly Leu Glu Trp Met
            35                  40                  45

Gly Glu Ile Tyr Pro Gly Ser Gly Asn Thr Tyr Tyr Asn Glu Lys Phe
        50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 84
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Gly Leu Ser Trp Val Arg Gln Ala Pro Gly Gln Gly Leu Glu Trp Met
            35                  40                  45

Gly Glu Ile Tyr Pro Gly Ser Gly Asn Thr Tyr Tyr Asn Glu Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 85
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 85

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 86
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser
        115

<210> SEQ ID NO 87
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 87

```
Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Glu Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115
```

<210> SEQ ID NO 88
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Glu Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115
```

<210> SEQ ID NO 89
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89

```
gaagtgcagc tcgtgcagtc cggagccgaa gtgaaaaagc tggagagtc cctgaagatc    60 agctgcaagg gttccggcta cattcacc tcctacgggc tcagctgggt cagacagatg    120
ccgggaaagg gtcttgagtg gatgggagag atctacccgg ctccggcaa cacctactac    180 aacgaaaagt tcaagggcca ggtcaccatt tccgccgaca gtcaatctc caccgcttac    240
```

```
ctccaatggt cgagcctgaa ggcatcggat accgcgatgt actactgcgc ccgctacgac    300
tacctgggct cgtcatacgg cttcgattac tgggggcgg gaactaccgt gactgtgtcc    360
tccgcctcca ctaagggacc ctcagtgttc ccccttgccc cgagctccaa gagcacttcg    420
ggcggaaccg ctgccctggg ttgcctcgtg aaggattact tccccgagcc tgtgaccgtg    480
tcctggaact ccggggcctt gaccagcgga gtccacacct cccggccgt gctgcaatca    540 tccggtctgt acagtctgtc ctccgtggtc acggtgccct cgtcctcact ggggactcag    600
acttacatct gtaacgtgaa ccataagcca tcgaacacca aagtcgacaa acgggtggaa    660
cctaagtcat gcgacaagac ccacacgtgc ccaccttgcc ccgcccccga gctcctgggg    720
gggccgagcg tgttcctctt cccgccgaaa ccgaaggaca ccctgatgat ctcgaggact    780
cctgaagtca cttgcgtggt cgtggacgtg tcgcacgagg accccgaagt caagttcaat    840
tggtacgtgg acggagtcga agtgcacaac gctaagacca accccgcga ggagcagtac    900 gcaagcacct accgcgttgt cagcgtgctc accgtgctgc atcaggattg gctgaatgga    960
aaggagtaca agtgcaaagt gtccaacaag gccctgcctg caccaattga aaagaccatc   1020
tccaaggcca agggccagcc ccgggagccc caagtctaca ctctgccgcc gtcgagagaa   1080
gaaatgacca agaaccaagt gtccctgact tgtctggtca agggcttcta tccttcggac   1140
atcgcggtgg aatgggagag caacggccag ccggagaaca attacaagac tacgccaccc   1200
gtgctggact ctgacggctc cttttttcctg tattccaagc tcaccgtgga caagagccgc   1260
tggcaacagg gaaacgtgtt cagctgctcc gtgatgcacg aagccctgca caaccactac   1320
acccagaagt ccctgagctt gtcccctggt                                     1350

<210> SEQ ID NO 90
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
gacatcgtga tgacccagtc cccggattca ctcgcggtgt ctttggggga gagggcaacc     60
attaactgca aggcctcaca ggatgtgtcc actgctgtcg cctggtacca gcagaagcct    120
gggcagccgc ccaagctgct gatctactcg gcctcctacc gctattccgg agtccccgac    180
cggttctccg gctcgggttc cggaactgat ttcaccctga caatttcgtc gctgcaagcc    240
gaggacgtgg ccgtgtacta ctgccaacag cattacaaca ctccttacac ttttggtggc    300
ggaactaagc tcgagatcaa gcggacggtg gcagctccgt cagtgttcat cttccctcca    360
tcggacgaac agctgaagtc cggcaccgcg tccgtcgtgt gtctgttgaa caacttctac    420
ccgcgggaag ccaaggtcca gtggaaagtc gacaacgcgc tgcagtccgg aaatagccag    480
gaaagcgtga ccgaacagga ctccaaggac agcacctact ccctgagctc aaccctgacc    540
ctgagcaagg ccgactatga gaagcacaaa gtgtacgcct gcgaagtgac ccaccaaggc    600
ctgagcagcc cagtgaccaa gtccttcaac cgcggggagt gt                      642

<210> SEQ ID NO 91
<211> LENGTH: 1338
<212> TYPE: DNA
<213> ORGANISM: Artificial Sequence
<220> FEATURE:
```

<220> FEATURE:
<221> NAME/KEY: source
<223> OTHER INFORMATION: /note="Description of Artificial Sequence:
      Synthetic polynucleotide"

<400> SEQUENCE: 91

| | | | | | | |
|---|---|---|---|---|---|---|
| gaagtgcagt | tggtggagag | cggggggcgga | ctggtgcagc | cgggggggctc | gctgcggctg | 60 |
| tcctgcgccg | cgtccggttt | cacttttcg | agctacgaca | tgcactgggt | ccgccaagca | 120 |
| ccggggaagg | gtctggaatg | ggtggccgtg | atgtcgtacg | acggctccaa | caagtactac | 180 |
| gccgactccg | tgaagggacg | gttcaccatc | tcccgcgaca | acagcaagaa | cgcccttac | 240 |
| ctccaaatga | acagcctgag | ggccgaggac | acagccgtat | actactgcgc | gaccgagatc | 300 |
| gccgccaagg | gggactactg | gggtcaaggc | actctggtca | ccgtgtcctc | cgcctccact | 360 |
| aagggaccct | cagtgttccc | ccttgccccg | agctccaaga | gcacttcggg | cggaaccgct | 420 |
| gccctgggtt | gcctcgtgaa | ggattacttc | cccgagcctg | tgaccgtgtc | ctggaactcc | 480 |
| ggggccttga | ccagcggagt | ccacaccttc | ccggccgtgc | tgcaatcatc | cggtctgtac | 540 |
| agtctgtcct | ccgtggtcac | ggtgccctcg | tcctcactgg | ggactcagac | ttacatctgt | 600 |
| aacgtgaacc | ataagccatc | gaacaccaaa | gtcgacaaac | gggtggaacc | taagtcatgc | 660 |
| gacaagaccc | acacgtgccc | accttgcccc | gcccccgagc | tcctgggggg | gccgagcgtg | 720 |
| ttcctcttcc | cgccgaaacc | gaaggacacc | ctgatgatct | cgaggactcc | tgaagtcact | 780 |
| tgcgtggtcg | tggacgtgtc | gcacgaggac | cccgaagtca | agttcaattg | gtacgtggac | 840 |
| ggagtcgaag | tgcacaacgc | taagaccaaa | ccccgcgagg | agcagtacgc | aagcacctac | 900 |
| cgcgttgtca | gcgtgctcac | cgtgctgcat | caggattggc | tgaatggaaa | ggagtacaag | 960 |
| tgcaaagtgt | ccaacaaggc | cctgcctgca | ccaattgaaa | agaccatctc | caaggccaag | 1020 |
| ggccagcccc | gggagcccca | agtctacact | ctgccgccgt | cgagagaaga | aatgaccaag | 1080 |
| aaccaagtgt | ccctgacttg | tctggtcaag | ggcttctatc | cttcggacat | cgcggtggaa | 1140 |
| tgggagagca | acggccagcc | ggagaacaat | tacaagacta | cgccacccgt | gctggactct | 1200 |
| gacggctcct | tttcctgta | ttccaagctc | accgtggaca | agagccgctg | caacaggga | 1260 |
| aacgtgttca | gctgctccgt | gatgcacgaa | gccctgcaca | accactacac | ccagaagtcc | 1320 |
| ctgagcttgt | ccctggt | | | | | 1338 |

<210> SEQ ID NO 92
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

| | | | | | | |
|---|---|---|---|---|---|---|
| atccagatga | ctcagtcccc | ttcctcgttg | tccgcttccg | tgggtgatcg | ggtcacaatc | 60 |
| acttgccggg | ccagccaggg | aatttccaac | tacctcgcct | ggtaccagca | gaagcccgga | 120 |
| aaggcaccga | agctgctgat | ctacgccgcg | tccactctgc | aatccggagt | gccttctcgg | 180 |
| ttctcgggct | cgggaagcgg | caccgacttt | accctgacca | ttagcagcct | gcagcccgag | 240 |
| gacttcgcaa | cctactactg | tcagcagtcc | tactcaaccc | ctcacttcgg | acagggtact | 300 |
| agactcgaga | tcaagaggac | tgtggccgcg | ccgtcggtgt | tcatcttccc | accctcggac | 360 |
| gagcagctga | agtccggcac | cgccagcgtg | gtctgcctgc | tgaacaactt | ctatccgcgc | 420 |
| gaagccaagg | tccagtggaa | agtggataat | gcgctgcaga | gcgggaactc | ccaagagtcc | 480 |

```
gtgacggaac aggactccaa agactccacc tactcactgt catccaccct gaccctgtca    540
aaggccgact acgagaagca taaggtctac gcctgcgaag tgacccacca agggctgagc    600
tcgcccgtga ccaagtcctt caaccggggc gaatgc                             636
```

<210> SEQ ID NO 93
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gaagtgcagt tggtggagag cgggggcgga ctggtgcagc cggggggctc gctgcggctg     60
tcctgcgccg cgtccggttt cacttttcg agctacgaca tgcactgggt ccgccaagca    120
ccggggaagg gtctggaatg ggtggccgtg atgtcgtacg aaggctccaa caagtactac    180
gccgactccg tgaagggacg gttcaccatc tcccgcgaca cagcaagaa cgcccttttac    240 ctccaaatga acagcctgag ggccgaggac acagccgtat actactgcgc gaccgagatc    300
gccgccaagg gggactactg gggtcaaggc actctggtca ccgtgtcctc cgcctccact    360
aagggaccct cagtgttccc ccttgccccg agctccaaga gcacttcggg cggaaccgct    420
gccctgggtt gcctcgtgaa ggattacttc cccgagcctg tgaccgtgtc ctggaactcc    480
ggggccttga ccagcggagt ccacaccttc ccggccgtgc tgcaatcatc cggtctgtac    540
agtctgtcct ccgtggtcac ggtgccctcg tcctcactgg ggactcagac ttacatctgt    600
aacgtgaacc ataagccatc gaacaccaaa gtcgacaaac gggtggaacc taagtcatgc    660
gacaagaccc acacgtgccc accttgcccc gcccccgagc tcctgggggg gccgagcgtg    720
ttcctcttcc cgccgaaacc gaaggacacc ctgatgatct cgaggactcc tgaagtcact    780
tgcgtggtcg tggacgtgtc gcacgaggac cccgaagtca agttcaattg gtacgtggac    840
ggagtcgaag tgcacaacgc taagaccaaa ccccgcgagg agcagtacgc aagcacctac    900
cgcgttgtca gcgtgctcac cgtgctgcat caggattggc tgaatggaaa ggagtacaag    960
tgcaaagtgt ccaacaaggc cctgcctgca ccaattgaaa agaccatctc caaggccaag   1020
ggccagcccc gggagcccca agtctacact ctgccgccgt cgagagaaga aatgaccaag   1080
aaccaagtgt ccctgacttg tctggtcaag ggcttctatc cttcggacat cgcggtggaa   1140
tgggagagca acggccagcc ggagaacaat tacaagacta cgccacccgt gctggactct   1200
gacggctcct ttttcctgta ttccaagctc accgtggaca gagccgctg gcaacaggga   1260 aacgtgttca gctgctccgt gatgcacgaa gccctgcaca accactacac ccagaagtcc   1320
ctgagcttgt cccctggt                                                1338
```

UNITED STATES PATENT AND TRADEMARK OFFICE
CERTIFICATE OF CORRECTION

| | |
|---|---|
| PATENT NO. | : 12,018,089 B2 |
| APPLICATION NO. | : 17/138279 |
| DATED | : June 25, 2024 |
| INVENTOR(S) | : Horacio G. Nastri et al. |

It is certified that error appears in the above-identified patent and that said Letters Patent is hereby corrected as shown below:

In the Claims

Column 136, Line 27, Claim 23, delete "FIT" and insert -- Fv --.

Signed and Sealed this
Tenth Day of December, 2024

Katherine Kelly Vidal
*Director of the United States Patent and Trademark Office*